(12) United States Patent
Lichter et al.

(10) Patent No.: US 8,680,082 B2
(45) Date of Patent: *Mar. 25, 2014

(54) CONTROLLED RELEASE CORTICOSTEROID COMPOSITIONS AND METHODS FOR THE TREATMENT OF OTIC DISORDERS

(75) Inventors: Jay Lichter, Rancho Santa Fe, CA (US); Benedikt Vollrath, San Diego, CA (US); Andrew M. Trammel, Olathe, KS (US); Sergio G. Durón, San Diego, CA (US); Fabrice Piu, San Diego, CA (US); Luis A. Dellamary, San Marcos, CA (US); Qiang Ye, San Diego, CA (US); Carl Lebel, Malibu, CA (US); Michael Christopher Scaife, Los Altos, CA (US); Jeffrey P. Harris, La Jolla, CA (US)

(73) Assignees: Otonomy, Inc., San Diego, CA (US); The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/190,323

(22) Filed: Jul. 25, 2011

(65) Prior Publication Data

US 2011/0319373 A1 Dec. 29, 2011

Related U.S. Application Data

(63) Continuation of application No. 12/466,310, filed on May 14, 2009, now Pat. No. 8,030,297.

(60) Provisional application No. 61/127,713, filed on May 14, 2008, provisional application No. 61/060,425, filed on Jun. 10, 2008, provisional application No. 61/074,583, filed on Jun. 20, 2008, provisional application No. 61/094,384, filed on Sep. 4, 2008, provisional application No. 61/101,112, filed on Sep. 29, 2008, provisional application No. 61/140,033, filed on Dec. 22, 2008, provisional application No. 61/095,248, filed on Sep. 8, 2008, provisional application No. 61/087,940, filed on Aug. 11, 2008, provisional application No. 61/082,450, filed on Jul. 21, 2008.

(30) Foreign Application Priority Data

Dec. 22, 2008 (GB) .................................. 0823378.5

(51) Int. Cl.
*A01N 45/00* (2006.01)
*A61K 31/56* (2006.01)
*A61K 47/30* (2006.01)
*C07J 1/00* (2006.01)
*A61K 9/14* (2006.01)

(52) U.S. Cl.
USPC ........ 514/169; 514/772.3; 552/502; 424/486; 424/489

(58) Field of Classification Search
USPC ......... 514/169, 772.3; 552/502; 424/486, 489
See application file for complete search history.

(56) References Cited

U.S. PATENT DOCUMENTS

| 4,188,373 | A | | 2/1980 | Krezanoski |
|---|---|---|---|---|
| 4,478,822 | A | | 10/1984 | Haslam et al. |
| 4,968,507 | A | * | 11/1990 | Zentner et al. ................ 424/465 |
| 5,292,516 | A | | 3/1994 | Viegas et al. |
| 5,503,848 | A | | 4/1996 | Perbellini et al. |
| 6,177,434 | B1 | | 1/2001 | Kopke et al. |
| 6,201,065 | B1 | | 3/2001 | Pathak et al. |
| 6,239,113 | B1 | | 5/2001 | Dawson et al. |
| 6,284,804 | B1 | | 9/2001 | Singh et al. |
| 6,316,011 | B1 | | 11/2001 | Ron et al. |
| 6,359,016 | B2 | | 3/2002 | Singh et al. |
| 6,392,036 | B1 | | 5/2002 | Karlsson et al. |
| 6,488,952 | B1 | | 12/2002 | Kennedy et al. |
| 6,509,327 | B1 | | 1/2003 | Cagle et al. |
| 6,548,527 | B2 | | 4/2003 | Rahman et al. |
| 6,649,621 | B2 | | 11/2003 | Kopke et al. |
| 6,740,664 | B2 | | 5/2004 | Cagle et al. |
| 7,001,615 | B1 | | 2/2006 | Singh et al. |
| 7,220,431 | B2 | | 5/2007 | Sawchuk et al. |
| 7,524,834 | B2 | | 4/2009 | Karlsson et al. |
| 8,030,297 | B2 | | 10/2011 | Lichter et al. |
| 8,390,018 | B2 | | 3/2013 | Jang |
| 2001/0034339 | A1 | | 10/2001 | Singh et al. |

(Continued)

FOREIGN PATENT DOCUMENTS

EP 0551626 A1 7/1993
JP 20010-520188 4/1999

(Continued)

OTHER PUBLICATIONS

Ahn et al., "Lipoic acid rescues DBA mice from early-onset age-related hearing impairment," Neuroreport 19(13):1265-9, 2008.
Arnold et al., "Novel slow- and fast-type drug release round-window microimplants for local drug application to the cochlea: an experimental study in guinea pigs," Audiol Neurootol 10(1):53-63, 2005.
Auris Medical, press release reporting initiating of phase I/II clinical trial with AM-101, Feb. 22, 2007.
Auris Medical, press release reporting results of phase I/II clinical trial with AM-111, Jun. 21, 2006.

(Continued)

*Primary Examiner* — Sarah Pihonak
(74) *Attorney, Agent, or Firm* — Wilson Sonsini Goodrich & Rosati

(57) ABSTRACT

Disclosed herein are compositions and methods for the treatment of otic disorders with steroid, NSAID, and/or adenosine triphosphatase ("ATPase") modulator agents. In these methods, the steroidal, NSAID, and/or ATPase compositions and formulations are administered locally to an individual afflicted with an otic disorder, through direct application of these compositions and formulations onto or via perfusion into the targeted auris structure(s).

9 Claims, 10 Drawing Sheets

(56) References Cited

U.S. PATENT DOCUMENTS

| | | | |
|---|---|---|---|
| 2002/0169142 | A1 | 11/2002 | Jafari et al. |
| 2003/0092776 | A1 | 5/2003 | Ron et al. |
| 2003/0139382 | A1 | 7/2003 | Wall et al. |
| 2003/0229333 | A1 | 12/2003 | Ashton et al. |
| 2004/0082509 | A1 | 4/2004 | Bonny |
| 2004/0101506 | A1 | 5/2004 | Fust |
| 2004/0101560 | A1 | 5/2004 | Sawchuk et al. |
| 2004/0204471 | A1 | 10/2004 | Seibert |
| 2005/0147585 | A1 | 7/2005 | Schwarz |
| 2005/0214338 | A1 | 9/2005 | Guitton et al. |
| 2005/0287200 | A1 | 12/2005 | Murthy |
| 2006/0013858 | A1 | 1/2006 | Trune |
| 2006/0046970 | A1 | 3/2006 | Bowman et al. |
| 2006/0063802 | A1 | 3/2006 | Guitton et al. |
| 2006/0264897 | A1 | 11/2006 | Lobl et al. |
| 2006/0269602 | A1 | 11/2006 | Dasch et al. |
| 2007/0048338 | A1 | 3/2007 | Ladd |
| 2007/0065374 | A1 | 3/2007 | Liversidge et al. |
| 2007/0110788 | A1 | 5/2007 | Hissong et al. |
| 2007/0178051 | A1 | 8/2007 | Pruitt et al. |
| 2008/0103118 | A1 | 5/2008 | Clement et al. |
| 2008/0124385 | A1 | 5/2008 | Campbell |
| 2009/0156566 | A1 | 6/2009 | Wall et al. |
| 2009/0246255 | A1 | 10/2009 | Meyer |
| 2009/0297533 | A1 | 12/2009 | Lichter et al. |
| 2009/0306225 | A1 | 12/2009 | Lichter et al. |
| 2009/0324552 | A1 | 12/2009 | Lichter et al. |
| 2009/0325938 | A1 | 12/2009 | Lichter et al. |
| 2010/0004225 | A1 | 1/2010 | Lichter et al. |
| 2010/0009952 | A1 | 1/2010 | Lichter et al. |
| 2010/0015228 | A1 | 1/2010 | Lichter et al. |
| 2010/0015263 | A1 | 1/2010 | Lichter et al. |
| 2010/0016218 | A1 | 1/2010 | Lichter et al. |
| 2010/0016450 | A1 | 1/2010 | Lichter et al. |
| 2010/0021416 | A1 | 1/2010 | Lichter et al. |
| 2010/0022661 | A1 | 1/2010 | Lichter et al. |
| 2010/0036000 | A1 | 2/2010 | Lichter et al. |
| 2010/0197800 | A1 | 8/2010 | Friedman et al. |
| 2010/0273864 | A1 | 10/2010 | Lichter et al. |
| 2011/0166060 | A1 | 7/2011 | Simons et al. |
| 2013/0116210 | A1 | 5/2013 | Lichter et al. |

FOREIGN PATENT DOCUMENTS

| | | |
|---|---|---|
| JP | 2004-507450 | 10/2001 |
| JP | 2004-536836 | 1/2003 |
| JP | 2006-97031 | 4/2006 |
| JP | 2006-111585 | 4/2006 |
| WO | WO 97/38698 | 10/1997 |
| WO | WO 99/24051 | 5/1999 |
| WO | WO 99/32151 | 7/1999 |
| WO | WO 02/056890 | 7/2002 |
| WO | WO 03/017990 | 3/2003 |
| WO | WO 03/034979 | 5/2003 |
| WO | WO 03/071986 | 9/2003 |
| WO | WO 2004/050021 | 6/2004 |
| WO | WO 2006/099325 | 9/2006 |
| WO | WO 2006/102964 | 10/2006 |
| WO | WO 2007/031098 | 3/2007 |
| WO | WO 2007/031280 | 3/2007 |
| WO | WO 2007/037874 | 4/2007 |
| WO | WO 2007/037886 | 4/2007 |
| WO | WO 2007/038949 | 4/2007 |
| WO | WO 2008/001341 | 1/2008 |
| WO | WO 2008/076556 | 6/2008 |
| WO | WO-2009-132050 | 10/2009 |

OTHER PUBLICATIONS

Battaglia et al., "Combination therapy (intratympanic dexamethasone + high-dose prednisone taper) for the treatment of idiopathic sudden sensorineural hearing loss," Otol Neurotol 29(4):453-60, 2008.

Bird et al., "Intratympanic versus intravenous delivery of methylprednisolone to cochlear perilymph," Otology & Neurotology 28(8):1124-1130, 2007.

Campbell et al., "Oral-D-methionine (MRX-1024) significantly protects against cisplatininduced hearing loss: a phase II study in humans," Abst 32$^{nd}$ Ann MidWinter Res Meeting, ARO Abstracts 32:7, Feb. 14-19, 2009.

Chen and Nathans, "Estrogen-related receptor beta/NR3B2 controls epithelial cell fate and endolymph production by the stria vascularis," Dev Cell 13(3):325-37, 2007.

Chen et al., "Design and preparation of thermosensitive in situ gel of dexamethasone sodium phosphate," I Guangdong Coll Pharm 23(5):518-21, 2007 (English abstract).

Chen et al., "Evaluation of thermosensitive in situ gel using dynamic theological experiment," Chin Pharm J 43(6):444-447, 2008 (English abstract).

Chen et al., "In vivo distribution and pharmacokinetics of dexamethasone sodium phosphate thermosensitive in situ gel following intratympanic injection," Sichuan Da Xue Xue Bao Yi Xue Ban 37(3):456-9, 2006 (English translation).

Chen et al., "Preparation and characterization of dexamethasone acetate-loaded solid lipid nanoparticles," Chinese I Pharm 39(4):261-264, 2008 (English abstract).

Chen et al,, "Study on dexamethasone thermosensitive in situ gel for treating deafness," Chin Pharm J 41(9):685-688, 2006 (English abstract).

CIPRODEX, product label, 2009.

Combined search and examination report in UK Patent Application No. GB0823378.5 dated Feb. 27, 2009.

Combined search and examination report in UK Patent Application No. GB0912650.9 dated Oct. 23, 2009.

Combined search and examination report in UK Patent Application No. GB0907065.7 dated Nov. 16, 2009.

Examination report in UK Patent Application No. GB0823378.5 dated Oct. 23, 2009.

PCT/US2008/061330 International Search Report mailed Jul. 31, 2008.

PCT/US2009/067552 International Search Report mailed Aug. 18, 2010.

PCT/US2009/003066 International Search Report mailed Jan. 5, 2010.

Dellamary et al., "Assessing and optimizing osmolality of poloxamer 407 hydrogel formulations for sustained inner ear drug delivery," Abstract, 2010 AAPS National Biotechnology Conference in San Francisco.

Dellamary et al., "Assessing and optimizing osmolality of poloxamer 407 hydrogel formulations for sustained inner ear drug delivery," Poster, 2010 AAPS National Biotechnology Conference in San Francisco.

Dellamary et al., "Development of poloxamer hydrogel formulations for sustained inner ear drug delivery," Abstract, 2010 AAPS National Biotechnology Conference in San Francisco.

Dellamary et al., "Development of poloxamer hydrogel formulations for sustained inner ear drug delivery," Poster, 2010 AAPS National Biotechnology Conference in San Francisco.

Dellamary et al., "Novel poloxamer hydrogel formulations for sustained drug delivery to the middle ear," Abstract, 2010 AAPS Annual Meeting in New Orleans, Nov. 14-Nov. 18.

Dellamary et al., "Novel poloxamer hydrogel formulations for sustained inner ear drug delivery," Abstract, Controlled Release Society 37th Annual Meeting and Exposition in Portland Jul. 10-14, 2010.

Dellamary et al., "Novel poloxamer hydrogel formulations for sustained inner ear drug delivery," Poster, Controlled Release Society 37th Annual Meeting and Exposition in Portland Jul. 10-14, 2010.

Dellamary et al., "Sustained drug delivery to the middle ear via a novel poloxamer hydrogel formulation," Poster, 2010 AAAPS Annual Meeting in New Orleans, Nov. 14-Nov. 18.

Derin et al., "The effects of L-carnitine on presbyacusis in the rat model," Clin Otolaryngol Allied Sci 29(3):238-41, 2004.

Dourmishev et al., "Waardenburg syndrome," Intl J Dermatol 39:656-663 (1999).

Endo et al., "Novel strategy for treatment of inner ears using a biodegradable gel," Laryngoscope 115(11):2016-20, 2005.

Feng et al., Zhonghua er Bi Yan Hou Tou Jing Wai Ke Za Zhi, 2007 Jun;42(6):443-6 (English Abstract).

(56) References Cited

OTHER PUBLICATIONS

Feng et al., Zhonghua Yi Xue Za Zhi, Aug. 28, 2007;87(32):2289-91 (English Translation).
Fernandez et al., "Self-curing controlled release systems for steroids. Application of prednisolone-based polymeric systems to ear diseases," Biomaterials 26(16):3311-8, 2005.
Friedman et al., "GRM7 variants confer susceptibility to age-related hearing impairment," Hum Mol Genet 18(4):785-96, 2009.
Garduno-Anaya et al., "Dexamethasone inner ear perfusion by intratympanic injection in unilateral Moniere's disease: a two-year prospective, placebo-controlled, double-blind, randomized trial," Otolaryngol Head Neck Surg 133(2):285-94, 2005.
Gubbels et al., "Functional auditory hair cells produced in the mammalian cochlea by in utero gene transfer," Nature 455(7212):537-41, 2008.
Guyot et al., "Intratympanic application of an antiviral agent for the treatment of Merare's disease," ORL J Otorhinolaryngol Relat Spec 70(1):21-6; discussion 26-7, 2008.
Hall et al., "Anti-Pneumocystis Activities of Aromatic Diamidoxine Prodrugs," Antimicrobial Agents & Chemotherapy, 1998, American Society for Microbiology 42(4):666-674 (1998).
Hargunani et al., "Intratympanic injection of dexamethasone: time course of inner ear distribution and conversion to its active form," Otol Neurotol 27(4):564-9, 2006.
Harris et al., "Prevention of noise-induced hearing loss with Src-PTK inhibitors," Hear Res 208(1-2):14-25, 2005.
Harris et al., "Treatment of corticosteroid-responsive autoimmune inner ear disease with methotrexate: a randomized controlled trial," JAMA 290(14):1875-83, 2003.
Hill et al., "Cisplatin-induced ototoxicity: effect of intratympanic dexamethasone injections," Otol Neurotol 29:1005-11, 2008.
Hoffer et al., "Transtympanic management of tinnitus," Otolaryngol Clin North Am 36(2):353-8, 2003.
Hoshino et al., "The non-steroidal anti-inflammatory drugs protect mouse cochlea against acoustic injury," Tohoku J Exp Med 216(1):53-9, 2008.
Inaoka et al., "Local application of hepatocyte growth factor using gelatin hydrogels attenuates noise-induced bearing loss in guinea pigs," Acta Otolaryngol 129(4):453-7, 2009.
Jia et al., "Intratympanic dexamethasone for refractory sudden deafness," Lin Chung Er Bi Yan Hou Tou Jing Wai Ke Za Zhi 22(7):309-11, 2008 (English translation).
Karolewicz and Pluta, "Thermosensitive polymers in drug form technology II. Possibilities of use of thermosensitive polymers as active substance carriers," Polimery W Medycynie 38(1):15-26, 2008 (English language abstract).
Kazama et al., "Lithium effectively complements vasopressin V2 receptor antagonist in the treatment of hyponatraemia of SIADH rats," Nephrol Dial Transplant 22(1):68-76, 2007.
Keithley et al., "GDNF protects the cochlea against noise damage," Neuroreport 9(10):2183-7, 1998.
Kim et al., "Effects of tumor necrosis factor alpha antagonist, platelet activating factor antagonist, and nitric oxide synthase inhibitor on experimental otitis media with effusion," Ann Otol Rhino! Laryngol 115(8):617-23, 2006.
Kitahara et al., "Up-regulation of cochlear aquaporin-3 mRNA expression after intraendolymphatic sac application of dexamethasone," Neurol Res. 25(8):865-70, 2003.
Lamm and Arnold, "The effect of prednisolone and non-steroidal anti-inflammatory agents on the normal and noise-damaged guinea pig inner ear," Hear Res 115(1-2):149-61, 1998.
Lavreysen and Dautzenberg, "Therapeutic potential of group III metabotropic glutamate receptors," Curr Med Chem I 5(7): 671-84, 2008.
Lee et al., "Novel therapy for hearing loss: delivery of insulin-like growth factor 1 to the cochlea using gelatin hydrogel," Otol Neurotol 28(7):976-81, 2007.

Lee et al., "Regional delivery of vancomycin using pluronic F-127 to inhibit methicillin resistant *Staphylococcus aureus* (MRSA) growth in chronic otitis media in vitro and in vivo," J Control Release 96(1):1-7, 2004.
Liu et al., "Permeability of different Dexamethasone drugs through round window membrane," ZhonghuaEr Bi Yan Hou Tou Jing Wai Ke-Za Zhi 41(3):211-5, 2006 (English abstract).
McCarthy et al., "Alport syndrome: a review," Clinical Eye and Vision Care 12:139-150 (2000).
McGuinness and Shepherd, "Exogenous BDNF rescues rat spiral ganglion neurons in vivo," Otol Neurotol 26(5):1064-72, 2005.
Meltser et al., "Estrogen receptor beta protects against acoustic trauma in mice," J Clin Invest 118(4):1563-70, 2008.
Miceli et al., "Molecular pharmacology and therapeutic potential of neuronal Kv7-modulating drugs," Curr Opin Phannacol 8(1):65-74, 2008.
Mitsukawa et al., "A selective metabotropic glutamate receptor 7 agonist: activation of receptor signaling via an allosteric site modulates stress parameters in vivo," Proc Natl Acad Sci U S A 102(51):18712-7, 2005.
Mostafa, "Transtympanic Membrane Delivery of Antibiotics-Pharmacokinetic Studies in Chinchillas," Dissertation submitted to the Graduate School of the University of Minnesota in Mar. 2007.
Nakagawa and Ito, "Local drug delivery to inner ear for treatment of hearing loss," Curr Drug Ther 3:143-147, 2008.
Nance et al., "The Genetics of Deafness," Mental Retardation and Developmental Disabilities, 2003, Wiley-Liss, vol. 9, pp. 109-119.
Nishimaki et al., "Reduction of metabotropic glutamate receptor-mediated heterosynaptic inhibition of developing MNTB-LSO inhibitory synapses," Eur J Neurosci 26(2):323-30, 2007.
Nouvian et al., "Degeneration of sensory outer hair cells following pharmacological blockade of cochlear KCNQ channels in the adult guinea pig," Eur .1 Neurosci 17(12):2553-62, 2003.
Park et al., "Effect of inhibitor of tumor necrosis factor-alpha and oxatomide on immune mediated otitis media," Laryngoscope 116(9):1642-6, 2006.
Parnes et al., "Corticosteroid pharmacokinetics in the inner ear fluids: an animal study followed by clinical application," Laryngoscope 109(7 Pt 2 Supplement No. 91):1-17, 1999.
Paulson et al., "A novel controlled local drug delivery system for inner ear disease," Laryngoscope 118(4);706-11, 2008.
Peng et al., "Clinical investigation of different routes of administration of dexamethasone on sudden deafness," Lin Chung Er Bi Yan Hou Tou ling Wai Ke Za Zhi 22(10):442-5, 2008 (English translation).
Piu et al., "Towards predicting human inner ear pharmacokinetics: allometric scaling using guinea pigs and sheep," Abstract, ARO Meeting , Feb. 6-10, 2010.
Piu, "OTO-104: a sustained release dexamethasone hydrogel formulation for the treatment of Meniere's disease," Oral presentation title; Recent topics in Meniere's disease treatment, Nov. 16, 2010.
Piu et al., "OTO-104: a Sustained-Release Dexamethasone Hydrogel for the Treatment of Otic Disorders, " Otol & Neurology vol. 32(1):171-179(2011).
Plontke et al., "Rapid clearance of methylprednisolone after intratympanic application in humans. Comment on: Bird PA, Begg EI, Zhang M, et al. Intratympanic versus intravenous delivery of methylprednisolone to cochlear perilymph. Otol Neurotol 2007; 28:1124-30," Otol Neurotol 29(5);732-3, 2008.
Pondugula et al., "Glueocorticoid regulation of genes in the amiloridesensitive sodium transport pathway by semicircular canal duct epithelium of neonatal rat," Physiol Genomics 24(2):114-23, 2006.
Pondugula et al., "Glucocorticoids stimulate cation absorption by semicircular canal duct epithelium via epithelial sodium channel," Am I Physiol Renal Physiol 286(6):F1127-35, 2004.
Psillas et al., "Potential efficacy of early treatment of acute acoustic trauma with steroids and piracetam after gunshot noise," Eur Arch Otorhinolaryngol 265(12):1465-9, 2008.
Puel, "Chemical synaptic transmission in the cochlea," Prog Neurobiol 47(6):449-76, 1995.

(56) References Cited

OTHER PUBLICATIONS

Salt et al., "Distribution of Dexamethasone and Preservation of Inner Ear Function following Intratympanic Delivery of a Gel-Based Formulation," Audiology Neurology 16:323-335 (2011).
Salt et al., "Local Inner Ear Drug Delivery and Pharmacokinetics," Drug Discovery Today 10(19):1299-1306 (2005).
Satoh et al, "Tumor necrosis factor-alpha, an initiator, and etanercept, an inhibitor of cochlear inflanunation," Laryngoscope 112(9):1627-34, 2002.
Schoepp et al., "Pharmacological agents acting at subtypes of metabotropic glutamate receptors," Neuropharmacology 38(10):1431-76, 1999.
Seidman et al., "Anti-intercellular adhesion molecule-1 antibody's effect on noise damage," Laryngoscope 119(4):707-12, 2009.
She et al., "A short term study on the efficacies of intratympanic prednisolone and dexamethasone injection for subjective tinnitus," Lin Chung Er Bi Yan Hou Tou Jing Wai Ke Za Zhi 22(19):871-3, 2008 (English translation).
Shepherd et al., "Neurotrophins and electrical stimulation for protection and repair of spiral ganglion neurons following sensorineural hearing loss," Hear Res 242(1-2):100-9, 2008.
147• Shinohara et al., "Neurotrophic factor intervention restores auditory function in deafened animals," Proc Natl Acad Sci U S a 99(3):1657-60, 2002.
Song, "Design and Synthesis of Factor Xa Inhibitors and Their Prodrugs," Biogranic & Medicinal Chemistry Letters vol. 13:297-300 (2003).
Sun et al., "In vitro permeability of round window membrane to transforming dexamethasone with delivery vehicles—a dosage estimation," Chin Med J (Engl) 120(24):2284-9, 2007.
Synphora AB, website printout for JB004/A, 2009.
Tabuchi et al., "Hearing impairment in TRPV4 knockout mice," Neurosci Lett 382(3):304-8, 2005.
Taguchi et al., "Expressions of aquaporin-2, vasopressin type 2 receptor, transient receptor potential channel vanilloid (TRPV)1, and TRPV4 in the human endolymphatic sac," Laryngoscope 117(4):695-8, 2007.
Tahera et al., "NF-kB mediated glucocorticoid response in the inner ear after acoustic trauma," J Neurosci Res 1;83(6):1066-76, 2006.
Takeda and Taguchi, "Aquaporins as potential drug targets for Meniere's disease and its related diseases," Handb Exp Pharmacol 190:171-84, 2009.
Takeda et al., "Decompression effects of erythritol on endolymphatic hydrops," Auris Nasus Larynx 36(2):146-51, 2009.
156. Takeda et al., "The effects of V2 antagonist (OPC-31260) on endolymphatic hydrops," Hear Res 182(1-2):9-18, 2003.
Takemura et al., "Direct inner ear infusion of dexamethasone attenuates noise-induced trauma in guinea pig," Hear Res 196(1-2):58-68, 2004.
Takumida and Anniko, "Nitric oxide in the inner ear,"Cur Opin Neural 15(1):11-5, 2002.
Tang et al., "COUP-TFI controls Notch regulation of hair cell and support cell differentiation," Development 133(18):3683-93, 2006.
The Royal National Institute for Deaf People (RNID), advertisement insert in Nature Reviews Drug Discovery, May, 2009.
Thorne et al., "Potential role of purinergic signalling in cochlear pathology," Audiol Neurootol 7(3):180-4, 2002.
Van Wijk et al., "Local perfusion of the tumor necrosis factor alpha blocker infliximab to the inner ear improves autoimmune neurosensory hearing loss," Audiol Neurootol 11(6):357-65, 2006.
Wang et al., "Principles of Inner Ear Sustained Release Following Intratympanic Administration," Laryngoscope 121:385-391 (2011).
Wang et al, "Pharmacokinetic and toxicity profile of OTO-104—a sustained release," ARO MidWinter meeting, Abstract 644, Feb. 8, 2010.
Wang et al, "Pharmacokinetic and toxicity profile of the clinical candidate OTO-104: a sustained release dexamethasone hydrogel for inner ear delivery," 2010 Abstracts selected for AOS spring meeting, Las Vegas, NV, May 1-2, 2010.

Wang et al., "A novel dual inhibitor of calpains and lipid peroxidation (BN82270) rescues the cochlea from sound trauma," Neuropharmacology 52(6):1426-37, 2007.
Wang et al., "Dose-dependent sustained release of dexamethasone in inner ear cochlear fluids using a novel local delivery approach," Audio! Neurotol 14:393-401, 2009.
Wang et al., "Over-expression of X-linked inhibitor of apoptosis protein slows presbycusis in C57BL/6J mice," Neurobiol Aging Aug. 26, 2008 [Epub ahead of print].
Wang et al., "Pharmacokinetic and safety profile of OTO-104: a sustained release dexamethasone hydrogel for inner ear delivery," Abstract, ARO Meeting, Feb. 6-10, 2010.
Wang et al., "Pharmacokinetic and toxicity profile of the clinical candidate OTO-104: a sustained release dexamethasone hydrogel for inner ear delivery," Abstract, COSM Meeting, May 1-2, 2010.
Wang et al., "Pharmacokinetics of dexamethasone solution following intratympanic injection in guinea pig and sheep," Audiol Neurotol 16:233-241, 2010.
Watanabe et al., "Inhibition of inducible nitric oxide synthase lowers the cochlear damage by lipopolysaccharide in guinea pigs," Free Radic Res 32(4):363-70, 2000.
Watanabe et al., "Nitric oxide synthase inhibitor reduces the apoptotic change in the cisplatin-treated cochlea of guinea pigs," Anticancer Drugs 11(9):731-5, 2000.
Watanabe et al., "Nitric oxide synthase inhibitor suppresses the ototoxic side effect of cisplatin in guinea pigs," Anticancer Drugs 11(5):401-6, 2000.
Yamamoto et al, "Inhibition of Notch/RBP-J signaling induces hair cell formation in neonate mouse cochleas," J Mol Med 84(1):37-45, 2006.
Yang et al., "Intratympanic immunosuppressives for prevention of inunune-mediated sensorineural hearing loss," Am J Otol 21(4):499-504, 2000.
Yildirim et al., "Effect of intratympanic dexamethasone on noise-induced temporary threshold shift," Laryngoscope 115(7):1219-22, 2005.
Zheng et al., "Vanilloid receptors in hearing: altered cochlear sensitivity by vanilloids and expression of TRPV1 in the organ of corti," J Neurophysiol 90(1):444-55, 2003.
Zhou et al., "Intratympanic administration of methylprednisolone reduces impact of experimental intensive impulse noise trauma on hearing," Acta Oto-Laryngologica 129:602-607, 2009.
U.S. Appl. No. 12/486,697 Office Action dated Apr. 26, 2011.
U.S. Appl. No. 12/504,553 Office Action dated Feb. 14, 2012.
U.S. Appl. No. 12/466,310 Office Action mailed Jan. 12, 2011.
PCT/US09/003066 Int'l. Prelim. Report on Patentability and Written Opinion dated Feb. 9, 2011.
Elgen, Remington's Pharmaceuticals Sciences, 1985, 17th ed., pp. 1836-1837.
Fedder et al., Remington: The Science and Practice of Pharmacy, 2005, Lippincott Williams and Wilkins, 21ed., pp. 1992-1993.
Feng et al., "In vitro and in vivo biodegradation of sustained-release vehicle poloxamer 407 in situ gel," Lin Chung Er Bi Van Hou Tou Jing Wai Ke Za Zhi 22(1):28-31, 2008 (English translation).
Hahn et al., "Cochlear microdialysis for quantification of dexamethasone and fluorescein entry into scala tympani during round window administration," Hearing Research, 2006, 212(1-2):pp. 236-244.
Kopke et al., "Targeted Topical Steriod Therapyin Sudden Sensorineural Hearing Loss," Otology & Neurotology, vol. 22, No. 4 Jul. 2001, pp. 475-479.
U.S. Appl. No. 12/837,286 Office Action dated Aug. 30, 2012.
U.S. Appl. No. 13/190,327 Office action mailed Mar. 12, 2013.
U.S. Appl. No. 13/190,329 Office action mailed Apr. 4, 2013.
Letter indicating that an opposition brief was filed in connection with Peruvian Patent Application No. 000959-2009/DIN, Aug. 20, 2010.
PCT/US10/053214 Search Report dated Jul. 1, 2011.
PCT/US2009/051172 International Search report mailed Feb. 18, 2010.
U.S. Appl. No. 13/500,971 Office Action dated Mar. 11, 2013.
U.S. Appl. No. 13/190,330 Office Action dated Oct. 15, 2012.
U.S. Appl. No. 12/506,091 Office Action dated Feb. 22, 2012.
U.S. Appl. No. 12/837,286 Office Action dated Mar. 13, 2013.

(56) References Cited

OTHER PUBLICATIONS

U.S. Appl. No. 12/466,310 Office Action dated Apr. 12, 2011.
U.S. Appl. No. 13/190,327 Final Office Action issued Sep. 17, 2013.
U.S. Appl. No. 13/500,971 Office Action issued Sep. 18, 2013.
U.S. Appl. No. 13/190,327 Notice of Allowance mailed Oct. 9, 2013.
U.S. App. No. 12/472,034 Notice of Allowance dated Sep. 30, 2013.
Varshosaz, et al., the Open Drug Delivery Journal, vol. 2, pp. 61-70, Published 2008.

* cited by examiner

A

B

CONTROLLED RELEASE CORTICOSTEROID COMPOSITIONS AND METHODS FOR THE TREATMENT OF OTIC DISORDERS

CROSS-REFERENCE

This application is a continuation of U.S. application Ser. No. 12/466,310 filed May 14, 2009 now U.S. Pat. No. 8,030, 297 which claims the benefit of U.S. Provisional Application No. 61/127,713 filed May 14, 2008, U.S. Provisional Application No. 61/060,425 filed Jun. 10, 2008, U.S. Provisional Application No. 61/074,583 filed Jun. 20, 2008, U.S. Provisional Application No. 61/094,384 filed Sep. 4, 2008, U.S. Provisional Application No. 61/101,112 filed Sep. 29, 2008, U.S. Provisional Application No. 61/140,033 filed Dec. 22, 2008, U.S. Provisional Application No. 61/095,248 filed Sep. 8, 2008, U.S. Provisional Application No. 61/087,940 filed Aug. 11, 2008, U.S. Provisional Application No. 61/082,450 filed Jul. 21, 2008, and GB Application No. 0823378.5 filed Dec. 22, 2008, which are incorporated by reference in their entirety.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

SUMMARY OF THE INVENTION

Described herein are compositions, formulations, manufacturing methods, therapeutic methods, uses, kits, and delivery devices for the controlled release of at least one corticosteroid to at least one structure or region of the ear. Disclosed herein are controlled release formulations for delivering a corticosteroid to the ear. In some embodiments, the target portion of the ear is the middle ear or auris media. In some embodiments, the target portion of the ear is the inner ear, or auris interna. In other embodiments, the target portion of the ear is both the auris media and the auris interna. In some embodiments, the controlled release formulations further comprise a rapid or immediate release component for delivering a corticosteroid to the targeted auris structure. All formulations comprise excipients that are auris-acceptable.

Also disclosed herein are methods, compositions and devices for the treatment of otic disorders by administration of controlled release formulations comprising a corticosteroid. In some embodiments the otic disorder is Meniere's disease, Meniere's syndrome, or sensorineural hearing loss. In additional embodiments, the otic disorder is an autoimmune inner ear disorder (AIED). Also disclosed herein is the local delivery of controlled release steroid compositions and formulations to suppress or ameliorate auditory and vestibular impairment as a result of AIED, which may be provoked by other autoimmune conditions, including Ankylosing Spondylitis, Systemic Lupus Erythematosis (SLE), Sjögren's Syndrome, Cogan's disease, ulcerative colitis, Wegener's granulomatosis, rheumatoid arthritis, scleroderma and Behçet's disease (also known as Bechet's disease and adamantiades). In other embodiments, the otic disorder is otitis media. In additional embodiments the otic disorder is vestibular neuronitis, postural vertigo, Ramsay Hunt's Syndrome (herpes zoster infection), syphilis infection, drug-induced inner ear damage, auditory nerve tumors, presbycusis, otosclerosis, or temporomandibular joint disease.

Described herein are controlled release compositions and devices for treating otic disorders comprising a therapeutically-effective amount of a corticosteroid, a controlled release auris-acceptable excipient and an auris-acceptable vehicle. In one aspect, the controlled release auris-acceptable excipient is chosen from an auris-acceptable polymer, an auris-acceptable viscosity enhancing agent, an auris-acceptable gel, an auris-acceptable hydrogel, an auris-acceptable thermoreversible gel or combinations thereof.

In some embodiments, the compositions are formulated for pH, and a practical osmolality and/or osmolarity to ensure that homeostasis of the target auris structure is maintained. A perilymph-suitable osmolarity/osmolality is a practical/deliverable osmolarity/osmolality that maintains the homeostasis of the target auris structure during administration of the pharmaceutical formulations described herein.

For example, the osmolarity of the perilymph is between about 270-300 mOsm/L, and the compositions described herein are optionally formulated to provide a practical osmolarity of about 150 to about 1000 mOsm/L. In certain embodiments, the formulations described herein provide a practical and/or deliverable osmolarity within about 150 to about 500 mOsm/L at the target site of action (e.g., the inner ear and/or the perilymph and/or the endolymph). In certain embodiments, the formulations described herein provide a practical osmolarity within about 200 to about 400 mOsm/L at the target site of action (e.g., the inner ear and/or the perilymph and/or the endolymph). In certain embodiments, the formulations described herein provide a practical osmolarity within about 250 to about 320 mOsm/L at the target site of action (e.g., the inner ear and/or the perilymph and/or the endolymph). In certain embodiments, the formulations described herein provide a perilymph-suitable osmolarity within about 150 to about 500 mOsm/L, about 200 to about 400 mOsm/L or about 250 to about 320 mOsm/L at the target site of action (e.g., the inner ear and/or the perilymph and/or the endolymph). In certain embodiments, the formulations described herein provide a perilymph-suitable osmolarity within about 150 to about 500 mOsm/kg, about 200 to about 400 mOsm/kg or about 250 to about 320 mOsm/kg at the target site of action (e.g., the inner ear and/or the perilymph and/or the endolymph). Similarly, the pH of the perilymph is about 7.2-7.4, and the pH of the present formulations is formulated (e.g., with the use of buffers) to provide a perilymph-suitable pH of about 5.5 to about 9.0, about 6.0 to about 8.0 or about 7.0 to about 7.6. In certain embodiments, the pH of the formulations is within about 6.0 to about 7.6. In certain instances, the pH of the endolymph is about 7.2-7.9, and the pH of the present formulations is formulated (e.g., with the use of buffers) to be within about 5.5 to about 9.0, within about 6.5 to about 8.0 or within about 7.0 to about 7.6.

In some aspects, the controlled-release auris-acceptable excipient is biodegradable and/or bioeliminated (e.g., degraded and/or eliminated through urine, feces or other routes of elimination). In another aspect, the controlled release composition further comprises an auris-acceptable mucoadhesive, an auris-acceptable penetration enhancer or an auris-acceptable bioadhesive.

In one aspect, the controlled release composition is delivered using a drug delivery device, which is a needle and syringe, a pump, a microinjection device, and in situ forming spongy material or combinations thereof. In some embodiments, the corticosteroid of the controlled release composition has limited or no systemic release, is toxic when administered systemically, has poor pK characteristics or combinations thereof. In further aspects, the corticosteroid is dexamethasone, betamethasone, prednisolone, methylprednisolone, deoxycorticosterone, 11-deoxycorticosterone, 18-hydroxy-11-deoxycorticosterone, beclomethasone, triamcinolone or combinations thereof. In another aspect, the corticosteroid is a phosphate or ester prodrug of the steroid. In another aspect, the corticosteroid is a salt of the steroid.

Also disclosed herein is a method for treating an otic disorder comprising administering at least once every 3, 4, 5, 6, 7, 8, 9, 10, 11, 12, 13, 14, or 15 days, at least once a week, once every two weeks, once every three weeks, once every four weeks, once every five weeks, or once every six weeks; or once a month, once every two months, once every three months, once every four months, once every five months, once every six months, once every seven months, once every eight months, once every nine months, once every ten months, once every eleven months, or once every twelve months with the compositions and formulations disclosed herein. In particular embodiments, the controlled release formulations described herein provide a sustained dose of corticosteroid to the inner ear between subsequent doses of the controlled release formulation. That is, taking one example only, if new doses of the corticosteroid controlled release formulation are adminstered via intratympanic injection to the round window membrane every 10 days, then the controlled release formulation provides an effective dose of corticosteroid to the inner ear (e.g., across the round window membrane) during that 10-day period.

In another aspect, the composition is administered so that the composition is in contact with the round window membrane. In one aspect the composition is administered by intratympanic injection.

Provided herein are pharmaceutical compositions or devices for use in the treatment of an otic disease or condition formulated to provide a therapeutically effective amount of dexamethasone, methylprednisolone, or prednisolone, the pharmaceutical compositions or devices comprising substantially low degradation products of dexamethasone, methylprednisolone, or prednisolone, the pharmaceutical compositions or devices further comprising two or more characteristics selected from:
(i) between about 0.1% to about 10% by weight of dexamethasone, methylprednisolone, or prednisolone, or pharmaceutically acceptable prodrug or salt thereof;
(ii) between about 16% to about 21% by weight of a polyoxyethylene-polyoxypropylene triblock copolymer of general formula E106 P70 E106;
(iii) sterile water, q.s., buffered to provide a pH between about 5.5 and about 8.0;
(iv) multiparticulate dexamethasone, methylprednisolone, or prednisolone;
(v) a gelation temperature between about 19° C. to about 42° C.;
(vi) less than about 50 colony forming units (cfu) of microbiological agents per gram of formulation, and
(vii) less than about 5 endotoxin units (EU) per kg of body weight of a subject.

In some embodiments, a pharmaceutical composition or device described herein comprises:
(i) between about 0.1% to about 10% by weight of dexamethasone, methylprednisolone, or prednisolone, or pharmaceutically acceptable prodrug or salt thereof;
(ii) between about 16% to about 21% by weight of a polyoxyethylene-polyoxypropylene triblock copolymer of general formula E106 P70 E106; and
(iii) multiparticulate dexamethasone, methylprednisolone, or prednisolone.

In some embodiments, a pharmaceutical composition or device described herein comprises:
(i) between about 0.1% to about 10% by weight of dexamethasone, methylprednisolone, or prednisolone, or pharmaceutically acceptable prodrug or salt thereof;
(ii) between about 16% to about 21% by weight of a polyoxyethylene-polyoxypropylene triblock copolymer of general formula E106 P70 E106;
(iii) multiparticulate dexamethasone, methylprednisolone, or prednisolone; and
(iv) a gelation temperature between about 19° C. to about 42° C.

In some embodiments a pharmaceutical composition or device described above provides a practical osmolarity between about 150 and 500 mOsm/L. In some embodiments a pharmaceutical composition or device described above provides a practical osmolarity between about 200 and 400 mOsm/L. In some embodiments a pharmaceutical composition or device described above provides a practical osmolarity between about 250 and 320 mOsm/L.

In some embodiments, the dexamethasone, methylprednisolone, or prednisolone is released from the pharmaceutical formulation or device described above for a period of at least 3 days. In some embodiments, the dexamethasone, methylprednisolone, or prednisolone is released from the pharmaceutical formulation or device described above for a period of at least 5 days. In some embodiments, the dexamethasone, methylprednisolone, or prednisolone is released from the pharmaceutical formulation or device described above for a period of at least 10 days. In some embodiments, the dexamethasone, methylprednisolone, or prednisolone is released from the pharmaceutical formulation or device described above for a period of at least 14 days. In some embodiments, the dexamethasone, methylprednisolone, or prednisolone is released from the pharmaceutical formulation or device described above for a period of at least one month.

In some embodiments, a pharmaceutical composition or device described above comprises dexamethasone, methylprednisolone, or prednisolone as a free acid, a free alcohol, a salt or a prodrug. In some embodiments, a pharmaceutical composition or device described above comprises dexamethasone, methylprednisolone, or prednisolone as a free acid, a free alcohol, a salt or a prodrug, or a combination thereof.

In some embodiments, a pharmaceutical composition or device described above comprises dexamethasone, methylprednisolone, or prednisolone as multiparticulates. In some embodiments, a pharmaceutical composition or device described above comprises dexamethasone, methylprednisolone, or prednisolone in the form of micronized particles. In some embodiments, a pharmaceutical composition or device described above comprises dexamethasone, methylprednisolone, or prednisolone as micronized powders.

In some embodiments, a pharmaceutical composition or device described above has a pH between about 5.5 to about 8.0. In some embodiments, a pharmaceutical composition or device described above has a pH between about 6.0 to about 8.0. In some embodiments, a pharmaceutical composition or device described above has a pH between about 6.0 to about 7.6.

In some embodiments, a pharmaceutical composition or device described above contains less than 100 colony forming units (cfu) of microbiological agents per gram of formulation. In some embodiments, a pharmaceutical composition or device described above contains less than 50 colony forming units (cfu) of microbiological agents per gram of formulation. In some embodiments, a pharmaceutical composition or device described above contains less than 10 colony forming units (cfu) of microbiological agents per gram of formulation.

In some embodiments, a pharmaceutical composition or device described above contains less than 5 endotoxin units (EU) per kg of body weight of a subject. In some embodiments, a pharmaceutical composition or device described above contains less than 4 endotoxin units (EU) per kg of body weight of a subject.

In some embodiments a pharmaceutical composition or device described above provides a gelation temperature between about between about 19° C. to about 42° C. In some embodiments a pharmaceutical composition or device described above provides a gelation temperature between about between about 19° C. to about 37° C. In some embodiments a pharmaceutical composition or device described above provides a gelation temperature between about between about 19° C. to about 30° C.

In some embodiments, the pharmaceutical composition or device is an auris-acceptable thermoreversible gel. In some embodiments, the polyoxyethylene-polyoxypropylene triblock copolymer is biodegradable and/or bioeliminated (e.g., the copolymer is eliminated from the body by a biodegradation process, e.g., elimination in the urine, the feces or the like). In some embodiments, a pharmaceutical composition or device described herein further comprises a mucoadhesive. In some embodiments, a pharmaceutical composition or device described herein further comprises a penetration enhancer. In some embodiments, a pharmaceutical composition or device described herein further comprises a thickening agent. In some embodiments, a pharmaceutical composition or device described herein further comprises a dye.

In some embodiments, a pharmaceutical composition or device described herein further comprises a drug delivery device selected from a needle and syringe, a pump, a microinjection device, a wick, an in situ forming spongy material or combinations thereof.

In some embodiments, a pharmaceutical composition or device described herein is a pharmaceutical composition or device wherein the dexamethasone, methylprednisolone, or prednisolone, or pharmaceutically acceptable salt thereof, has limited or no systemic release, systemic toxicity, poor PK characteristics, or combinations thereof. In some embodiments of the pharmaceutical compositions or devices described herein, the dexamethasone, methylprednisolone, or prednisolone is in the form of a free base, a free acid, a salt, a prodrug, or a combination thereof. In some embodiments of the pharmaceutical compositions or devices described herein, the dexamethasone, methylprednisolone, or prednisolone is administered in the form of a phosphate or ester prodrug. In some embodiments of the pharmaceutical compositions or devices described herein, the steroid is dexamethasone phosphate or dexamethasone acetate. In some embodiments pharmaceutical compositions or devices described herein comprise dexamethasone, methylprednisolone, prednisolone, or pharmaceutically acceptable salt thereof, prodrug or combination thereof as an immediate release agent.

In some embodiments, pharmaceutical compositions or devices described herein are pharmaceutical compositions or devices wherein the dexamethasone, methylprednisolone, or prednisolone comprises multiparticulates. In some embodiments, pharmaceutical compositions or devices described herein are pharmaceutical compositions or devices wherein the dexamethasone, methylprednisolone, or prednisolone is essentially in the form of micronized particles. In some embodiments of the pharmaceutical compositions or devices described herein, the dexamethasone is in the form of micro-dexamethasone powder.

In some embodiments, pharmaceutical compositions or devices described herein further comprise an additional therapeutic agent. In some embodiments, the additional therapeutic agent is a Na/K ATPase modulator, a chemotherapeutic agent, a collagen, a gamma-globulin, an interferon, an anti-microbial agent, an antibiotic, a local acting anesthetic agent, a platelet activator factor antagonist, an otoprotectant, a nitric oxide synthase inhibitor, an anti-vertigo agent, a vasopressin antagonist, an anti-viral agent, an anti-emetic agent, an anti-TNF agent, a vasopressin receptor modulator, methotrexate, cyclophosphamide, immunosuppressants, macrolides; latanoprost, a TNF converting enzyme inhibitor, an IKK inhibitor, a glutamate receptor modulator, an anti-apoptotic agent, a neuroprotectant, thalidomide, c-jun inhibitor compound, hyaluronidase, antioxidants, IL-1 beta modulators, ERR-beta antagonist, IGF-1 modulators, Toll-like receptors, KCNQ channel modulators, neurotropin modulators, ATOH modulators or combinations thereof.

In some embodiments, pharmaceutical compositions or devices described herein are pharmaceutical compositions or devices wherein the pH of the pharmaceutical composition or device is between about 6.0 to about 7.6.

In some embodiments of the pharmaceutical compositions or devices described herein, the ratio of a polyoxyethylene-polyoxypropylene triblock copolymer of general formula E106 P70 E106 to a thickening agent is from about 40:1 to about 5:1. In some embodiments, the thickening agent is carboxymethyl cellulose, hydroxypropyl cellulose or hydroxypropyl methylcellulose.

In some embodiments, the otic disease or condition is Meniere's disease, sudden sensorineural hearing loss, noise induced hearing loss, age related hearing loss, auto immune ear disease or tinnitus.

Also provided herein is a method of treating an otic disease or condition comprising administering to an individual in need thereof an intratympanic composition or device comprising a therapeutically effective amount of dexamethasone, methylprednisolone, or prednisolone, the composition or device comprising substantially low degradation products of dexamethasone, methylprednisolone, or prednisolone, the composition or device further comprising two or more characteristics selected from:
  (i) between about 0.1% to about 10% by weight of dexamethasone, methylprednisolone, or prednisolone, or pharmaceutically acceptable prodrug or salt thereof;
  (ii) between about 16% to about 21% by weight of a polyoxyethylene-polyoxypropylene triblock copolymer of general formula E106 P70 E106;
  (iii) sterile water, q.s., buffered to provide a pH between about 5.5 and about 8.0;
  (iv) multiparticulate dexamethasone, methylprednisolone, or prednisolone;
  (v) a gelation temperature between about 19° C. to about 42° C.;
  (vi) less than about 50 colony forming units (cfu) of microbiological agents per gram of formulation, and
  (vii) less than about 5 endotoxin units (EU) per kg of body weight of a subject.

In some embodiments of the methods described herein, the dexamethasone, methylprednisolone, or prednisolone is released from the composition or devices for a period of at least 3 days. In some embodiments of the methods described herein, the dexamethasone, methylprednisolone, or prednisolone is released from the composition or device for a period of at least 5 days. In some embodiments of the methods described herein, the dexamethasone, methylprednisolone, or prednisolone is released from the composition or device for a period of at least 10 days. In some embodiments of the method described above, the dexamethasone, methylprednisolone, or prednisolone is essentially in the form of micronized particles.

In some embodiments of the methods described herein, the composition is administered across the round window. In some embodiments of the methods described herein, the otic disease or condition is Meniere's disease, sudden sensorineural hearing loss, noise induced hearing loss, age related hearing loss, auto immune ear disease or tinnitus.

DETAILED DESCRIPTION OF THE INVENTION

Figure 1:
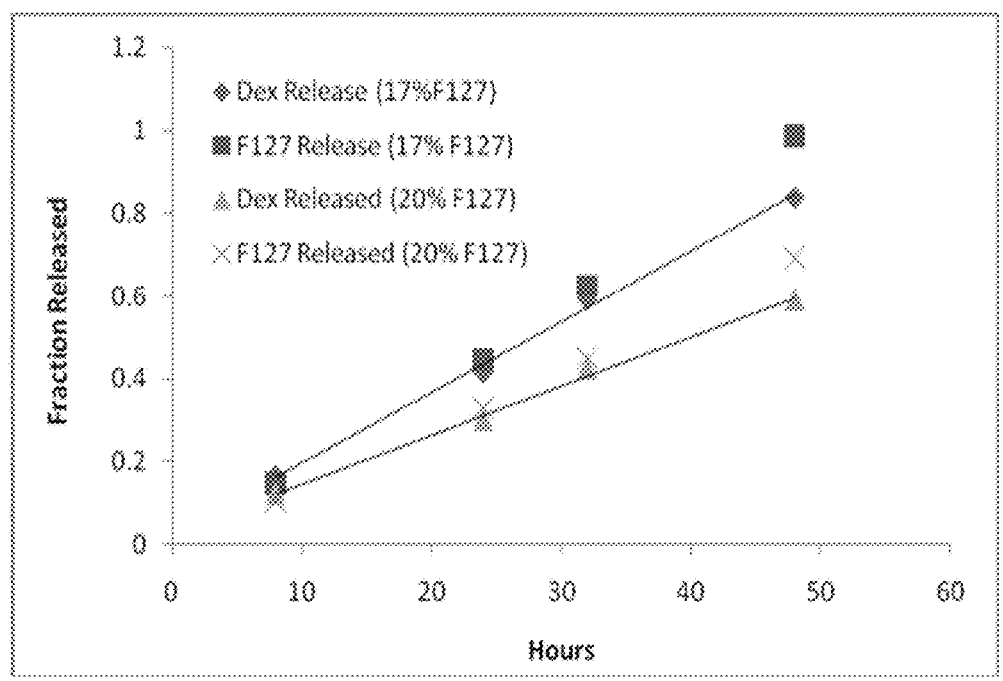
FIG. 1. illustrates in vitro release profile of Dexamethasone vs. varying concentrations of Poloxamer 407.

Provided herein are controlled release corticosteroid compositions and formulations to treat diseases of the ear, including Meniere's disease and sensineural hearing loss.

A few therapeutic products are available for the treatment of otic disorders such as AIED, however, systemic routes via oral, intravenous or intramuscular routes are currently used to deliver these therapeutic agents. Systemic drug administration may create a potential inequality in drug concentration with higher circulating levels in the serum, and lower levels in the target auris media and auris interna organ structures. As a result, fairly large amounts of drug are required to overcome this inequality in order to deliver sufficient, therapeutically effective quantities to the inner ear. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant side effects of systemic delivery, disclosed herein are methods and compositions and devices for local delivery of therapeutic agents to targeted auris structures. Access to, for example, the vestibular and cochlear apparatus will occur through the auris media including round window membrane, the oval window/stapes footplate, the annular ligament and through the otic capsule/temporal bone.

Accordingly, provided herein are controlled release corticosteroid formulations and compositions to locally treat targeted auris structures, thereby avoiding side effects as a result of systemic administration of the corticosteroid formulations and compositions. The locally applied corticosteroid formulations and compositions and devices are compatible with the targeted auris structures, and administered either directly to the desired targeted auris structure, e.g. the cochlear region, the tympanic cavity or the external ear, or administered to a structure in direct communication with areas of the auris interna, including but not limited to the round window membrane, the crista fenestrae cochleae or the oval window membrane. By specifically targeting an auris structure, adverse side effects as a result of systemic treatment are avoided. Moreover, clinical studies have shown the benefit of having long term exposure of drug to the perilymph of the cochlea, for example with improved clinical efficacy of sudden hearing loss when the therapeutic agent is given on multiple occasions. Thus, by providing a controlled release corticosteroid formulation or composition to treat otic disorders, a constant, variable and/or extended source of corticosteroid is provided to the individual or patient suffering from an otic disorder, reducing or eliminating the variability of treatment. Accordingly, one embodiment disclosed herein is to provide a formulation that enables at least one corticosteroid to be released in therapeutically effective doses either at variable or constant rates such as to ensure a continuous release of the at least one agent. In some embodiments, the corticosteroids disclosed herein are administered as an immediate release formulation or composition. In other embodiments, the steroid and/or ATPase modulator agents are administered as a sustained release formulation, released either continuously, variably or in a pulsatile manner, or variants thereof. In still other embodiments, corticosteroid formulation is administered as both an immediate release and sustained release formulation, released either continuously, variably or in a pulsatile manner, or variants thereof. The release is optionally dependent on environmental or physiological conditions, for example, the external ionic environment (see, e.g. Oros® release system, Johnson & Johnson).

In addition, localized treatment of the targeted auris structure also affords the use of previously undesired therapeutic agents, including agents with poor pK profiles, poor uptake, low systemic release and/or toxicity issues. Because of the localized targeting of the corticosteroid formulations and compositions and devices, as well as the biological blood barrier present in the auris interna, the risk of adverse effects will be reduced as a result of treatment with previously characterized toxic or ineffective corticosteroids. Accordingly, also contemplated within the scope of the embodiments herein is the use of corticosteroids in the treatment of otic disorders that have been previously rejected by practitioners because of adverse effects or ineffectiveness of the corticosteroid.

Also included within the embodiments disclosed herein is the use of additional auris-compatible agents in combination with the corticosteroid formulations and compositions and devices disclosed herein. When used, such agents assist in the treatment of hearing or equilibrium loss or dysfunction as a result of an autoimmune disorder, including vertigo, tinnitus, hearing loss, balance disorders, infections, or combinations thereof. Accordingly, agents that ameliorate or reduce the effects of vertigo, tinnitus, hearing loss, balance disorders, infections, inflammatory response or combinations thereof are also contemplated to be used in combination with the corticosteroid(s), including anti-TNF agents, anti-emetic agents, chemotherapeutic agents, including cytoxan, azathiaprine or methotrexate; treatment with collagen, gamma globulin, interferons, copaxone, central nervous system agents, local acting anesthetic agents, antibiotics, platelet-activating factor antagonists, nitric oxide synthase inhibitors and combinations thereof.

In addition, the auris-acceptable controlled-release corticosteroid formulations and treatments described herein are provided to the target ear region of the individual in need, including the inner ear, and the individual in need is additionally administered an oral dose of corticosteroid. In some embodiments, the oral dose of corticosteroid is administered prior to administration of the auris-acceptable controlled-release corticosteroid formulation, and then the oral dose is tapered off over the period of time that the auris-acceptable controlled-release corticosteroid formulation is provided. Alternatively, the oral dose of corticosteroid is administered during administration of the auris-acceptable controlled-release corticosteroid formulation, and then the oral dose is tapered off over the period of time that the auris-acceptable controlled-release corticosteroid formulation is provided. Alternatively, the oral dose of corticosteroid is administered after administration of the auris-acceptable controlled-release corticosteroid formulation has been initiated, and then the oral dose is tapered off over the period of time that the auris-acceptable controlled-release corticosteroid formulation is provided.

In addition, the corticosteroid pharmaceutical compositions or formulations or devices included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the targeted auris structure(s). Accordingly, specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, corticosteroid pharmaceutical compositions or formulations or devices disclosed herein are optionally targeted to distinct regions of the targeted auris structures, including but not limited to the tympanic cavity, vestibular bony and membranous labyrinths, cochlear bony and membranous labyrinths and other anatomical or physiological structures located within the auris interna.

Certain Definitions

The term "auris-acceptable" with respect to a formulation, composition or ingredient, as used herein, includes having no persistent detrimental effect on the auris media (or middle ear) and the auris interna (or inner ear) of the subject being treated. By "auris-pharmaceutically acceptable," as used herein, refers to a material, such as a carrier or diluent, which does not abrogate the biological activity or properties of the compound in reference to the auris media (or middle ear) and the auris interna (or inner ear), and is relatively or is reduced in toxicity to the auris media (or middle ear) and the auris interna (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

"Antioxidants" are auris-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the corticosteroids disclosed herein.

"Auris interna" refers to the inner ear, including the cochlea and the vestibular labyrinth, and the round window that connects the cochlea with the middle ear.

"Auris-bioavailability" or "Auris-interna bioavailability" or "Auris-media bioavailability" or "Auris-externa bioavailability" refers to the percentage of the administered dose of compounds disclosed herein that becomes available in the targeted auris structure of the animal or human being studied.

"Auris media" refers to the middle ear, including the tympanic cavity, auditory ossicles and oval window, which connects the middle ear with the inner ear.

"Auris externa" refers to the outer ear, including the pinna, the auditory canal, and the tympanic membrane, which connects the outer ear with the middle ear.

"Blood plasma concentration" refers to the concentration of compounds provided herein in the plasma component of blood of a subject.

"Carrier materials" are excipients that are compatible with corticosteroid(s), the targeted auris structure(s) and the release profile properties of the auris-acceptable pharmaceutical formulations. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" refers to chemical compounds that are used to dilute the corticosteroid prior to delivery and which are compatible with the targeted auris structure(s).

"Dispersing agents," and/or "viscosity modulating agents" are materials that control the diffusion and homogeneity of the corticosteroid through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronic F127, Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also be used as dispersing agents. Optional dispersing agents useful in liposomal dispersions and self-emulsifying dispersions of the corticosteroids disclosed herein are dimyristoyl phosphatidyl choline, phosphatidyl cholines (c8-c18), phosphatidylethanolamines (c8-c18), phosphatidyl glycerols (c8-c18), natural phosphatidyl choline from eggs or soy, natural phosphatidyl glycerol from eggs or soy, cholesterol and isopropyl myristate.

"Drug absorption" or "absorption" refers to the process of movement of the corticosteroid(s) from the localized site of administration, by way of example only, the round window membrane of the inner ear, and across a barrier (the round window membranes, as described below) into the auris interna or inner ear structures. The terms "co-administration" or the like, as used herein, are meant to encompass administration of the corticosteroids to a single patient, and are intended to include treatment regimens in which the corticosteroids are administered by the same or different route of administration or at the same or different time.

The terms "effective amount" or "therapeutically effective amount," as used herein, refer to a sufficient amount of the corticosteroids being administered that would be expected to relieve to some extent one or more of the symptoms of the disease or condition being treated. For example, the result of administration of the corticosteroid agents disclosed herein is reduction and/or alleviation of the signs, symptoms, or causes of AIED. For example, an "effective amount" for therapeutic uses is the amount of the corticosteroid, including a formulation as disclosed herein required to provide a decrease or amelioration in disease symptoms without undue adverse side effects. The term "therapeutically effective amount" includes, for example, a prophylactically effective amount. An "effective amount" of a corticosteroid composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended-release dosing format may differ from "an effective amount" in an immediate-release dosing format based upon pharmacokinetic and pharmacodynamic considerations.

The terms "enhance" or "enhancing" refers to an increase or prolongation of either the potency or duration of a desired effect of the corticosteroid, or a diminution of any adverse symptomotology such as localized pain that is consequent upon administration of the therapeutic agent. Thus, in regard to enhancing the effect of the corticosteroids disclosed herein, the term "enhancing" refers to the ability to increase or prolong, either in potency or duration, the effect of other therapeutic agents that are used in combination with the corticosteroids disclosed herein. An "enhancing-effective amount," as used herein, refers to an amount of corticosteroids, or other therapeutic agent, that is adequate to enhance the effect of another therapeutic agent or corticosteroids in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, AIED, or advancement of a condition in a patient necessitating treatment.

The terms "kit" and "article of manufacture" are used as synonyms.

"Pharmacodynamics" refers to the factors which determine the biologic response observed relative to the concentration of drug at the desired site within the targeted auris structure.

"Pharmacokinetics" refers to the factors which determine the attainment and maintenance of the appropriate concentration of drug at the desired site within the targeted auris structure.

In prophylactic applications, compositions containing the corticosteroids described herein are administered to a patient susceptible to or otherwise, at risk of a particular disease, disorder or condition, for example, Meniere's disease, or patients that are suffering from diseases associated with AIED, including by way of example only, Ankylosing spondylitis, Systemic Lupus Erythematosus (SLE), Sjögren's Syndrome, Cogan's disease, ulcerative colitis, Wegener's granulomatosis, inflammatory bowel disease, rheumatoid arthritis, scleroderma and Behçet's disease. Such an amount is defined to be a "prophylactically effective amount or dose." In this use, the precise amounts also depend on the patient's state of health, weight, and the like.

As used herein, a "pharmaceutical device" includes any composition described herein that, upon administration to an ear, provides a reservoir for extended release of an active agent described herein.

A "prodrug" refers to the corticosteroid that is converted into the parent drug in vivo. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Round window membrane" is the membrane in humans that covers the fenestrae cochlea (also known as the circular window, fenestrae rotunda, or round window). In humans, the thickness of round window membrane is about 70 micron.

"Solubilizers" refers to auris-acceptable compounds such as triacetin, triethylcitrate, ethyl oleate, ethyl caprylate, sodium lauryl sulfate, sodium caprate, sucrose esters, alkylglucosides, sodium doccusate, vitamin E TPGS, dimethylacetamide, N-methylpyrrolidone, N-hydroxyethylpyrrolidine, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" refers to compounds such as any antioxidation agents, buffers, acids, preservatives and the like that are compatible with the environment of the targeted auris structure. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Steady state," as used herein, is when the amount of drug administered to the targeted auris structure is equal to the amount of drug eliminated within one dosing interval resulting in a plateau or constant levels of drug exposure within the targeted structure.

As used herein, the term "subject" is used to mean an animal, preferably a mammal, including a human or non-human. The terms patient and subject may be used interchangeably.

"Surfactants" refers to compounds that are auris-acceptable, such as sodium lauryl sulfate, sodium docusate, Tween® 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Anatomy of the Ear

As shown in the illustration below, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window.

Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (more correctly, round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Diseases

Otic disorders, including auris interna, auris media and auris externa disorders, produce symptoms which include but are not limited to hearing loss, nystagmus, vertigo, tinnitus, inflammation, swelling, infection and congestion. These disorders may have many causes, such as infection, injury, inflammation, tumors and adverse response to drugs or other chemical agents. Several causes of hearing and/or equilibrium impairment or inflammation may be attributed to an autoimmune disorder and/or a cytokine-mediated inflammatory response. In one embodiment, the otic disorder is Meniere's disease. In one embodiment, the otic disorder is sensineural hearing loss. In one embodiment the otic disorder is autoimmune inner ear disease (AIED). In one embodiment, the otic disorder is Meniere's disease. In further embodiments the otic disorder is Meniere's syndrome, vestibular neuronitis, postural vertigo, Ramsay Hunt's Syndrome (herpes zoster infection), syphilis infection, drug-induced inner ear damage, auditory nerve tumors, hearing loss from excessive noise, presbycusis, otosclerosis, or temporomandibular joint disease.

The disease presented herein, included those presented below are treated using the steroid pharmaceutical compositions described herein.

Meniere's Disease

Meniere's Disease is an idiopathic condition characterized by sudden attacks of vertigo, nausea and vomiting that may last for 3 to 24 hours, and may subside gradually. Progressive hearing loss, tinnitus and a sensation of pressure in the ears accompanies the disease through time. The cause of Meniere's disease is unknown but is probably related to an imbalance of inner ear fluid homeostasis, including an increase in production or a decrease in reabsorption of inner ear fluid.

Surgical procedures that have been used to relieve symptoms include the destruction of vestibular and/or cochlear function to relieve vertigo symptoms. These procedures aim to either reduce fluid pressure in the inner ear and/or to destroy inner ear balance function. An endolymphatic shunt procedure, which relieves fluid pressure, may be placed in the inner ear to relieve symptoms of vestibular dysfunction. Other treatments include gentamicin application, which when injected into the eardrum destroys sensory hair cell function, thereby eradicating inner ear balance function. Severing of the vestibular nerve may also be employed, which while preserving hearing, may control vertigo.

A standard of care for Meniere's Disease requires an individual to follow a low salt diet. In certain instances, the low salt diet is supplemented with administration of an antibiotic. In certain instances, the low salt diet is supplemented with administration of gentamycin. In certain instances, the low salt diet is supplemented with administration of an oral steroid. In certain instances, the low salt diet is supplemented with administration of oral prednisone (25-50 mg PO/IM/PR q4-6 h).

In one set of embodiments, a patient who is being treated for Meniere's Disease using a standard of care presented above, is instead treated using the controlled-release corticosteroid auris-acceptable formulations and methods described herein. In another set of embodiments, a patient who is being treated for Meniere's Disease using a standard of care presented above, but who is refractory or unresponsive to such treatment, is instead treated using the controlled-release corticosteroid auris-acceptable formulations and methods described herein.

In some embodiments, mechanical or imaging devices are used to monitor or survey the hearing, balance or other auris disorder. For example, magnetic resonance imaging (MRI) devices are specifically contemplated within the scope of the embodiments, wherein the MRI devices (for example, 3 Tesla MRI devices) are capable of evaluating Meniere Disease progression, and subsequent treatment with the pharmaceutical formulations disclosed herein. Gadolinium-based dyes, iodine-base dyes, barium-based dyes or the like are also contemplated for use with any auris-compatible composition or device described herein and/or with any mechanical or imaging devices described herein. In certain embodiments, gadolinium hydrate is used in combination with MRI and/or any pharmaceutical composition or device described herein to evaluate disease severity (e.g., size of endolymphatic hydrops), formulation penetration into the inner ear, and/or therapeutic effectiveness of the pharmaceutical formulations/ devices in the otic diseases described herein (e.g., Meniere's disease).

Meniere's Syndrome

Meniere's Syndrome, which displays similar symptoms as Meniere's disease, is attributed as a secondary affliction to another disease process, e.g. thyroid disease or inner ear inflammation due to syphilis infection. Meniere's syndrome, thus, are secondary effects to various process that interfere with normal production or resorption of endolymph, including endocrine abnormalities, electrolyte imbalance, autoimmune dysfunction, medications, infections (e.g. parasitic infections) or hyperlipidemia. Treatment of patients afflicted with Meniere's Syndrome is similar to Meniere's Disease.

Sensorineural Hearing Loss

Sensorineural hearing loss occurs when the components of the inner ear or accompanying neural components are affected, and may contain a neural, i.e. when the auditory nerve or auditory nerve pathways in the brain are affected, or sensory component. Sensory hearing loss may be hereditary, or it may be caused by acoustic trauma (e.g., very loud noises), a viral infection, drug-induced or Meniere's disease. Neural hearing loss may occur as a result of brain tumors, infections, or various brain and nerve disorders, such as stroke. Some hereditary diseases, such as Refsum's disease (defective accumulation of branched fatty acids), may also cause neural disorders affecting hearing loss. Auditory nerve pathways may be damaged by demyelinating diseases, e.g. idiopathic inflammatory demyelinating disease (including multiple sclerosis), transverse myelitis, Devic's disease, progressive multifocal leukoencephalopathy, Guillain-Barre syndrome, chronic inflammatory demyelinating polyneuropathy and anti-MAG perpheral neuropathy.

The incidence of sudden deafness, or sensorineural hearing loss, occurs in about 1 in 5000 individuals, and may be caused by viral or bacterial infections, e.g. mumps, measles, influenza, chickenpox, cytomegalovirus, syphilis or infectious mononucleosis, or physical injury to the inner ear organ. In some cases, no cause can be identified. Tinnitus and vertigo may accompany sudden deafness, which subsides gradually. Oral corticosteroids are prescribed to treat sensorineural hearing loss. In some cases, surgical intervention may be necessary.

The formulations and methods described herein include the treatment of sensineural hearing loss, including, treatment for sudden sensineural hearing loss, including idiopathic sudden sensineural hearing loss. For SSHL, current treatment options include a high dose oral steroid 2 week treatment (4-7 day course+7-10 days taper) with either dexamethasone (4-10 mg/ml), or methyl-prednisolone (40-62.5 mg/ml). As noted herein, high doses of oral steroids are associated with undesired side effects and adverse events. Accordingly, the methods and formulations described herein, which are directed to sustained release, localized delivery of the steroids to the inner ear are expected to result in significantly less side effects than oral/systemic steroid use. In one embodiment, the ISSHL is characterized by unilateral sensorineural hearing loss with an onset over a period of less than 72 hours, where the HL is defined as being >30 dB in at least 3 contiguous test frequencies.

A standard of care for Idiopathic Sudden Sensorineural Hearing Loss (ISSHL) is treatment with high dose oral steroid. In certain instances, an individual is treated with high dose oral steroid for about two weeks. In certain instances, an individual is treated with high dose oral steroid for about two weeks followed by a tapering off of the oral steroid for about seven to about ten days. In certain instances, the oral steroid is dexamethasone (4-10 mg/ml). In certain instances, the oral steroid is methyl-prednisolone (40-62.5 mg/ml).

In one set of embodiments, a patient who is being treated for ISSHL using a standard of care presented above, is instead treated using the controlled-release corticosteroid auris-acceptable formulations and methods described herein. In another set of embodiments, a patient who is being treated for ISSHL using a standard of care presented above, but who is refractory or unresponsive to such treatment, is instead treated using the controlled-release corticosteroid auris-acceptable formulations and methods described herein.

Hearing Loss From Excessive Noise

Hearing loss may also occur from prolonged exposure to loud noises, such as loud music, heavy equipment or machinery, airplanes, gunfire or other human-based noises. The hearing loss occurs as result of destruction of hair cell receptors in the inner ear. This hearing loss is often accompanied by tinnitus. Permanent damage to hearing loss is often diagnosed.

Although there is currently no treatment for noise-induced hearing loss, several treatment regimens have been experimentally developed, including treatment with insulin-like growth factor 1 (IGF-1). Lee et al. *Otol. Neurotol.* (2007) 28:976-981).

Presbycusis

Presbycusis, or age-related hearing loss, occurs as a part of normal aging, and occurs as a result of degeneration of the receptor cells in the spiral organ of Corti in the inner ear. Other causes may also be attributed to a decrease in a number of nerve fibers in the vestibulocochlear nerve, as well as a loss of flexibility of the basilar membrane in the cochlea. There is currently no known cure for permanent hearing damage as a result of presbycusis or excessive noise.

Drug-Induced Inner Ear Damage

Damage from the administration of drugs, including certain antibiotics, diuretics (e.g. ethacrynic acid and furosemide), aspirin, aspirin-like substances (e.g. salicylates) and quinine includes, deterioration of the auris interna organ may be hastened by impaired kidney function, which results in decreased clearance of the affecting drugs and their metabolites. The drugs may affect both hearing and equilibrium, but likely affects hearing to a greater extent.

For example, neomycin, kanamycin and amikacin have a greater effect on hearing than on balance. The antibiotics viomycin, gentamicin and tobramycin affect both hearing and equilibrium. Streptomycin, another commonly administered antibiotic, induces vertigo more than loss of hearing, and can lead to Dandy's syndrome, where walking in the dark becomes difficult and induces a sensation of the environment moving with each step. Aspirin, when taken in very high doses, may also lead to temporary hearing loss and tinnitus, a condition where sound is perceived in the absence of external sound. Similarly, quinine, ethacrynic acid and furosemide can result in temporary or permanent hearing loss.

Autoimmune Inner Ear Disease

Autoimmune inner ear disease (AIED) is one of the few reversible causes of sensorineural hearing loss. It is a rare disorder appearing in both adults and children that often involves a bilateral disturbance of the audio and vestibular functions of the auris interna. In many cases, AIED occurs without systemic autoimmune symptoms, but up to one-third of patients also suffer from a systemic autoimmune illness, such as inflammatory bowel disease, rheumatoid arthritis (Murdin, L. et al (2007), Hearing difficulties are common in patients with rheumatoid arthritis, in *Clin Rheumatol*, 27(5): 637-640), Ankylosing spondylitis, Systemic Lupus Erythematosus (SLE), Sjögren's Syndrome, Cogan's disease, ulcerative colitis, Wegener's granulomatosis and scleroderma. Behçet's disease, a multisystem disease, also commonly has audiovestibular problems. There is some evidence for food-related allergies as a cause for cochlear and vestibular autoimmunity, but there is presently no agreement as to its importance in the aetiology of the disease. A classification scheme for AIED has been developed (Harris and Keithley, (2002) Autoimmune inner ear disease, in *Otorhinolaryngology Head and Neck Surgery.* 91, 18-32).

Treatment with corticosteroid relieves AIED symptoms. Oral administration of the corticosteroid prednisone (60 mg/day for four (4) weeks) showed marked improvement in pure-tone and speech audiometric results. Mediation of the corticosteroid affect occurs through either corticosteroid receptors or mineralocorticoid receptors.

Inflammatory Disorders

Inflammatory disorders of the ear include and are not limited to Otitis media, otitis externa, mastoiditis, Bullous myringitis, Eustachian tubal catarrh, or Eustachian salpingitis, Labyrinthitis or the like. Otitis media (OM), which includes acute otitis media (AOM), otitis media with effusion (OME) and chronic otitis media as examples, is a condition affecting both adults and children. OM susceptibility is multifactorial and complex, including environmental, microbial and host factors. In some instances, increases in cytokine production, including inflammatory cytokines, e.g., interleukins and TNF, have been observed in the effluent media of individuals afflicted with OM. Treatment with antiinflammatory steroids relieves the symptoms of inflammatory disorders of the ear (e.g., otitis media, eustachian tube catarrh or the like). In some instances, bacterial infection accounts for inflammatory disorders (e.g., OM). In some instances, administration of an antibiotic in combination with an anti-inflammatory corticosteroid relieves the symptoms of OM.

Pharmaceutical Agents

Provided herein are pharmaceutical compositions or formulations or devices comprising steroids that ameliorate or lessen otic disorders, including Meniere's disease, sensineural hearing loss, and/or inflammatory disorders and their attendant symptoms, which include but are not limited to hearing loss, nystagmus, vertigo, tinnitus, inflammation, swelling, infection and congestion. Otic disorders, including AIED or Meniere's disease and/or inflammatory disorders, have causes and symptoms that are responsive to the pharmaceutical agents disclosed herein, or other pharmaceutical agents. In specific embodiments, the steroids are corticosteroids, including glucocorticosteroids and mineral corticosteroids. Any corticosteroid described herein (including free acid, free base, free alcohol, salt, prodrug, or any combination thereof) is compatible with the pharmaceutical compositions or devices described herein. Corticosteroids which are not specifically disclosed herein but which are useful for the amelioration or eradication of otic disorders are expressly included and intended within the scope of the embodiments presented.

Moreover, pharmaceutical agents which have been previously shown to be toxic, harmful or non-effective during systemic or localized application in other organ systems, for example through toxic metabolites formed after hepatic processing, toxicity of the drug in particular organs, tissues or systems, through high levels needed to achieve efficacy, through the inability to be released through systemic pathways or through poor pK characteristics, are useful in some embodiments herein. For example, side effects of dexamethasone include: sodium retention, excessive water retention, congestive heart failure in susceptible patients, hypertension, muscle weakness, muscle atrophy, osteoporosis, tendon rupture, peptic ulcer, ulcerative esophagitis, thinning of the skin, cutaneous reaction, impaired wound healing, convulsions, vertigo, headache, psychological disorders, Cushing's syndrome, delayed growth in children, diabetes, hirsutism, cataracts, glaucoma, weight gain, increased appetite, and nausea. Pharmaceutical agents (e.g., corticosteroids) which have limited or no systemic release, systemic toxicity, poor pK characteristics or combinations thereof are explicitly contemplated within the scope of the embodiments disclosed herein.

The corticosteroid formulations disclosed herein are optionally targeted directly to otic structures where treatment is needed; for example, one embodiment contemplated is the direct application of the corticosteroid formulations disclosed herein onto the round window membrane or the crista fenestrae cochlea of the auris interna, allowing direct access and treatment of the auris interna, or inner ear components. In other embodiments, the corticosteroid formulation disclosed herein is applied directly to the oval window. In yet other embodiments, direct access is obtained through microinjection directly into the auris interna, for example, through cochlear microperfusion. Such embodiments also optionally comprise a drug delivery device, wherein the drug delivery device delivers the corticosteroid formulations through use of a needle and syringe, a pump, a microinjection device, an in situ forming spongy material or any combination thereof. In still other embodiments, application of the corticosteroid formulation is targeted to the auris media through piercing of the intratympanic membrane and application of corticosteroid formulation directly to the auris media structures affected, including the walls of the tympanic cavity or auditory ossicles. By doing so, the corticosteroid formulations disclosed herein are confined to the targeted auris media structure, and will not be lost, for example, through diffusion or leakage through the eustachian tube or pierced tympanic membrane.

Corticosteroids/Anti-Inflammatory Steroids

The corticosteroids are characterized by mineralocorticoid and glucocorticoid effects, depending on the pharmacology of the agent. Mineralocorticoids are characterized by their similarity to aldosterone and their influence on electrolyte levels and water balance. The glucocorticoids, such as the endogenous glucocorticoid cortisol, control metabolism and are anti-inflammatory by preventing cytokine release. Many agents possess a degree of both mineralocorticoid and glucocorticoid activity. The relative potency and activity of several synthetic glucocorticoids are shown in the table below.

| Steroid | Glucocorticoid potency | Mineralocorticoid potency |
|---|---|---|
| cortisol | 1 | 0.054 |
| prednisone | 4 | 0.002 |
| prednisolone | 1.7 | 0.013 |
| dexamethasone | 21 | 0.0094 |
| betamethasone | 45 | 0.0038 |
| triamcinolone | 0.35 | 0.0002 |
| prednylidene | 182 | 0.0011 |
| aldosterone | 0.07 | 1.0 |

Systemic glucocorticoid treatment is the current therapy in use for autoimmune hearing loss. Typical treatment duration lasts for months and the side effects from systemic therapy can be substantial. For dexamethasone the side effects include: sodium retention, excessive water retention, congestive heart failure in susceptible patients, hypertension, muscle weakness, muscle atrophy, osteoporosis, tendon rupture, peptic ulcer, ulcerative esophagitis, thinning of the skin, cutaneous reaction, impaired wound healing, convulsions, vertigo, headache, psychological disorders, Cushing's syndrome, delayed growth in children, diabetes, hirsutism, cataracts, glaucoma, weight gain, increased appetite, and nausea. One advantage of the use of a formulation described herein is the greatly reduced systemic exposure to anti-inflammatory glucocorticoid steroids.

Prednisolone is a corticosteroid drug with predominantly glucocorticoid and low mineralocorticoid activity. It has about 4-5 times the potency of endogenous cortisol. It is an active metabolite of orally administered prednisone. Dexamethasone is a corticosteroid drug with glucocorticoid activity. It has about 25-30 times the potency of endogenous cortisol. Dexamethasone sodium phosphate is a water soluble phosphate ester prodrug of dexamethasone. A method for the analytical determination of dexamethasone phosphate in cochlear perilymph fluid has been published (Liu et al, J. of Chromatography B (2004), 805(2):255-60). Triamcinolone is a synthetic glucocorticoid drug which has been administered orally, by injection, inhalation, or as a topical cream or ointment. Triamcinolone acetonide is a more potent analog. Triamcinolone hexacetonide is the pivolyl ester of triamcinolone acetonide. Beclomethasone dipropionate, also referred to as beclometasone, is a very potent glucocorticoid drug. Clobetasol is a very potent corticosteroid used in topical formulations. It has anti-inflammatory, antipruritic, vasoconstrictive, and immune-modulating properties.

In one embodiment, the active pharmaceutical ingredient of the formulation described herein is prednisolone. In another embodiment the active pharmaceutical ingredient of the formulation described herein is dexamethasone. In another embodiment the active pharmaceutical ingredient of the formulation described herein is dexamethasone phosphate. In an additional embodiment, the active pharmaceutical ingredient of the formulation described herein is beclomethasone. In an additional embodiment, the active pharmaceutical ingredient of the formulation described herein is betamethasone. In an additional embodiment, the active pharmaceutical ingredient of the formulation described herein is triamcinolone. In an additional embodiment, the active pharmaceutical ingredient of the formulation described herein is triamcinolone acetonide. In an additional embodiment, the active pharmaceutical ingredient of the formulation described herein is clobetasol.

In an additional embodiment, the active pharmaceutical ingredient of the formulation described herein is a phosphate prodrug of a glucocorticoid steroid. In an additional embodiment, the active pharmaceutical ingredient of the formulation described herein is an ester prodrug of a glucocorticoid steroid. In some embodiments, the active pharmaceutical ingredient of the formulations described herein is selected from 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, or triamcinolone hexacetonide, or phosphate prodrug or ester prodrug thereof.

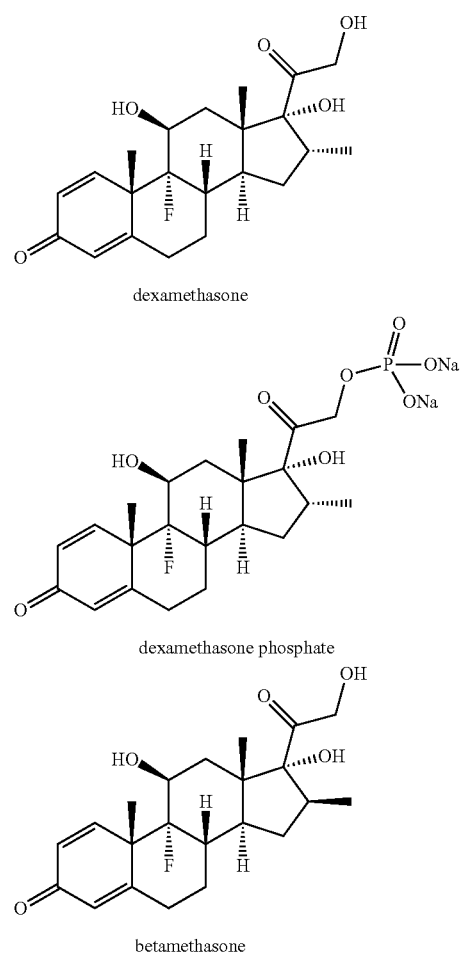

dexamethasone dexamethasone phosphate betamethasone

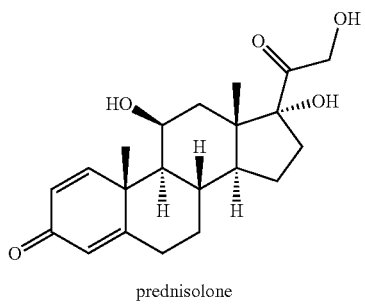
prednisolone

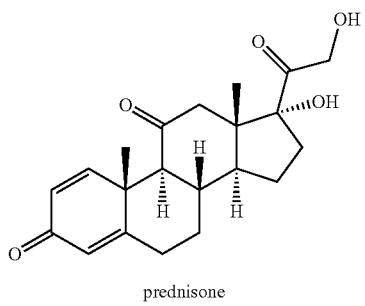
prednisone

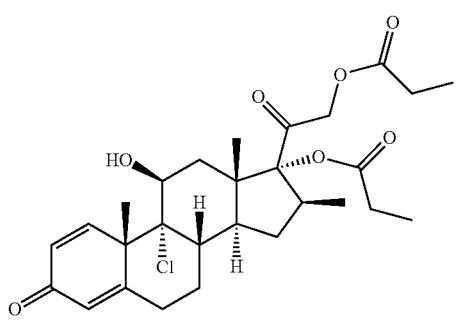
beclomethasone dipropionate

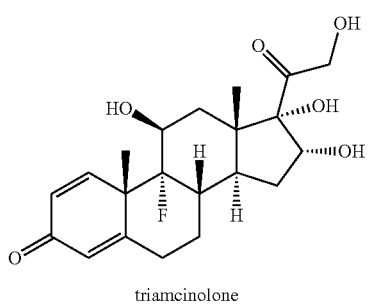
triamcinolone

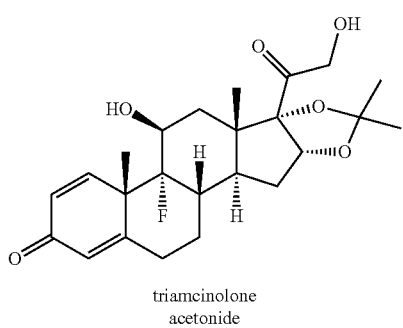
triamcinolone acetonide

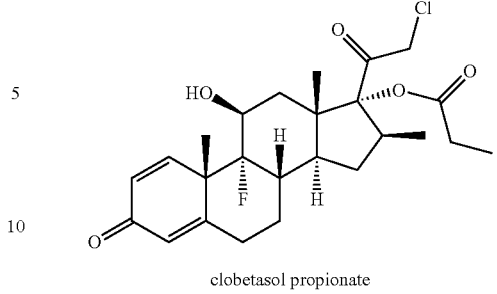
clobetasol propionate

In some embodiments, the formulations described herein have a concentration of active pharmaceutical ingredient between about 0.01% to about 20%, between about 0.01% to about 10%, between about 0.01% to about 8%, between about 0.05 to 6%, between about 0.1 to 5%, between about 0.2 to about 3%, or between about 0.1 to about 2% of the active ingredient, or pharmaceutically acceptable prodrug or salt thereof, by weight of the formulation. In some embodiments, the formulations described herein have a concentration of active pharmaceutical ingredient, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the formulation.

In some embodiments, the formulations described herein further comprise an antibiotic and are useful in the treatment of an otic disease or condition described herein. Antibiotics include and are not limited to amikacin, gentamicin, kanamycin, neomycin, netilmicin, streptomycin, tobramycin, paromomycin, geldanamycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanimilimde, sulfasalazine, sulfisoxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin, tinidazole, AL-15469A (Alcon Research), AL-38905 (Alcon Research) or the like and combinations thereof.

General Methods of Sterilization

Provided herein are otic compositions that ameliorate or lessen otic disorders described herein. Further provided herein are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U.S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave. In some embodiments, the formulations described herein comprise micronized pharmaceutical agents (e.g., corticosteroids, (e.g., micro-dexamethasone)) that are sterilized by dry heating, e.g., heating for about 7-11 hours at internal powder temperatures of 130-140° C., or for 1-2 hours at internal temperatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C.: Health Industry Manufacturers Association, 1981) and involve challenging the membrane filter with a known quantity (ca. $10^7/cm^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 µm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size. In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., dexamethasone) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, or of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In certain embodiments, the active ingredients are dissolved in a suitable vehicle (e.g. a buffer) and sterilized separately (e.g. by heat treatment, filtration, gamma radiation). In some instances, the active ingredients are sterilized separately in a dry state. In some instances, the active ingredients are sterilized as a suspension or as a colloidal suspension. The remaining excipients (e.g., fluid gel components present in auris formulations) are sterilized in a separate step by a suitable method (e.g. filtration and/or irradiation of a cooled mixture of excipients); the two solutions that are separately sterilized are then mixed aseptically to provide a final auris formulation. In some instances, the final aseptic mixing is performed just prior to administration of a formulation described herein.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the formulation. In some instances, sterilization of an auris formulation by filtration through membranes (e.g., 0.2 µM membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable sterility levels are based on applicable standards that define therapeutically acceptable otic compositions, including but not limited to United States Pharmacopeia Chapters <1111> et seq. For example, acceptable sterility levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable sterility levels for formulations include less than 10 cfu/mL, less that 50 cfu/mL, less than 500 cfu/mL or less than 1000 cfu/mL microbial agents. In addition, acceptable sterility levels include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic formulations described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The sterility is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation or device has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions or devices described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation or device has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP) <71> Sterility Tests (23rd edition, 1995). The rabbit pyrogen test and the *Limulus amebocyte* lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the *Limulus amebocyte* lysate test (Taktak et al, J. Pharm. Pharmacol. (1990), 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

pH and Practical Osmolarity

As used herein, "practical osmolarity" means the osmolarity of a formulation that is measured by including the active agent and all excipients except the gelling and/or the thickening agent (e.g., polyoxyethylene-polyoxypropylene copolymers, carboxymethylcellulose or the like). The practical osmolarity of a formulation described herein is measured by any suitable method, e.g., a freezing point depression method as described in Viegas et. al., *Int. J. Pharm.*, 1998, 160, 157-162. In some instances, the practical osmolarity of a composition described herein is measured by vapor pressure osmometry (e.g., vapor pressure depression method) that allows for determination of the osmolarity of a composition at higher temperatures. In some instances, vapor pressure depression method allows for determination of the osmolarity of a formulation comprising a gelling agent (e.g., a thermoreversible polymer) at a higher temperature wherein the gelling agent is in the form of a gel. The practical osmolality of an otic formulation described herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, the osmolarity at a target site of action (e.g., the perilymph) is about the same as the delivered osmolarity (i.e., osmolarity of materials that cross or penetrate the round window membrane) of any formulation described herein. In some embodiments, the formulations described herein have a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic formulation described herein is formulated to provide an ionic balance that is compatible with inner ear fluids (e.g., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 5.5 to 9.0. In specific embodiments, the pH of a composition described herein is adjusted to a perilymph-suitable pH range of about 5.5 to about 9.0. In some embodiments, the pH of a composition described herein is adjusted to a perilymph-suitable range of about 5.5 to about 8.0, about 6 to about 8.0 or about 6.6 to about 8.0. In some embodiments, the pH of a composition described herein is adjusted to a perilymph-suitable pH range of about 7.0-7.6.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, any gel formulation described herein has a pH that allows for sterilization (e.g., by filtration or aseptic mixing or heat treatment and/or autoclaving (e.g., terminal sterilization)) of a gel formulation without degradation of the pharmaceutical agent (e.g., steroid) or the polymers comprising the gel. In order to reduce hydrolysis and/or degradation of the otic agent and/or the gel polymer during sterilization, the buffer pH is designed to maintain pH of the formulation in the 7-8 range during the process of sterilization (e.g., high temperature autoclaving).

In specific embodiments, any gel formulation described herein has a pH that allows for terminal sterilization (e.g., by heat treatment and/or autoclaving) of a gel formulation without degradation of the pharmaceutical agent (e.g., corticosteroid) or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately $-0.03/°$ C. and $pK_a$ of PBS increases as temperature increases at approximately $0.003/°$ C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. P407, CMC) as described herein.

In some embodiments, a formulation pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g., by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g., by filtration or aseptic mixing or heat treatment and/or autoclaving (e.g., terminal sterilization)) of any composition described herein.

In some embodiments, the formulations have a pH as described herein, and include a thickening agent (e.g., a viscosity enhancing agent) such as, by way of non-limiting example, a cellulose based thickening agent described herein. In some instances, the addition of a secondary polymer (e.g., a thickening agent) and a pH of formulation as described herein, allows for sterilization of a formulation described herein without any substantial degradation of the otic agent and/or the polymer components in the otic formulation. In some embodiments, the ratio of a thermoreversible poloxamer to a thickening agent in a formulation that has a pH as described herein, is about 40:1, about 35:1, about 30:1, about 25:1, about 20:1, about 15:1 about 10:1, or about 5:1. For example, in certain embodiments, a sustained and/or extended release formulation described herein comprises a combination of poloxamer 407 (pluronic F127) and carboxymethylcellulose (CMC) in a ratio of about 40:1, about 35:1, about 30:1, about 25:1, about 20:1, about 15:1, about 10:1 or about 5:1. In some embodiments, the amount of thermoreversible polymer in any formulation described herein is about 10%, about 15%, about 20%, about 25%, about 30%, about 35% or about 40% of the total weight of the formulation. In some embodiments, the amount of thermoreversible polymer in any formulation described herein is about 14%, about 15%, about 16%, about 17%, about 18%, about 19%, about 20%, about 21%, about 22%, about 23%, about 24% or about 25% of the total weight of the formulation. In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In certain embodiments, tonicity agents are added to the formulations described herein in an amount as to provide a practical osmolality of an otic formulation of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In some embodiments, the deliverable osmolarity of any formulation described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L (osmolality of about 250 to about 320 mOsm/kg $H_2O$); and preferably about 270 to about 320 mOsm/L (osmolality of about 270 to about 320 mOsm/kg $H_2O$). In specific embodiments, the deliverable osmolarity/osmolality of the formulations (i.e., the osmolarity/osmolality of the formulation in the absence of gelling or thickening agents (e.g., thermoreversible gel polymers)) is adjusted, for example, by the use of appropriate salt concentrations (e.g., concentration of potassium or sodium salts) or the use of tonicity agents which renders the formulations endolymph-compatible and/or perilymph-compatible (i.e. isotonic with the endolymph and/or perilymph) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer)) is a reliable measure and is measured by any suitable method (e.g., freezing point depression method, vapor depression method). In some instances, the formulations described herein provide a deliverable osmolarity (e.g., at a target site (e.g., perilymph)) that causes minimal disturbance to the environment of the inner ear and causes minimum discomfort (e.g., vertigo and/or nausea) to a mammal upon administration.

In some embodiments, any formulation described herein is isotonic with the perilymph and/or endolymph. Isotonic formulations are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the formulations described herein have a pH and/or practical osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations described herein have a pH and/or practical osmolarity as described herein, and have a concentration of active pharmaceutical ingredient between about 0.1-about 20%, between about 0.1-about 10%, between about 0.1-about 7.5%, between about 0.1-6%, between about 0.1-5%, between about 0.2-about 3%, between about 0.1-about 2% of the active ingredient by weight of the formulation. In some embodiments, the formulations described herein have a pH and/or practical osmolarity as described herein, and have a concentration of active pharmaceutical ingredient between about 0.1-about 70 mg/mL, between about 1 mg-about 70 mg/mL, between about 1 mg-about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some embodiments, any formulation described herein comprises multiparticulates, i.e., a plurality of particle sizes (e.g., micronized particles, nano-sized particles, non-sized particles, colloidal particles); i.e., the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 µm to about 500 µm. In some embodiments, the average diameter of particles in a micronized solid is from about 1 µm to about 200 µm. In some embodiments, the average diameter of particles in a micronized solid is from about 2 µm to about 100 µm. In some embodiments, the average diameter of particles in a micronized solid is from about 3 µm to about 50 µm. In some embodiments, a particulate micronized solid comprises particle sizes of less than about 5 microns, less than about 20 microns and/or less than about 100 microns. In some embodiments, the use of particulates (e.g., micronized particles) of corticosteroid allows for extended and/or sustained release of the corticosteroid from any formulation described herein compared to a formulation comprising non-multiparticulate (e.g., non-micronized) corticosteroid. In some instances, formulations containing multiparticulate (e.g. micronized) corticosteroid are ejected from a 1 mL syringe adapted with a 27 G needle without any plugging or clogging.

In some instances, any particle in any formulation described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles. In some embodiments, formulations described herein comprise therapeutic agent particles wherein the therapeutic agent is a free base, or a salt, or a prodrug of a therapeutic agent, or any combination thereof.

In some embodiments, a formulation described herein comprises one or more corticosteroids wherein the corticosteroid comprises nanoparticulates. In some embodiments, a formulation described herein comprises corticosteroid beads (e.g., dexamethasone beads) that are optionally coated with controlled release excipients. In some embodiments, a formulation described herein comprises a corticosteroid that is granulated and/or reduced in size and coated with controlled release excipients; the granulated coated corticosteroid particulates are then optionally micronized and/or formulated in any of the compositions described herein.

In some instances, a combination of a corticosteroid as a free acid or free base and a salt of the corticosteroid is used to prepare pulsed release otic agent formulations using the procedures described herein. In some formulations, a combination of a micronized corticosteroid (and/or salt or prodrug thereof) and coated particles (e.g., nanoparticles, liposomes, microspheres) is used to prepare pulsed release otic agent formulations using any procedure described herein. Alternatively, a pulsed release profile is achieved by solubilizing up to 20% of the delivered dose of the corticosteroid (e.g., micronized corticosteroid, free alcohol, free acid or salt or prodrug thereof; multiparticulate corticosteroid, free alcohol, free acid or salt or prodrug thereof) with the aid of cyclodextrins, surfactants (e.g., poloxamers (407, 338, 188), tween (80, 60, 20, 81), PEG-hydrogenated castor oil, cosolvents like N-methyl-2-Pyrrolidone or the like and preparing pulsed release formulations using any procedure described herein.

In specific embodiments, any auris-compatible formulation described herein comprises one or more micronized pharmaceutical agents (e.g., steroids). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises a corticosteroid as a free acid, a free base, a salt, a prodrug or any combination thereof. In certain embodiments, a pharmaceutical composition described herein comprises dexamethasone, methylprednisolone or prednisolone as a micronized powder. In certain embodiments, a pharmaceutical composition described herein comprises dexamethasone in the form of a micro-dexamethasone powder.

The multiparticulates and/or micronized corticosteroids described herein are delivered to an auris structure (e.g., inner ear) by means of any type of matrix including solid, liquid or gel matrices. In some embodiments, the multiparticulates and/or micronized corticosteroids described herein are delivered to an auris structure (e.g., inner ear) by means of any type of matrix including solid, liquid or gel matrices via intratympanic injection.

Pharmaceutical Formulations

Provided herein are pharmaceutical compositions or devices that include at least one corticosteroid and a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutic substances.

In some embodiments, the compositions or devices described herein include a dye to help enhance the visualization of the gel when applied. In some embodiments, dyes that are compatible with the auris-acceptable compositions or devices described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g., FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like. Gadolinium-based MRI dyes, iodine-base dyes, barium-based dyes or the like are also contemplated for use with any otic formulation described herein. Other dyes that are compatible with any formulation or composition described herein are listed in the Sigma-Aldrich catalog under dyes (which is included herein by reference for such disclosure).

Any pharmaceutical composition or device described herein is administered by locating the composition or device in contact with the crista fenestrae cochlea, the round window, the tympanic cavity, the tympanic membrane, the auris media or the auris externa.

In one specific embodiment of the auris-acceptable controlled release corticosteroid pharmaceutical formulations described herein, the corticosteroid is provided in a gel matrix, also referred to herein as "auris acceptable gel formulations," "auris interna-acceptable gel formulations," "auris media-acceptable gel formulations," "auris externa-acceptable gel formulations", "auris gel formulations" or variations thereof. All of the components of the gel formulation must be compatible with the targeted auris structure. Further, the gel formulations provide controlled release of the corticosteroid to the desired site within the targeted auris structure; in some embodiments, the gel formulation also has an immediate or rapid release component for delivery of the corticosteroid to the desired target site. In other embodiments, the gel formulation has a sustained release component for delivery of the corticosteroid. In some embodiments, the gel formulation comprises a multiparticulate (e.g., micronized) corticosteroid. In some embodiments, the auris gel formulations are biodegradable. In other embodiments, the auris gel formulations include a mucoadhesive excipient to allow adhesion to the external mucous layer of the round window membrane. In yet other embodiments, the auris gel formulations include a penetration enhancer excipient; in further embodiments, the auris gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the auris gel formulation contains a viscosity enhancing agent sufficient to provide a viscosity of between about 50,0000 and 1,000,000 centipoise.

In further or alternative embodiments, the auris gel formulations are capable of being administered on or near the round window membrane via intratympanic injection. In other embodiments, the auris gel formulations are administered on or near the round window or the crista fenestrae cochleae through entry via a post-auricular incision and surgical manipulation into or near the round window or the crista fenestrae cochleae area. Alternatively, the auris gel formulation is applied via syringe and needle, wherein the needle is inserted through the tympanic membrane and guided to the area of the round window or crista fenestrae cochleae. The auris gel formulations are then deposited on or near the round window or crista fenestrae cochleae for localized treatment of autoimmune otic disorders. In other embodiments, the auris gel formulations are applied via microcathethers implanted into the patient, and in yet further embodiments the formulations are administered via a pump device onto or near the round window membrane. In still further embodiments, the auris gel formulations are applied at or near the round window membrane via a microinjection device. In yet other embodiments, the auris gel formulations are applied in the tympanic cavity. In some embodiments, the auris gel formulations are applied on the tympanic membrane. In still other embodiments, the auris gel formulations are applied onto or in the auditory canal.

In further specific embodiments, any pharmaceutical composition or device described herein comprises a multiparticulate corticosteroid in a liquid matrix (e.g., a liquid composition for intratympanic injection, or otic drops). In certain embodiments, any pharmaceutical composition described herein comprises a multiparticulate corticosteroid in a solid matrix.

Controlled Release Formulations

In general, controlled release drug formulations impart control over the release of drug with respect to site of release and time of release within the body. As discussed herein, controlled release refers to immediate release, delayed release, sustained release, extended release, variable release, pulsatile release and bi-modal release. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

Accordingly, one aspect of the embodiments disclosed herein is to provide a controlled release corticosteroid auris-acceptable composition or device for the treatment of autoimmune disorders and/or inflammatory disorders. The controlled release aspect of the compositions and/or formulations and/or devices disclosed herein is imparted through a variety of agents, including but not limited to excipients, agents or materials that are acceptable for use in the auris interna or other otic structure.

Auris-Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25°

C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. In one embodiment, administration of any formulation described herein at about body temperature reduces or inhibits vertigo associated with intratympanic administration of otic formulations. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

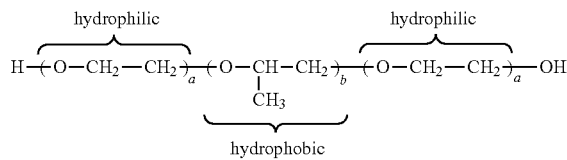

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly (orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The corticosteroid and various additives such as buffers, salts, and preservatives are subsequently added and dissolved. In some instances the corticosteroid and/or other pharmaceutically active agent is suspended if it is insoluble in water. The pH is modulated by the addition of appropriate buffering agents. round window membrane mucoadhesive characteristics are optionally imparted to a thermoreversible gel by incorporation of round window membrane mucoadhesive carbomers, such as Carbopol® 934P, to the composition (Majithiya et al, AAPS PharmSciTech (2006), 7(3), p. E1; EP0551626, both of which is incorporated herein by reference for such disclosure).

In one embodiment are auris-acceptable pharmaceutical gel formulations which do not require the use of an added viscosity enhancing agent. Such gel formulations incorporate at least one pharmaceutically acceptable buffer. In one aspect is a gel formulation comprising an corticosteroid and a pharmaceutically acceptable buffer. In another embodiment, the pharmaceutically acceptable excipient or carrier is a gelling agent.

In other embodiments, useful corticosteroid auris-acceptable pharmaceutical formulations also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the auris media or auris interna's natural buffering system, or does not interfere with the natural pH of the endolymph or perilymph: depending on where in the cochlea the corticosteroid formulation is targeted. In some embodiments, from about 10 μM to about 200 mM concentration of a buffer is present in the gel formulation. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris(hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are controlled release formulations or devices comprising a corticosteroid and a viscosity enhancing agent. Suitable viscosity-enhancing agents include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the auris-acceptable viscosity agent include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the corticosteroids disclosed herein acts as a controlled release formulation, restricting the diffusion of the corticosteroids from the formulation. Moreover, the combination of carboxymethylated chitosan and alginate is optionally used to assist in increasing the permeability of the corticosteroids through the round window membrane.

In some embodiments is an enhanced viscosity formulation, comprising from about 0.1 mM and about 100 mM of a corticosteroid, a pharmaceutically acceptable viscosity agent, and water for injection, the concentration of the viscosity agent in the water being sufficient to provide a enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the corticosteroid. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the corticosteroid.

In some embodiments, the viscosity of the gel formulations presented herein are measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity auris-acceptable formulation comprises at least one corticosteroid and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, other gel formulations are useful depending upon the particular corticosteroid, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the corticosteroid formulations described herein. In some embodiments, auris-acceptable gels include, but are not limited to, alginate hydrogels SAF®-Gel (ConvaTec, Princeton, N.J.), Duoderm® Hydroactive Gel (ConvaTec), Nu-Gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in auris-acceptable formulations disclosed and described herein.

In some formulations developed for administration to a mammal, and for compositions formulated for human administration, the auris-acceptable gel comprises substantially all of the weight of the composition. In other embodiments, the auris-acceptable gel comprises as much as about 98% or about 99% of the composition by weight. This is desirous when a substantially non-fluid, or substantially viscous formulation is needed. In a further embodiment, when slightly less viscous, or slightly more fluid auris-acceptable pharmaceutical gel formulations are desired, the biocompatible gel portion of the formulation comprises at least about 50% by weight, at least about 60% by weight, at least about 70% by weight, or even at least about 80% by weight or 90% by weight of the compound. All intermediate integers within these ranges are contemplated to fall within the scope of this disclosure, and in some alternative embodiments, even more fluid (and consequently less viscous) auris-acceptable gel compositions are formulated, such as for example, those in which the gel or matrix component of the mixture comprises not more than about 50% by weight, not more than about 40% by weight, not more than about 30% by weight, or even those than comprise not more than about 15% or about 20% by weight of the composition.

Round Window Membrane Mucoadhesives

Also contemplated within the scope of the embodiments is the addition of a round window membrane mucoadhesive with the corticosteroid formulations and compositions and devices disclosed herein. The term 'mucoadhesion' is used for materials that bind to the mucin layer of a biological membrane, such as the external membrane of the 3-layered round window membrane. To serve as round window membrane mucoadhesive polymers, the polymers possess some general physiochemical features such as predominantly anionic hydrophilicity with numerous hydrogen bond forming groups, suitable surface property for wetting mucus/mucosal tissue surfaces or sufficient flexibility to penetrate the mucus network.

Round window membrane mucoadhesive agents that are used with the auris-acceptable formulations include, but are not limited to, at least one soluble polyvinylpyrrolidone polymer (PVP); a water-swellable, but water-insoluble, fibrous, cross-linked carboxy-functional polymer; a crosslinked poly (acrylic acid) (e.g. Carbopol® 947P); a carbomer homopolymer; a carbomer copolymer; a hydrophilic polysaccharide gum, maltodextrin, a cross-linked alginate gum gel, a water-dispersible polycarboxylated vinyl polymer, at least two particulate components selected from the group consisting of titanium dioxide, silicon dioxide, and clay, or a mixture thereof. The round window membrane mucoadhesive agent is optionally used in combination with an auris-acceptable viscosity increasing excipient, or used alone to increase the interaction of the composition with the mucosal layer target otic component. In one non-limiting example, the mucoadhesive agent is maltodextrin and/or an alginate gum. When used, the round window membrane mucoadhesive character imparted to the composition is at a level that is sufficient to deliver an effective amount of the corticosteroid composition to, for example, the mucosal layer of round window membrane or the crista fenestrae cochleae in an amount that coats the mucosal membrane, and thereafter deliver the composition to the affected areas, including by way of example only, the vestibular and/or cochlear structures of the auris interna. One method for determining sufficient mucoadhesiveness includes monitoring changes in the interaction of the composition with a mucosal layer, including but not limited to measuring changes in residence or retention time of the composition in the absence and presence of the mucoadhesive excipient.

In one non-limiting example, the round window membrane mucoadhesive agent is maltodextrin. Maltodextrin is a carbohydrate produced by the hydrolysis of starch that is optionally derived from corn, potato, wheat or other plant products. Maltodextrin is optionally used either alone or in combination with other round window membrane mucoadhesive agents to impart mucoadhesive characteristics on the compositions disclosed herein. In one embodiment, a combination of maltodextrin and a carbopol polymer are used to increase the round window membrane mucoadhesive characteristics of the compositions or devices disclosed herein.

In another embodiment, the round window membrane mucoadhesive agent is an alkyl-glycoside and/or a saccharide alkyl ester. As used herein, an "alkyl-glycoside" means a compound comprising any hydrophilic saccharide (e.g. sucrose, maltose, or glucose) linked to a hydrophobic alkyl. In some embodiments, the round window membrane mucoadhesive agent is an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the round window membrane mucoadhesive agent is a hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose n-amino-alkyl ethers and long chain aliphatic carbonic acid amides of sucrose β-amino-alkyl ethers. In some embodiments, the round window membrane mucoadhesive agent is an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the round window membrane mucoadhesive agent is an alkyl-glycoside wherein the alkyl glycoside is dodecylmaltoside, tridecylmaltoside, and tetradecylmaltoside. In some embodiments, the auris acceptable penetration enhancer is a surfactant comprising an alkyl-glycoside wherein the alkyl glycoside is tetradecyl-β-D-maltodise. In some embodiments, the round window membrane mucoadhesive agent is an alkyl-glycoside wherein the alkyl-glycoside is a disaccharide with at least one glucose. In some embodiments, the auris acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the round window membrane mucoadhesive agent is an alkyl-glycoside wherein the alkyl-glycoside has a critical miscelle concentration (CMC) of less than about 1 mM in pure water or in aqueous solutions. In some embodiments, the round window membrane mucoadhesive agent is an alkyl-glycoside wherein an oxygen atom within the alkyl-glycoside is substituted with a sulfur atom. In some embodiments, the round window membrane mucoadhesive agent is an alkyl-glycoside wherein the alkylglycoside is the β anomer. In some embodiments, the round window membrane mucoadhesive agent is an alkyl-glycoside wherein the alkylglycoside comprises 90%, 91%, 92%, 93%, 94%; 95%, 96%, 97%, 98%, 99%, 99.1%, 99.5%, or 99.9% of the β anomer.

Auris-Acceptable Cyclodextrin and Other Stabilizing Formulations

In a specific embodiment, the auris-acceptable formulations alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

R = H
β-cyclodextrin
R = CH$_2$CH(OH)CH$_3$
hydroxypropyl β-cyclodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the auris-acceptable corticosteroids within the formulations described herein. In other embodiments, cyclodextrins in addition serve as controlled release excipients within the formulations described herein.

By way of example only, cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, formulation considerations, or other factors associated with the therapeutically active agent, or a salt or prodrug thereof, or with the properties of other excipients in the composition. Thus, in certain circumstances, the concentration or amount of cyclodextrin used in accordance with the compositions and methods disclosed herein will vary, depending on the need. When used, the amount of cyclodextrins needed to increase solubility of the corticosteroid and/or function as a controlled release excipient in any of the formulations described herein is selected using the principles, examples, and teachings described herein.

Other stabilizers that are useful in the auris-acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation (e.g., oleic acid, waxes), or improves the mixing of various components in the formulation (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In other embodiments, stabilizers are present in sufficient amounts to inhibit the degradation of the corticosteroid. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Additional useful corticosteroid auris-acceptable formulations include one or more anti-aggregation additives to enhance stability of corticosteroid formulations by reducing the rate of protein aggregation. The anti-aggregation additive selected depends upon the nature of the conditions to which the corticosteroids, for example corticosteroid antibodies are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations optionally include one or more auris-acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more auris-acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the auris-acceptable pharmaceutical formulations described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months. In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the auris-acceptable formulations of the present disclosure, they are combined, e.g., with a pharmaceutically acceptable vehicle and is present in the final formulation, e.g., in an amount ranging from about 0.1% to about 20%, from about 0.5% to about 10%.

In one embodiment, diluents are also used to stabilize the corticosteroid or other pharmaceutical compounds because they provide a more stable environment. Salts dissolved in buffered solutions (which also can provide pH control or maintenance) are utilized as diluents, including, but not limited to a phosphate buffered saline solution. In other embodiments, the gel formulation is isotonic with the endolymph or the perilymph: depending on the portion of the cochlea that the corticosteroid formulation is targeted. Isotonic formulations are provided by the addition of a tonicity agent. Suitable tonicity agents include, but are not limited to any pharmaceutically acceptable sugar, salt or any combinations or mixtures thereof, such as, but not limited to dextrose and sodium chloride. The amount of tonicity agents will depend on the target structure of the pharmaceutical formulation, as described herein.

Useful tonicity compositions also include one or more salts in an amount required to bring osmolality of the composition into an acceptable range for the perilymph or the endolymph. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the auris-acceptable gel formulations disclosed herein alternatively or additionally contains preservatives to prevent microbial growth. Suitable auris-acceptable preservatives for use in the enhanced viscosity formulations described herein include, but are not limited to benzoic acid, boric acid, p-hydroxybenzoates, alcohols, quarternary compounds, stabilized chlorine dioxide, mercurials, such as merfen and thiomersal, mixtures of the foregoing and the like.

In a further embodiment, the preservative is, by way of example only, an antimicrobial agent, within the auris-acceptable formulations presented herein. In one embodiment, the formulation includes a preservative such as by way of example only, methyl paraben, sodium bisulfite, sodium thiosulfate, ascorbate, chlorobutanol, thimerosal, parabens, benzyl alcohol, phenylethanol and others. In another embodiment, the methyl paraben is at a concentration of about 0.05% to about 1.0%, about 0.1% to about 0.2%. In a further embodiment, the gel is prepared by mixing water, methylparaben, hydroxyethylcellulose and sodium citrate. In a further embodiment, the gel is prepared by mixing water, methylparaben, hydroxyethylcellulose and sodium acetate. In a further embodiment, the mixture is sterilized by autoclaving at 120° C. for about 20 minutes, and tested for pH, methylparaben concentration and viscosity before mixing with the appropriate amount of the corticosteroid disclosed herein.

Suitable auris-acceptable water soluble preservatives which are employed in the drug delivery vehicle include sodium bisulfite, sodium thiosulfate, ascorbate, chlorobutanol, thimerosal, parabens, benzyl alcohol, Butylated hydroxytoluene (BHT), phenylethanol and others. These agents are present, generally, in amounts of about 0.001% to about 5% by weight and, preferably, in the amount of about 0.01 to about 2% by weight. In some embodiments, auris-compatible formulations described herein are free of preservatives.

Round Window Membrane Penetration Enhancers

In another embodiment, the formulation further comprises one or more round window membrane penetration enhancers. Penetration across the round window membrane is enhanced by the presence of round window membrane penetration enhancers. Round window membrane penetration enhancers are chemical entities that facilitate transport of coadministered substances across the round window membrane. Round window membrane penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween® 80, nonylphenoxypolyethylene (NP-POE), polysorbates and the like, function as round window membrane penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, glycerol, propanediol and the like) also function as round window membrane penetration enhancers.

Round Window Membrane Permeable Liposomes

Liposomes or lipid particles may also be employed to encapsulate the corticosteroid formulations or compositions. Phospholipids that are gently dispersed in an aqueous medium form multilayer vesicles with areas of entrapped aqueous media separating the lipid layers. Sonication, or turbulent agitation, of these multilayer vesicles results in the formation of single layer vesicles, commonly referred to as liposomes, with sizes of about 10-1000 nm. These liposomes have many advantages as corticosteroids or other pharmaceutical agent carriers. They are biologically inert, biodegradable, non-toxic and non-antigenic. Liposomes are formed in various sizes and with varying compositions and surface properties. Additionally, they are able to entrap a wide variety of agents and release the agent at the site of liposome collapse.

Suitable phospholipids for use in auris-acceptable liposomes here are, for example, phosphatidyl cholines, ethanolamines and serines, sphingomyelins, cardiolipins, plasmalogens, phosphatidic acids and cerebrosides, in particular those which are soluble together with the corticosteroids herein in non-toxic, pharmaceutically acceptable organic solvents. Preferred phospholipids are, for example, phosphatidyl choline, phosphatidyl ethanolamine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation range from about 10 to about 30%, preferably from about 15 to about 25% and in particular is about 20%.

Lipophilic additives may be employed advantageously to modify selectively the characteristics of the liposomes. Examples of such additives include by way of example only, stearylamine, phosphatidic acid, tocopherol, cholesterol, cholesterol hemisuccinate and lanolin extracts. The amount of lipophilic additive used range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the corticosteroid and other pharmaceutical compounds are employed in conjunction with a non-toxic, pharmaceutically acceptable organic solvent system which dissolve said ingredients. Said solvent system not only must dissolve the corticosteroid completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol range from about 2:1 to about 1:3, in particular from about 1:1 to about 1:2.5 and preferably is about 1:2. The amount of tetraglycol in the final composition thus vary from 5 to 20%, in particular from 5 to 15% and preferably is approximately 10%. The amount of dimethylisosorbide in the final composition thus range from 3 to 10%, in particular from 3 to 7% and preferably is approximately 5%.

The term "organic component" as used hereinafter refers to mixtures comprising said phospholipid, lipophilic additives and organic solvents. The corticosteroid may be dissolved in the organic component, or other means to maintain full activity of the agent. The amount of corticosteroid in the final formulation may range from 0.1 to 5.0%. In addition, other ingredients such as anti-oxidants may be added to the organic component. Examples include tocopherol, butylated hydroxyanisole, butylated hydroxytoluene, ascorbyl palmitate, ascorbyl oleate and the like.

In other embodiments, the auris-acceptable formulations, including gel formulations and viscosity-enhanced formulations, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Suitable carriers for use in an auris-acceptable formulation described herein include, but are not limited to, any pharmaceutically acceptable solvent compatible with the targeted auris structure's physiological environment. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations or mixtures thereof.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based auris-acceptable enhanced viscosity formulations utilized in the preparation of pharmaceutical delivery vehicles comprise at least one corticosteroid containing at least about 0.1% of the water-soluble glycerin compound or more. In some embodiments, the percentage of corticosteroid is varied between about 1% and about 95%, between about 5% and about 80%, between about 10% and about 60% or more of the weight or volume of the total pharmaceutical formulation. In some embodiments, the amount of the compound(s) in each therapeutically useful corticosteroid formulation is prepared in such a way that a suitable dosage will be obtained in any given unit dose of the compound. Factors such as solubility, bioavailability, biological half-life, route of administration, product shelf life, as well as other pharmacological considerations are contemplated herein.

If desired, the auris-acceptable pharmaceutical gels also contain co-solvents, and buffering agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition.

Cosolvents are used to enhance corticosteroid solubility, however, some corticosteroids or other pharmaceutical compounds are insoluble. These are often suspended in the polymer vehicle with the aid of suitable suspending or viscosity enhancing agents.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled release corticosteroid formulation, it is advised to avoid or combine the appropriate excipients, diluents or carriers to lessen or eliminate potential ototoxic components from the formulation, or to decrease the amount of such excipients, diluents or carriers. Optionally, a controlled release corticosteroid formulation includes otoprotective agents, such as antioxidants, alpha lipoic acid, calcium, fosfomycin or iron chelators, to counteract potential ototoxic effects that may arise from the use of specific therapeutic agents or excipients, diluents or carriers.

Modes of Treatment

Dosing Methods and Schedules

Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in which high levels of drug are found in the serum and correspondingly lower levels are found at the inner ear.

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the corticosteroid auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In one embodiment the delivery system is a syringe and needle apparatus that is capable of piercing the tympanic membrane and directly accessing the round window membrane or crista fenestrae cochleae of the auris interna. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the corticosteroid compositions or formulations, the gauge level of the syringe or hypodermic needle may be varied accordingly.

In another embodiment, the needle is a hypodermic needle used for instant delivery of the gel formulation. The hypodermic needle may be a single use needle or a disposable needle. In some embodiments, a syringe may be used for delivery of the pharmaceutically acceptable gel-based corticosteroid-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel formulation is stored before use. In other embodiments, the syringe comprises a cylindrical syringe body wherein the corticosteroid pharmaceutically acceptable gel-based compositions as disclosed herein is stored before use which conveniently allows for mixing with a suitable pharmaceutically acceptable buffer. In other embodiments, the syringe may contain other excipients, stabilizers, suspending agents, diluents or a combination thereof to stabilize or otherwise stably store the corticosteroid or other pharmaceutical compounds contained therein.

In some embodiments, the syringe comprises a cylindrical syringe body wherein the body is compartmentalized in that each compartment is able to store at least one component of the auris-acceptable corticosteroid gel formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel formulation such that each component is pre-mixed prior to injection or is mixed subsequent to injection. In a further embodiment, the syringes disclosed herein comprise at least one reservoir wherein the at least one reservoir comprises an corticosteroid, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

The formulations described herein, and modes of administration thereof, are also applicable to methods of direct instillation or perfusion of the inner ear compartments. Thus, the formulations described herein are useful in surgical procedures including, by way of non-limiting examples, cochleostomy, labyrinthotomy, mastoidectomy, stapedectomy, endolymphatic sacculotomy or the like.

The auris-acceptable compositions or formulations containing the corticosteroid compound(s) described herein are administered for prophylactic and/or therapeutic treatments. In therapeutic applications, the corticosteroid compositions are administered to a patient already suffering from an autoimmune disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

In the case wherein the patient's condition does not improve, upon the doctor's discretion the administration of the corticosteroid compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the corticosteroid compounds may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's autoimmune conditions has occurred, a maintenance corticosteroid dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of corticosteroid that will correspond to such an amount will vary depending upon factors such as the particular compound, disease condition and its severity, according to the particular circumstances surrounding the case, including, e.g., the specific corticosteroid being administered, the route of administration, the autoimmune condition being treated, the target area being treated, and the subject or host being treated. In general, however, doses employed for adult human treatment will typically be in the range of 0.02-50 mg per administration, preferably 1-15 mg per administration. The desired dose is presented in a single dose or as divided doses administered simultaneously (or over a short period of time) or at appropriate intervals.

In some embodiments, the initial administration is a particular corticosteroid and the subsequent administration a different formulation or corticosteroid.

Pharmacokinetics of Controlled Release Formulations

In one embodiment, the formulations disclosed herein additionally provides an immediate release of an corticosteroid from the formulation, or within 1 minute, or within 5 minutes, or within 10 minutes, or within 15 minutes, or within 30 minutes, or within 60 minutes or within 90 minutes. In other embodiments, a therapeutically effective amount of at least one corticosteroid is released from the formulation immediately, or within 1 minute, or within 5 minutes, or within 10 minutes, or within 15 minutes, or within 30 minutes, or within 60 minutes or within 90 minutes. In certain embodiments the formulation comprises an auris-pharmaceutically acceptable gel formulation providing immediate release of at least one corticosteroid. Additional embodiments of the formulation may also include an agent that enhances the viscosity of the formulations included herein.

In other or further embodiments, the formulation provides an extended release formulation of at least one corticosteroid. In certain embodiments, diffusion of at least one corticosteroid from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one corticosteroid is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of an corticosteroid. In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first corticosteroid and an extended release of a second corticosteroid or other therapeutic agent. In yet other embodiments, the formulation provides an immediate release and extended release formulation of at least one corticosteroid, and at least one therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first corticosteroid and second therapeutic agent, respectively.

In a specific embodiment the formulation provides a therapeutically effective amount of at least one corticosteroid at the site of disease with essentially no systemic exposure. In an additional embodiment the formulation provides a therapeutically effective amount of at least one corticosteroid at the site of disease with essentially no detectable systemic exposure. In other embodiments, the formulation provides a therapeutically effective amount of at least one corticosteroid at the site of disease with little or no detectable systemic exposure.

The combination of immediate release, delayed release and/or extended release corticosteroid compositions or formulations may be combined with other pharmaceutical agents, as well as the excipients, diluents, stabilizers, tonicity agents and other components disclosed herein. As such, depending upon the corticosteroid used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the corticosteroid formulations described herein are determined by injecting the formulation on or near the round window membrane of a test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a formulation over a 1 week period), the test animal is euthanized and a 5 mL sample of the perilymph fluid is tested. The inner ear removed and tested for the presence of the corticosteroid. As needed, the level of corticosteroid is measured in other organs. In addition, the systemic level of the corticosteroid is measured by withdrawing a blood sample from the test animal. In order to determine whether the formulation impedes hearing, the hearing of the test animal is optionally tested.

Alternatively, an inner ear is provided (as removed from a test animal) and the migration of the corticosteroid is measured. As yet another alternative, an in vitro model of a round window membrane is provided and the migration of the corticosteroid is measured.

Kits/Articles of Manufacture

The disclosure also provides kits for preventing, treating or ameliorating the symptoms of a disease or disorder in a mammal. Such kits generally will comprise one or more of the corticosteroid controlled-release compositions or devices disclosed herein, and instructions for using the kit. The disclosure also contemplates the use of one or more of the corticosteroid controlled-release compositions, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of corticosteroid formulations compositions provided herein are contemplated as are a variety of treatments for any disease, disorder, or condition that would benefit by controlled release administration of a corticosteroid to the inner ear.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or

EXAMPLES

Example 1

Preparation of a Thermoreversible Gel Dexamethasone Formulation or Device

| Ingredient | Quantity (mg/g of formulation) |
| --- | --- |
| Dexamethasone | 20.0 |
| methylparaben | 1.0 |
| HPMC | 10.0 |
| Poloxamer 407 | 180.0 |
| TRIS HCl buffer (0.1M) | 789.0 |

A 10-g batch of gel formulation containing 2.0% of Dexamethasone is prepared by suspending 1.80 g of Poloxamer 407 (BASF Corp.) in 5.00 g of TRIS HCl buffer (0.1 M) and the components are mixed under agitation overnight at 4° C. to ensure complete dissolution. Dexamethasone (200.0 mg), hydroxypropylmethylcellulose (100.0 mg), methylparaben (10 mg) and additional TRIS HCl buffer (0.1 M) (2.89 g) is added and further stirring allowed until complete dissolution is observed. The mixture is maintained below room temperature until use.

Example 2

Preparation of a Mucoadhesive, Thermoreversible Gel Prednisolone Formulation or Device

| Ingredient | Quantity (mg/g of formulation) |
| --- | --- |
| Prednisolone | 30 |
| methylparaben | 1.0 |
| HPMC | 10.0 |
| Carbopol 934P | 2.0 |
| Poloxamer 407 | 180.0 |
| TRIS HCl buffer (0.1M) | 787.0 |

A 10-g batch of mucoadhesive, gel formulation containing 2.0% of Prednisolone is prepared by suspending 2.0 mg of Carbopol 934P and 1.80 g of Poloxamer 407 (BASF Corp.) in 5.00 g of TRIS HCl buffer (0.1 M) and the components are mixed under agitation overnight at 4° C. to ensure complete dissolution. The Prednisolone, hydroxypropylmethylcellulose (100.0 mg), methylparaben (10 mg) and additional TRIS HCl buffer (0.1 M) (2.87 g) are added and further stirring allowed until complete dissolution is observed. The mixture is maintained below room temperature until use.

Example 3

Preparation of a Cyclodextrin-Containing Thermoreversible Gel 2.5% Dexamethasone Formulation or Device

| Ingredient | Quantity (mg/g of formulation) |
| --- | --- |
| 5% CD solution | 500.0 |
| methylparaben | 1.0 |
| Poloxamer 407 | 180.0 |
| TRIS HCl buffer (0.1M) | 317.0 |

The Poloxamer 407 (BASF Corp.) is suspended in the TRIS HCl buffer (0.1 M) and the components are mixed under agitation overnight at 4° C. to ensure complete dissolution. The cyclodextrin solution and methylparaben is added and further stirring allowed until complete dissolution is observed. The mixture is maintained below room temperature until use.

Example 4

Preparation of a Cyclodextrin-Containing Mucoadhesive, Thermoreversible Gel Dexamethasone Formulation or Device

| Ingredient | Quantity (mg/g of formulation) |
| --- | --- |
| 5% CD solution | 500.0 |
| methylparaben | 1.0 |
| Poloxamer 407 | 180.0 |
| Carbopol 934P | 2.0 |
| TRIS HCl buffer (0.1M) | 317.0 |

The Carbopol 934P and Poloxamer 407 (BASF Corp.) is suspended in the TRIS HCl buffer (0.1 M) and the components are mixed under agitation overnight at 4° C. to ensure complete dissolution. The cyclodextrin solution and methylparaben is added and further stirring allowed until complete dissolution is observed. The mixture is maintained below room temperature until use.

Example 5

Preparation of a Thermoreversible Gel Dexamethasone Formulation or Device Comprising Micronized Dexamethasone Powder

| Ingredient | Quantity (mg/g of formulation) |
| --- | --- |
| Dexamethasone | 20.0 |
| BHT | 0.002 |
| Poloxamer 407 | 160.0 |
| PBS buffer (0.1M) | 9.0 |

A 10-g batch of gel formulation containing 2.0% of micronized Dexamethasone, 13.8 mg of sodium phosphate dibasic dihydrate USP (Fisher Scientific.)+3.1 mg of sodium phosphate monobasic monohydrate USP (Fisher Scientific.)+74 mg of sodium chloride USP (Fisher Scientific.) was dissolved with 8.2 g of sterile filtered DI water and the pH was adjusted to 7.4 with 1 M NaOH. The buffer solution was chilled down and 1.6 g of poloxamer 407 (BASF Corp., containing approximately 100 ppm of BHT) was sprinkled into the chilled PBS solution while mixing, solution was mixed until all the poloxamer was dissolved. The poloxamer was sterile filtered using a 33 mm PVDF 0.22 μm sterile syringe filter (Millipore Corp.) and delivered to 2 mL sterile glass vials (Wheaton) in an aseptic environment, the vials were closed with sterile butyl rubber stoppers (Kimble) and crimped sealed with 13 mm Al seals (Kimble). 20 mg of micronized dexamethasone (Spectrum chemicals) was placed in separate clean depyrogenated vials, the vials were closed with sterile butyl rubber stoppers (Kimble) and crimped sealed with 13 mm Al seals (Kimble), vials were dry heat sterilized (Fisher Scientific Isotemp oven) for 7 hours at 140° C. Before administration for the experiments described herein, 1 mL of the cold poloxamer solution was delivered to a vial containing 20 mg of sterile micronized dexamethasone using a 21 G needle (Becton Dickinson) attached to a 1 mL sterile syringe (Becton Dickinson), suspension mixed well by shaking to ensure homogeneity of the suspension. The suspension was then withdrawn with the 21 G syringe and the needle was switched to a 27 G needle for administration.

Example 6

Preparation of a Thermoreversible Gel Micronized Prednisone Formulation or Device Comprising a Penetration Enhancer

| Ingredient | Quantity (mg/g of formulation) |
| --- | --- |
| Prednisone | 20.0 |
| methylparaben | 1.0 |
| Dodecyl maltoside (A3) | 1.0 |
| HPMC | 10.0 |
| Poloxamer 407 | 180.0 |
| TRIS HCl buffer (0.1M) | 789.0 |

A 10-g batch of gel formulation containing 2.0% of micronized prednisone is prepared by suspending 1.80 g of Poloxamer 407 (BASF Corp.) in 5.00 g of TRIS HCl buffer (0.1 M) and the components are mixed under agitation overnight at 4° C. to ensure complete dissolution. Prednisone (200.0 mg), hydroxypropylmethylcellulose (100.0 mg), methylparaben (10 mg) and dodecyl maltoside (10 mg) and additional TRIS HCl buffer (0.1 M) (2.89 g) is added and further stirring allowed until complete dissolution is observed. The mixture is maintained below room temperature until use.

Example 7

Effect of pH on Degradation Products for Autoclaved 17% Poloxamer 407NF/2% Dexamethasone Phosphate (DSP) in PBS Buffer A stock solution of a 17% poloxamer 407/2% dexamethasone phosphate (DSP) is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and 2.062 g dexamethasone phosphate (DSP) with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured.

17% poloxamer 407/2% dexamethasone phosphate (DSP) in PBS pH of 5.3. Take an aliquot (approximately 30 mL) of the above solution and adjust the pH to 5.3 by the addition of 1 M HCl.

17% poloxamer 407/2% dexamethasone phosphate (DSP) in PBS pH of 8.0. Take an aliquot (approximately 30 mL) of the above stock solution and adjust the pH to 8.0 by the addition of 1 M NaOH.

A PBS buffer (pH 7.3) is prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

A 2% solution of dexamethasone phosphate (DSP) in PBS pH 7.3 is prepared by dissolving 206 mg of dexamethasone phosphate (DSP) in the PBS buffer and QS to 10 g with PBS buffer.

One mL samples are individually placed in 3 mL screw cap glass vials (with rubber lining) and closed tightly. The vials are placed in a Market Forge-sterilmatic autoclave (settings, slow liquids) and sterilized at 250° F. for 15 minutes. After the autoclave the samples are left to cool down to room temperature and then placed in refrigerator. The samples are homogenized by mixing the vials while cold.

Appearance (e.g., discoloration and/or precipitation) is observed and recorded. The 2% DSP in PBS alone showed discoloration (slight yellow) and some precipitation, while the samples containing poloxamer did not show signs of discoloration. Of the poloxamer containing samples, precipitation was only observed with the sample at a pH of 5.3.

HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. The main peaks were recorded in the table below. Samples are diluted by taking 30 μL of sample and dissolved with 1.5 mL of a 1:1 acetonitrile water mixture. Purity of the samples before autoclaving was always greater than 99%.

TABLE 1

Observed properties after autoclaving samples containing dexamethasone sodium phosphate (DSP)

|  | Appearance | % DSP | % Dex (RRT = 1.27) | % RRT of 1.54 | % RRT of 1.68 |
| --- | --- | --- | --- | --- | --- |
| 2% DSP pH = 7.3 | Yellowish | 89 | 6.5 | 1.41 | — |
| 17% 407/2% DSP PBS, pH = 5.3 | Precipitate | 53 | 45.9 | 0.48 | 0.56 |
| 17% 407/2% DSP PBS, pH = 7.3 | Clear Solution/Gel | 88 | 10 | 0.79 | — |
| 17% 407/2% DSP PBS, pH = 8.0 | Clear Solution/Gel | 92 | 4.9 | 1.18 | — |

Purity before autoclaving was 99+% for all samples.

Example 8

Effect of Autoclaving on the Release Profile and Viscosity of a 17% Poloxamer 407NF/2% Dexamethasone Phosphate (DSP) in PBS An aliquot of the sample from example 6 (autoclaved and not autoclaved) is evaluated for release profile and viscosity measurement to evaluate the impact of heat sterilization on the properties of the gel.

Dissolution is performed at 37° C. in snapwells (6.5 mm diameter polycarbonate membrane with a pore size of 0.4 μm). 0.2 mL of gel is placed into snapwell and left to harden, then 0.5 mL is placed into reservoir and shaken using a Labline orbit shaker at 70 rpm. Samples are taken every hour (0.1 mL withdrawn and replace with warm buffer). Samples are analyzed for poloxamer concentration by UV at 624 nm using the cobalt thiocyanate method, against an external calibration standard curve. In brief, 20 μL of the sample is mixed with 1980 μL of a 15 mM cobalt thiocyanate solution and absorbance measured at 625 nm, using a Evolution 160 UV/Vis spectrophotometer (Thermo Scientific).

The released dexamethasone phosphate (DSP) is fitted to the Korsmeyer-Peppas equation $$\frac{Q}{Q_\alpha} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is calculated by:

$$MDT = \frac{nk^{-1/n}}{n+1}$$

Viscosity measurements are performed using a Brookfield viscometer RVDV-II+P with a CPE-51 spindle rotated at 0.08 rpm (shear rate of 0.31 $s^{-1}$), equipped with a water jacketed temperature control unit (temperature ramped from 15-34° C. at 1.6° C./min). Tgel is defined as the inflection point of the curve where the increase in viscosity occurs due to the sol-gel transition.

TABLE 2

Effect of autoclaving on the release profile and viscosity of a 17% poloxamer 407NF/2% dexamethasone sodium phosphate (DSP) in PBS.

|  | MDT (hr) | Tgel (° C.) | Max Viscosity* (Pas) |
|---|---|---|---|
| Non-autoclaved | 3.2 | 25 | 403 |
| Autoclaved | 3.2 | 26 | 341 |

*Maximum apparent viscosity in the gel state (up to 37° C.) at a shear rate of 0.31 $s^{-1}$
The results show little effect on viscosity and release profile after autoclaving a 17% poloxamer 407NF/2% dexamethasone sodium phosphate (DSP) in PBS.

Example 9

Effect of Addition of a Secondary Polymer on the Degradation Products and Viscosity of a Formulation Containing 2% Dexamethasone Phosphate (DSP) and 17% Poloxamer 407NF after Heat Sterilization (Autoclaving)

Solution A. A solution of pH 7.0 comprising sodium carboxymethylcellulose (CMC) in PBS buffer is prepared by dissolving 178.35 mg of sodium chloride (Fisher Scientific), 300.5 mg of sodium phosphate dibasic anhydrous (Fisher Scientific), 126.6 mg of sodium phosphate monobasic anhydrous (Fisher Scientific) dissolved with 78.4 of sterile filtered DI water, then 1 g of Blanose 7M65 CMC (Hercules, viscosity of 5450 cP @ 2%) is sprinkled into the buffer solution and heated to aid dissolution, and the solution is then cooled down.

A solution of pH 7.0 comprising 17% poloxamer 407NF/1% CMC/2% dexamethasone sodium phosphate (DSP) in PBS buffer is made by cooling down 8.1 g of solution A in a ice chilled water bath and then adding 205 mg of dexamethasone sodium phosphate (DSP) followed by mixing. 1.74 g of poloxamer 407NF (Spectrum Chemicals) is sprinkled into the cold solution while mixing. The mixture is further mixed until all the poloxamer is completely dissolved.

Two mL of the above sample is placed in a 3 mL screw cap glass vial (with rubber lining) and closed tightly. The vial is placed in a Market Forge-sterilmatic autoclave (settings, slow liquids) and sterilized at 250° F. for 25 minutes. After autoclaving the sample is left to cool down to room temperature and then placed in refrigerator. The sample is homogenized by mixing while the vials are cold.

No Precipitation or discoloration was observed after autoclaving. HPLC analysis is performed as described in Example 6. Less than 1% of degradation products due to hydrolysis of dexamethasone products were detected, i.e., the formulation was stable to autoclaving.

Viscosity measurements were performed as described in Example 7. The results showed that autoclaving had little effect on the viscosity of the gel, or the Tgel temperature. Less overall impurities were observed in poloxamer containing formulations compared to the control sample (2% DSP in PBS).

Dissolution testing was performed as described in example 7. The results showed a MDT of 11.9 hr compared to a MDT of 3.2 hr for a formulation containing no CMC. The addition of CMC or a secondary polymer introduces a diffusional barrier that reduces the rate of release of the dexamethasone (i.e., increases MDT).

Example 10

Effect of Buffer Type on the Degradation Products for Formulations Containing Poloxamer 407NF after Heat Sterilization (Autoclaving)

A TRIS buffer is made by dissolving 377.8 mg of sodium chloride (Fisher Scientific), and 602.9 mg of Tromethamine (Sigma Chemical Co.) then QS to 100 g with sterile filtered DI water, pH is adjusted to 7.4 with 1M HCl.

Stock Solution Containing 25% Poloxamer 407 Solution in TRIS Buffer:

Weigh 45 g of TRIS buffer, chill in an ice chilled bath then sprinkle into the buffer, while mixing, 15 g of poloxamer 407 NF (Spectrum Chemicals). The mixture is further mixed until all the poloxamer is completely dissolved. Stock solution (pH 7.3) containing 25% Poloxamer 407 solution in PBS buffer:

Dissolve 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water. The solution is cooled down in an ice chilled water bath and then 50 g of poloxamer 407NF (SPECTRUM CHEMICALS) is sprinkled into the cold solution while mixing. The mixture is further mixed until the poloxamer is completely dissolved and a clear translucid solution was obtained. The pH obtained for this solution was measured at 7.3.

A series of formulations are prepared with the above stock solutions. Dexamethasone phosphate (DSP) and micronized Dexamethasone USP from spectrum chemicals were used for all experiments.

One mL samples are individually placed in 3 mL screw cap glass vials (with rubber lining) and closed tightly. The vials are placed in a Market Forge-sterilmatic autoclave (setting, slow liquids) and sterilized at 250° F. for 25 minutes. After the autoclaving the samples are left to cool down to room temperature. The vials are placed in the refrigerator and mixed while cold to homogenize the samples.

HPLC analysis is performed as described in example 6. The stability of formulations in TRIS and PBS buffers is compared.

TABLE 3

Effect of buffer type on the degradation of dexamethasone and dexamethasone phosphate containing formulations.

| Sample ID | Appearance | % DSP | % Dex (RRT = 1.27) | % RRT of 1.54 | % RRT of 1.68 |
|---|---|---|---|---|---|
| 1% DSP/TRIS | Yellowish & Precipitate | 41 | 54 | 2.68 | 0.97 |
| 2% DSP/TRIS | Yellowish & Precipitate | 41 | 55 | 2.4 | 0.57 |
| 4% DSP/TRIS | Yellowish & Precipitate | 58 | 36 | 2.4 | 0.23 |
| 16% P407/2DSP/TRIS | Precipitate | 54 | 41 | 0.79 | 0.62 |
| 18% P407/2DSP/TRIS | Precipitate | 52 | 45 | 1.21 | 0.51 |
| 20% P407/2DSP/TRIS | Precipitate | 55 | 43 | 0.86 | 0.49 |
| 18% P407/2DEX/TRIS | Suspension | — | 99 | 0.22 | 0.55 |
| 2% DEX/TRIS | Suspension | — | 99 | — | 0.28 |
| 2% DSP/PBS | Yellowish & Precipitate | 85.6 | 9.8 | 2.09 | — |
| 16% P407/2DSP/PBS | Clear solution | 78 | 17.5 | 1.86 | — |
| 18% P407/2DSP/PBS | Clear solution | 81.2 | 16.2 | 1.14 | — |
| 20% P407/2DSP/PBS | Clear solution | 81.5 | 16.1 | 1.04 | — |
| 18% P407/2DEX/PBS | Suspension | — | 97 | 1.06 | 0.45 |
| 2% DEX/PBS | Suspension | — | 94.7 | 1.34 | — |

Viscosity measurements were performed as described in example 7.

The results show that in order to reduce hydrolysis during autoclaving, the buffer needs to maintain a pH in the 7-8 range at elevated temperatures. Increased drug hydrolysis was observed in TRIS buffer than in PBS (Table 3). Occurrence of other degradation products are reduced by the use of the polymeric additives (e.g. P407) described in this application. A decrease in degradation products is observed from the formulation containing 20% poloxamer 407 compared to the one with no poloxamer 407 (Table 7).

The formulations containing suspended micronized dexamethasone had greater stability upon autoclaving, than their solution counterparts.

Example 11

Pulsed Release Otic Formulations

A combination of dexamethasone and dexamethasone sodium phosphate (DSP) (ratio of 1:1) is used to prepare a pulsed release formulation using the procedures described herein. 20% of the deliverable dose of dexamethasone is solubilized in a 17% poloxamer solution of example 7 with the aid of beta-cyclodextrins. The remaining 80% of the deliverable dexamethasone is then added to the mixture and the final formulation is prepared using any procedure described herein.

Pulsed release formulations comprising dexamethasone are prepared according to the procedures and examples described herein, and are tested using procedures described herein to determine pulse release profiles.

Example 12

Preparation of a 17% Poloxamer 407/2% DSP/78 ppm Evans Blue in PBS

A Stock solution of Evans Blue (5.9 mg/mL) in PBS buffer is prepared by dissolving 5.9 mg of Evans Blue (Sigma Chemical Co) with 1 mL of PBS buffer (from example 61).

A Stock solution containing 25% Poloxamer 407 solution in PBS buffer from example 8 is used in this study. An appropriate amount of DSP is added to the stock solution from example 8 to prepare formulations comprising 2% DSP (Table 4).

TABLE 4

Stock solution containing 25% Poloxamer 407 solution in PBS buffer from example 9 was used for this study.

| Sample ID | 25% P407 in PBS (g) | DSP (mg) | PBS Buffer (g) | Evans Blue Solution (µL) |
|---|---|---|---|---|
| 17% P407/2DSP/EB | 13.6 | 405.6 | 6 | 265 |
| 20% P407/2DSP/EB | 16.019 | 407 | 3.62 | 265 |
| 25% P407/2DSP/EB | 19.63 | 407 | — | 265 |

The above formulations are dosed to guinea pigs in the middle ear by procedures described herein and the ability of formulations to gel upon contact and the location of the gel is identified after dosing and at 24 hours after dosing.

Example 13

Terminal Sterilization of Poloxamer 407 Formulations with and without a Visualization Dye 17% poloxamer407/2% DSP/in phosphate buffer, pH 7.3: Dissolve 709 mg of sodium chloride (Fisher Scientific), 742 mg of sodium phosphate dibasic dehydrate USP (Fisher Scientific), 251.1 mg of sodium phosphate monobasic monohydrate USP (Fisher Scientific) and an appropriate amount of DSP with 158.1 g of sterile filtered DI water. The solution is cooled down in an ice chilled water bath and then 34.13 g of poloxamer 407NF (Spectrum chemicals) is sprinkled into the cold solution while mixing. The mixture is further mixed until the poloxamer is completely dissolved and a clear translucid solution was obtained. The pH of this solution was 7.3.

17% poloxamer407/2% DSP/59 ppm Evans blue in phosphate buffer: Take two mL of the 17% poloxamer407/2%

DSP/in phosphate buffer solution and add 2 mL of a 5.9 mg/mL Evans blue (Sigma-Aldrich chemical Co) solution in PBS buffer.

25% poloxamer407/2% DSP/in phosphate buffer: Dissolve 330.5 mg of sodium chloride (Fisher Scientific), 334.5 mg of sodium phosphate dibasic dihydrate USP (Fisher Scientific), 125.9 mg of sodium phosphate monobasic monohydrate USP (Fisher Scientific) and 2.01 g of dexamethasone sodium phosphate USP (Spectrum Chemicals) with 70.5 g of sterile filtered DI water.

The solution is cooled down in an ice chilled water bath and then 25.1 g of poloxamer 407NF (Spectrum chemicals) is sprinkled into the cold solution while mixing. The mixture is further mixed until the poloxamer is completely dissolved and a clear translucid solution is obtained. The pH of this solution was 7.3.

25% poloxamer407/2% DSP/59 ppm Evans blue in phosphate buffer: Take two mL of the 25% poloxamer407/2% DSP/in phosphate buffer solution and add 2 mL of a 5.9 mg/mL Evans blue (Sigma-Aldrich chemical Co) solution in PBS buffer.

Place 2 mL of formulation into a 2 mL glass vial (Wheaton serum glass vial) and seal with 13 mm butyl str (kimble stoppers) and crimp with a 13 mm aluminum seal. The vials are placed in a Market Forge-sterilmatic autoclave (settings, slow liquids) and sterilized at 250° F. for 25 minutes. After the autoclaving the samples are left to cool down to room temperature and then placed in refrigeration. The vials are placed in the refrigerator and mixed while cold to homogenize the samples. Sample discoloration or precipitation after autoclaving is recorded.

HPLC analysis is performed as described in Example 6.

TABLE 5

Effect of autoclaving on the purity of formulations containing dexamethasone sodium phosphate with and without visualization dye.

| Sample ID | % RRT of 0.68 | % DSP | % Dex (RRT = 1.28) | % RRT of 1.41 | % RRT of 1.76 |
|---|---|---|---|---|---|
| 17% P407 | 1.1 | 84.5 | 12.0 | 0.7 | 0.09 |
| 17% P407/Evans Blue | 1.1 | 84.4 | 11.7 | 0.8 | 0.09 |
| 25% P407 | 0.8 | 80.9 | 16.0 | 0.7 | 0.10 |
| 25% P407/Evans Blue | 0.9 | 80.9 | 15.3 | 0.7 | 0.12 |

Viscosity measurements are performed as described in example 7. The results showed that autoclaving formulations comprising a visual dye had no effect on degradation products and viscosity of the formulations.

Mean dissolution time (determined as described in example 7, measuring the amount of dexamethasone phosphate released by UV @ 245 nm) for the 25% poloxamer 407 formulations was measured to be 5.6 hr and for the 17% poloxamer 407 formulation showed to be 3.2 hr.

Example 14

In Vito Comparison of Release Profile

Dissolution is performed at 37° C. in snapwells (6.5 mm diameter polycarbonate membrane with a pore size of 0.4 μm), 0.2 mL of a gel formulation described herein is placed into snapwell and left to harden, then 0.5 mL buffer is placed into snapwell reservoir and shaken using a Labline orbit shaker at 70 rpm. Samples are taken every hour (0.1 mL withdrawn and replace with warm buffer). Samples are analyzed for dexamethasone concentration by UV at 245 nm against an external calibration standard curve. Pluronic concentration is analyzed at 624 nm using the cobalt thiocyanate method. Relative rank-order of mean dissolution time (MDT) as a function of % P407 is determined. A linear relationship between the formulations mean dissolution time (MDT) and the P407 concentration indicates that dexamethasone is released due to the erosion of the polymer gel (poloxamer) and not via diffusion. A non-linear relationship indicates release of dexamethasone via a combination of diffusion and/or polymer gel degradation.

Alternatively, samples are analyzed using the method described by Li Xin-Yu paper [Acta Pharmaceutica Sinica 2008, 43(2):208-203] and Rank-order of mean dissolution time (MDT) as a function of % P407 is determined.

Figure 2:
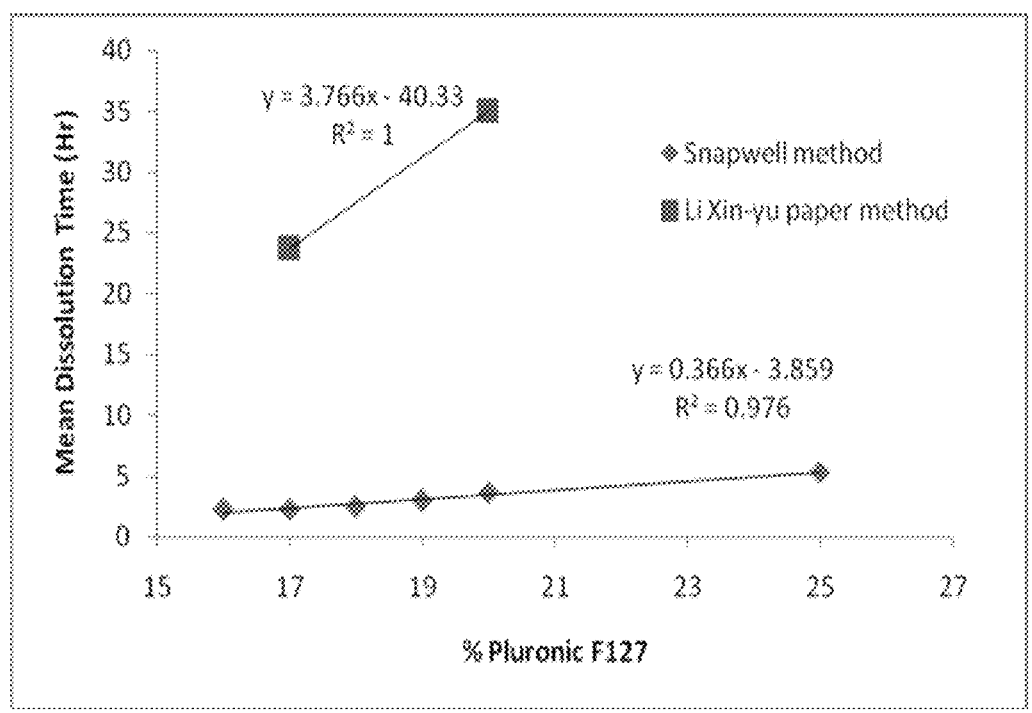
FIG. 2 illustrates the relationship between the mean dissolution time (MDT) of a formulation and the P407 concentration.

FIG. 1. illustrates in vitro release profile of Dexamethasone formulations with varying concentrations of. Poloxamer 407. FIG. 2 illustrates the nearly linear relationship (1:1 correlation) between the formulations' mean dissolution time (MDT) and the P407 concentration. The results indicate that dexamethasone is released due to the erosion of the polymer gel (poloxamer) and not via diffusion.

Example 15

In Vitro Comparison of Gelation Temperature

The effect of Poloxamer 188 and dexamethasone on the gelation temperature and viscosity of Poloxamer 407 formulations is evaluated with the purpose of manipulating the gelation temperature.

A 25% Poloxamer 407 stock solution in PBS buffer (from example 9) and the PBS solutions from example 6 are used. Poloxamer 188NF from BASF is used.

TABLE 6

Preparation of samples containing poloxamer 407/poloxamer 188

| Sample | 25% P407 Stock Solution (g) | Poloxamer 188 (mg) | PBS Buffer (g) |
|---|---|---|---|
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Mean dissolution time (method describe in example 7) for the 20% poloxamer 407/10% poloxamer 188 was measured to be 2.2 hr and for the 20% poloxamer 407/5% poloxamer 188 showed to be 2.6 hr. Viscosity is determined using procedure described in example 7. Autoclaving had no effect on the viscosity or Tgel of formulations containing poloxamer 188.

An equation is fitted to the data obtained and can be utilized to estimate the gelation temperature of F127/F68 mixtures (for 17-20% F127 and 0-10% F68).

$$T_{gel} = -1.8(\% F127) + 1.3(\% F68) + 53$$

An equation is fitted to the data obtained and can be utilized to estimate the Mean Dissolution Time (hr) based on the gelation temperature of F127/F68 mixtures (for 17-25% F127 and 0-10% F68), using results obtained in example 12 and 14.

$$MDT = -0.2(T_{gel}) + 8$$

Example 16

Determination of Temperature Range for Sterile Filtration

The viscosity at low temperatures is measured to help guide the temperature range at which the sterile filtration needs to occur to reduce the possibility of clogging.

Viscosity measurements are performed using a Brookfield viscometer RVDV-II+P with a CPE-40 spindle rotated at 1, 5 and 10 rpm (shear rate of 7.5, 37.5 and 75 s$^{-1}$), equipped with a water jacketed temperature control unit (temperature ramped from 10-25° C. at 1.6° C./min).

The Tgel of a 17% Pluronic P407 is determined as a function of increasing concentration of otic agent. The increase in Tgel for a 17% pluronic formulation is estimated by:

$$\Delta T_{gel} = 0.93[\% \text{ otic agent}]$$

TABLE 7

Viscosity of potential formulations at manufacturing/filtration conditions.

| Sample | Apparent Viscosity$^a$ (cP) | | Temperature |
|---|---|---|---|
| | 5° C. below Tgel | 20° C. | @ 100 cP |
| Placebo | 52 cP @ 17° C. | 120 cP | 19° C. |
| 17% P407/2% DSP | 90 cP @ 18° C. | 147 cP | 18.5° C. |
| 17% P407/6% DSP | 142 cP @ 22° C. | 105 cP | 19.7° C. |

$^a$Viscosity measured at a shear rate of 37.5 s$^{-1}$

The results show that sterile filtration of formulations described herein can be carried out at about 19° C.

Example 17

Determination of Manufacturing Conditions

An 8 liter batch of a 17% P407 placebo is manufactured to evaluate the manufacturing/filtration conditions. The placebo is manufactured by placing 6.4 liters of DI water in a 3 gallon SS pressure vessel, and left to cool down in the refrigerator overnight. The following morning the tank was taken out (water temperature 5° C., RT 18° C.) and 48 g of sodium chloride, 29.6 g of sodium phosphate dibasic dehydrate and 10 g of sodium phosphate monobasic monohydrate is added and dissolved with an overhead mixer (IKA RW20 @ 1720 rpm). Half hour later, once the buffer is dissolved (solution temperature 8° C., RT 18° C.), 1.36 kg of poloxamer 407 NF (spectrum chemicals) is slowly sprinkled into the buffer solution in a 15 minute interval (solution temperature 12° C., RT 18° C.), then speed is increased to 2430 rpm. After an additional one hour mixing, mixing speed is reduced to 1062 rpm (complete dissolution).

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 cm$^2$ are evaluated at 20 psi and 14° C. of solution 1) Sartopore 2, 0.2 μm 5445307HS-FF (PES), flow rate of 16 mL/min
2) Sartobran P, 0.2 μm 5235307HS-FF (cellulose ester), flow rate of 12 mL/min
3) Sartopore 2 XLI, 0.2 μm 5445307IS-FF (PES), flow rate of 15 mL/min Sartopore 2 filter 5441307H4-SS is used, filtration is carried out at the solution temperature using a 0.45, 0.2 μm Sartopore 2 150 sterile capsule (Sartorius Stedim) with a surface area of 0.015 m$^2$ at a pressure of 16 psi. Flow rate is measured at approximately 100 mL/min at 16 psi, with no change in flow rate while the temperature is maintained in the 6.5-14° C. range. Decreasing pressure and increasing temperature of the solution causes a decrease in flow rate due to an increase in the viscosity of the solution. Discoloration of the solution is monitored during the process.

TABLE 8

Predicted filtration time for a 17% poloxamer 407 placebo at a solution temperature range of 6.5-14° C. using Sartopore 2, 0.2 μm filters at a pressure of 16 psi of pressure.

| Filter | Size (m$^2$) | Estimated flow rate (mL/min) | Time to filter 8 L (estimated) |
|---|---|---|---|
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/Vis absorption are checked before filtration evaluation. Pluronic UV/Vis spectra are obtained by a Evolution 160 UV/Vis (Thermo Scientific). A peak in the range of 250-300 nm is attributed to BHT stabilizer present in the raw material (poloxamer).

The above process is applicable for manufacture of 17% P407 formulations, and includes temperature analysis of the room conditions. A temperature of about 19° C. reduces cost of cooling the container during manufacturing. In some instances, a jacketed container is used to further control the temperature of the solution to ease manufacturing concerns.

Example 18

In Vitro Release of Dexamethasone from an Autoclaved Micronized Sample

17% poloxamer 407/1.5% dexamethasone in TRIS buffer: 250.8 mg of sodium chloride (Fisher Scientific), and 302.4 mg of Tromethamine (Sigma Chemical Co.) is dissolved in 39.3 g of sterile filtered DI water, pH is adjusted to 7.4 with 1M HCl. 4.9 g of the above solution is used and 75.5 mg of micronized dexamethasone USP (Spectrum Scientific) is suspended and dispersed well. 2 mL of the formulation is transferred into a 2 mL glass vial (Wheaton serum glass vial) and sealed with 13 mm butyl styrene (kimble stoppers) and crimped with a 13 mm aluminum seal. The vial is placed in a Market Forge-sterilmatic autoclave (settings, slow liquids) and sterilized at 250° F. for 25 minutes. After the autoclaving the sample is left to cool down to room temperature. The vial is placed in the refrigerator and mixed while cold to homogenize the sample. Sample discoloration or precipitation after autoclaving is recorded.

Dissolution is performed at 37° C. in snapwells (6.5 mm diameter polycarbonate membrane with a pore size of 0.4 μm), 0.2 mL of gel is placed into snapwell and left to harden, then 0.5 mL PBS buffer is placed into reservoir and shaken using a Labline orbit shaker at 70 rpm. Samples are taken every hour [0.1 mL withdrawn and replaced with warm PBS buffer containing 2% PEG-40 hydrogenated castor oil (BASF) to enhance dexamethasone solubility]. Samples are analyzed for dexamethasone concentration by UV at 245 nm against an external calibration standard curve. The release rate is compared to other formulations disclosed herein. MDT time is calculated for each sample.

Figure 3:
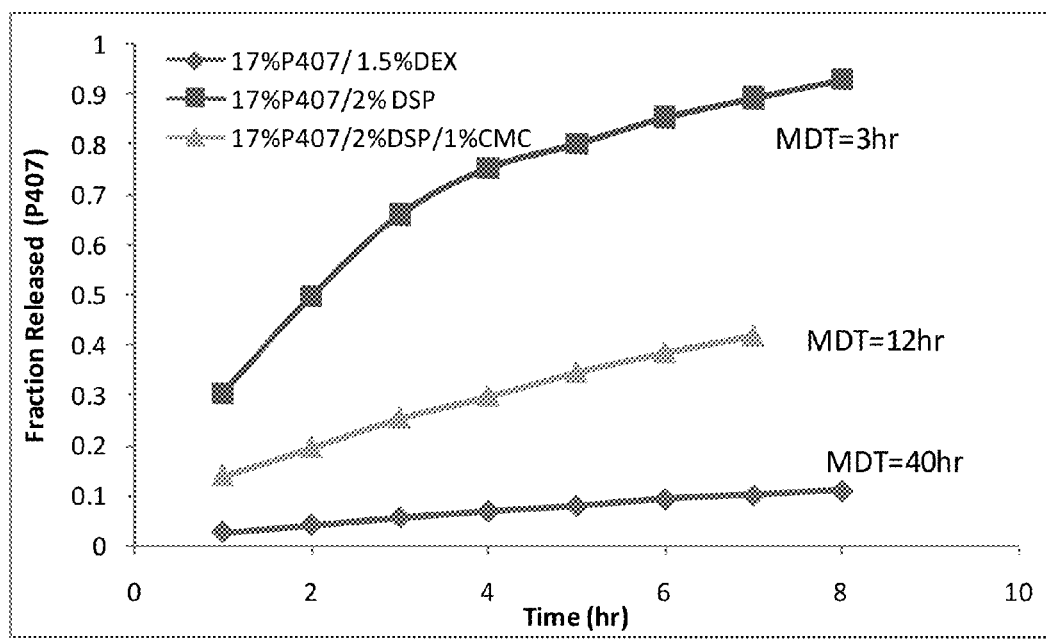
FIG. 3. illustrates release profiles of various steroidal formulations containing 17% P407.

Solubilization of dexamethasone in the 17% poloxamer system is evaluated by measuring the concentration of dexamethasone in the supernatant after centrifuging samples at 15,000 rpm for 10 minutes using an eppendorf centrifuge 5424. Dexamethasone concentration in the supernatant is measured by UV at 245 nm against an external calibration standard curve. FIG. 3. illustrates release profiles of various steroidal formulations containing 17% P407. Table 17 describes dexamethasone solubility in TRIS buffer and 17% P407 solution.

TABLE 9

Dexamethasone solubility in TRIS buffer and 17% P407 solution

| Sample | Dexamethasone concentration in supernatant (µg/mL) |
|---|---|
| 17% P407/1.5% DEX/TRIS | 580 |
| 2% DEX in TRIS buffer (from example 4) | 86 |
| 2% DEX in TRIS buffer autoclaved (from example 4) | 153 |

Example 19

Release Rate or MDT and Viscosity of Formulation Containing Sodium Carboxymethyl Cellulose 17% poloxamer 407/2% DSP/1% CMC (Hercules Blanose 7M): A sodium carboxymethylcellulose (CMC) solution (pH 7.0) in PBS buffer is prepared by dissolving 205.6 mg of sodium chloride (Fisher Scientific), 372.1 mg of sodium phosphate dibasic dihydrate (Fisher Scientific), 106.2 mg of sodium phosphate monobasic monohydrate (Fisher Scientific) in 78.1 g of sterile filtered DI water. 1 g of Blanose 7M CMC (Hercules, viscosity of 533 cP @ 2%) is sprinkled into the buffer solution and heated to ease solution, solution is then cooled down and 17.08 g poloxamer 407NF (Spectrum Chemicals) is sprinkled into the cold solution while mixing. A formulation comprising 17% poloxamer 407NF/1% CMC/2% DSP in PBS buffer is made adding/dissolving 205 mg of dexamethasone to 9.8 g of the above solution, and mixing until all the dexamethasone is completely dissolved. The pH of this solution is 7.0.

17% poloxamer 407/2% DSP/0.5% CMC (Blanose 7M65): A sodium carboxymethylcellulose (CMC) solution (pH 7.2) in PBS buffer is prepared by dissolving 257 mg of sodium chloride (Fisher Scientific), 375 mg of sodium phosphate dibasic dihydrate (Fisher Scientific), 108 mg of sodium phosphate monobasic monohydrate (Fisher Scientific) in 78.7 g of sterile filtered DI water. 0.502 g of Blanose 7M65 CMC (Hercules, viscosity of 5450 cP @ 2%) is sprinkled into the buffer solution and heated to ease solution, solution is then cooled down and 17.06 g poloxamer 407NF (Spectrum Chemicals) is sprinkled into the cold solution while mixing. A 17% poloxamer 407NF/1% CMC/2% DSP solution in PBS buffer is made adding/dissolving 201 mg of DSP to 9.8 g of the above solution, and mixing until the DSP is completely dissolved. The pH of this solution is 7.2.

17% poloxamer 407/2% DSP/0.5% CMC (Blanose 7H9): A sodium carboxymethylcellulose (CMC) solution (pH 7.3) in PBS buffer is prepared by dissolving 256.5 mg of sodium chloride (Fisher Scientific), 374 mg of sodium phosphate dibasic dihydrate (Fisher Scientific), 107 mg of sodium phosphate monobasic monohydrate (Fisher Scientific) in 78.6 g of sterile filtered DI water, then 0.502 g of Blanose 7H9 CMC (Hercules, viscosity of 5600 cP @ 1%) is sprinkled to the buffer solution and heated to ease solution, solution is then cooled down and 17.03 g poloxamer 407NF (Spectrum Chemicals) is sprinkled into the cold solution while mixing. A 17% poloxamer 407NF/1% CMC/2% DSP solution in PBS buffer is made adding/dissolving 203 mg of DSP to 9.8 of the above solution, and mixing until the DSP is completely dissolved. The pH of this solution is 7.3.

Viscosity measurements are performed as described in example 7. Dissolution is performed as described in example 7.

Figure 4:
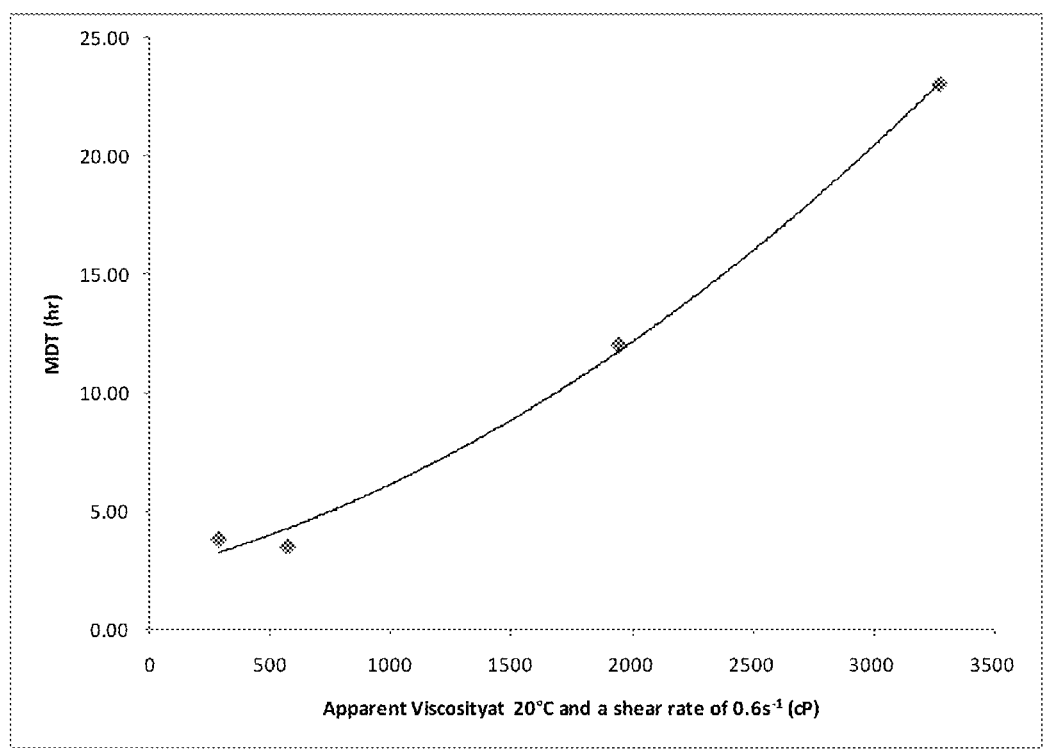
FIG. 4. illustrates the correlation between mean dissolution time (MDT) and apparent viscosity of formulation
Figure 5:
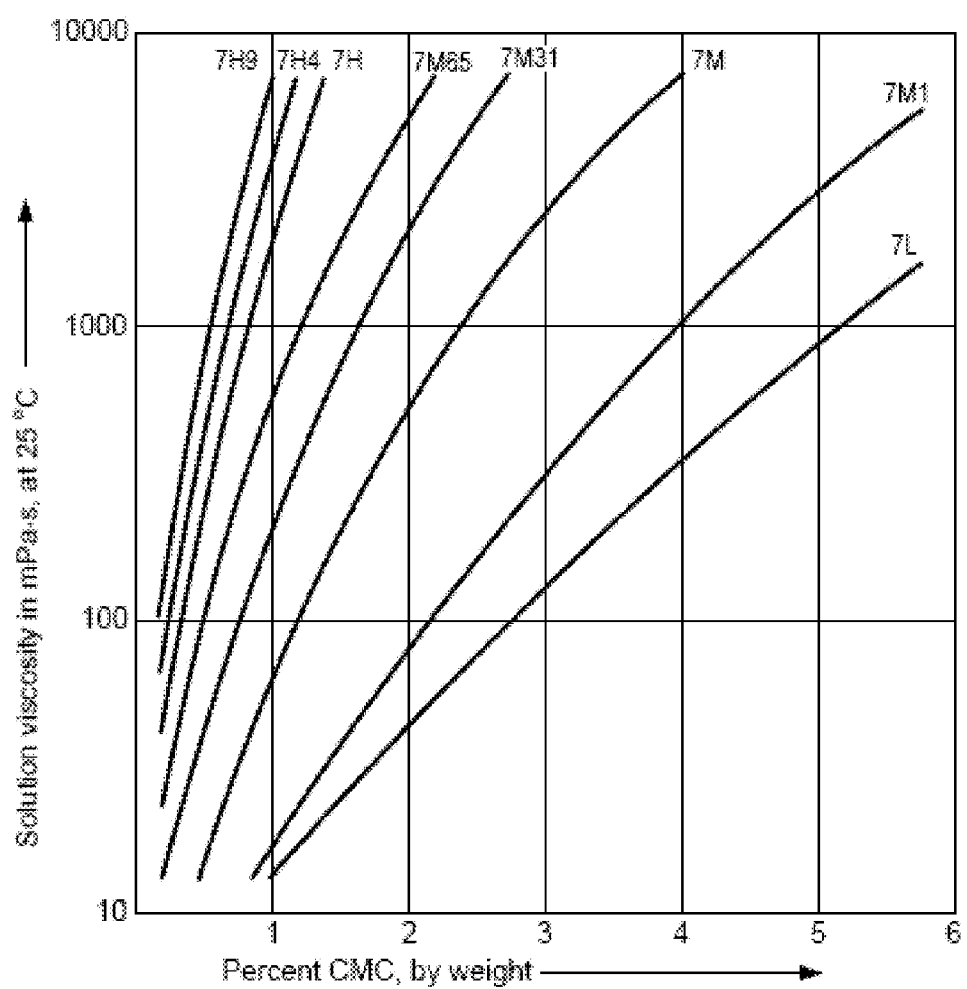
FIG. 5 illustrates the effect of concentration on the viscosity of aqueous solutions of Blanose refined CMC
Figure 6:
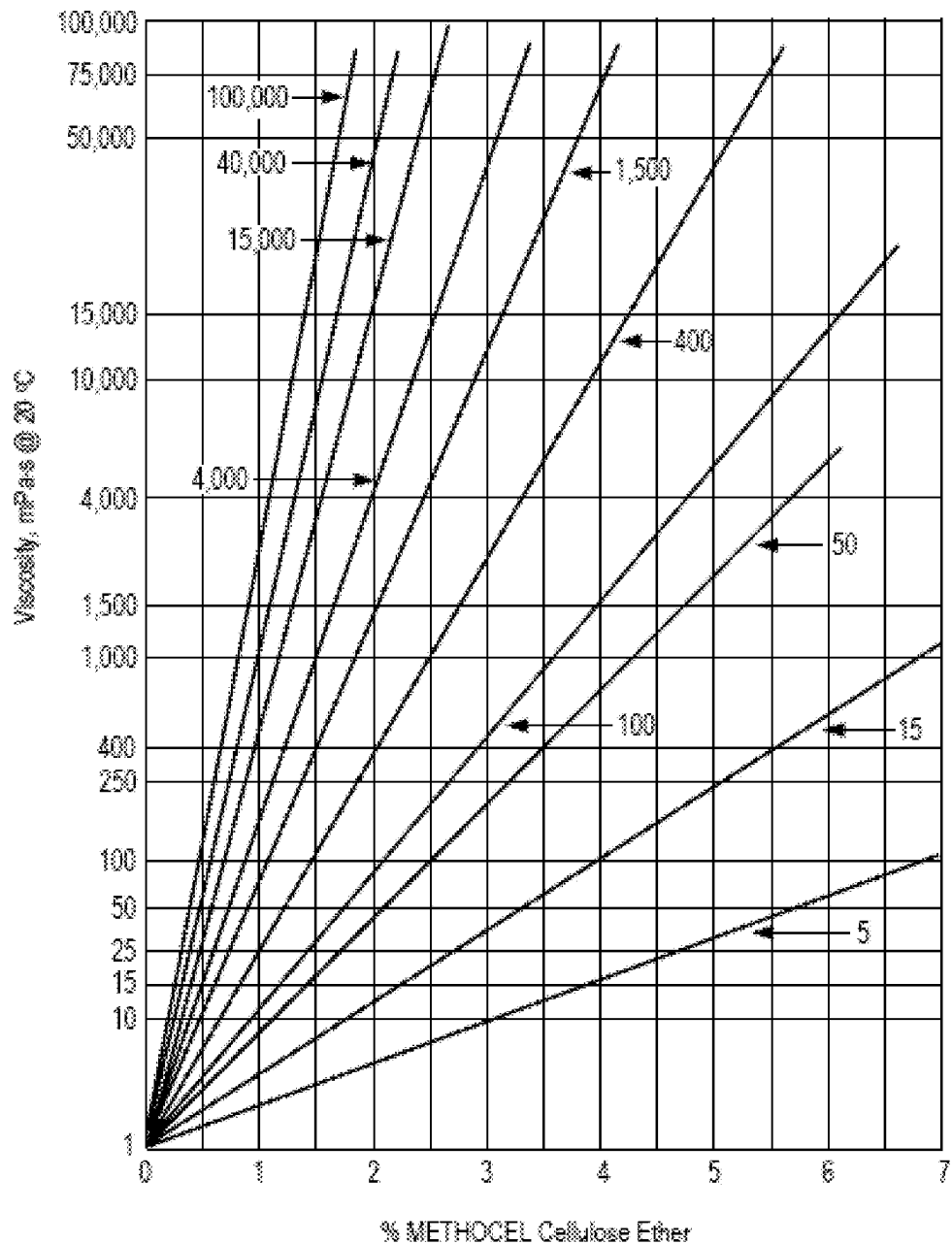
FIG. 6 illustrates the effect of concentration on the viscosity of aqueous solutions of Methocel

FIG. 4. illustrates the correlation between mean dissolution time (MDT) and apparent viscosity of formulation. The release rate is modulated by the incorporation of a secondary polymer. The selection of the grade and concentration of a secondary polymer is facilitated by the use of graphs like the ones shown below in FIG. 5 and FIG. 6 for commonly available water soluble polymers.

Example 20

Dry Sterilization of Micro-Dexamethasone Powder

Ten milligrams of micronized dexamethasone powder (Spectrum lot XD0385) were filled into 2 mL glass vials and sealed with a 13 mm butyl str rubber stopper (Kimble) and placed in the oven at different temperatures for 7-11 hours.

HPLC analysis was performed using an Agilent 1200 equipped with a Luna C18(2) 3 µm, 100 Å, 250×4.6 mm column) using a 30-95 of solvent B (solvent A 35% methanol: 35% water:30% acetate buffer, solvent B 70% methanol:30% acetate buffer pH 4) gradient (1-6 min), then isocratic (95% solvent B) for 11 minutes, for a total run of 22 minutes. Samples were dissolved in ethanol and analyzed. Dry-heat sterilization of micronized dexamethasone at a temperature of up to 138° C. did not affect particle size distribution of the micronized dexamethasone. HPLC analysis indicated 99% purity of the dry-heat sterilized micronized dexamethasone.

Example 21

Application of a Enhanced Viscosity Corticosteroid Formulation onto the Round Window Membrane A formulation according to Example 1 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the anti-inflammatory corticosteroid formulation applied directly onto the round window membrane.

Example 22

Figure 7:
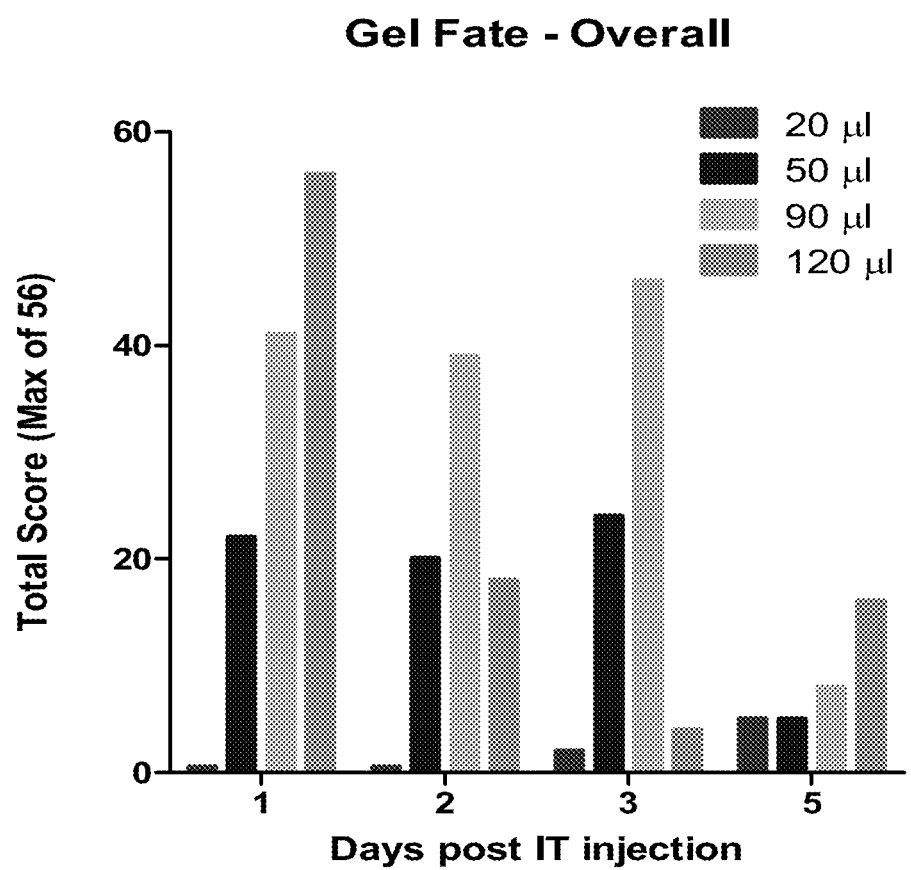
FIG. 7 illustrates the gel fate in the guinea pig ear up to 5 days after intratympanic injection.

In Vivo Testing of Intratympanic Injection of Corticosteroid Formulation in a Guinea Pig A cohort of 21 guinea pigs (Charles River, females weighing 200-300 g) was intratympanically injected with 20-120 µL of a 2% DSP formulation. FIG. 7 shows the gel fate in the guinea pig ear up to 5 days after intratympanic injection. Increasing injection volume increased gel retention for injection volumes up to 90 µL. However, an injection volume of 120 µL showed a lower gel retention.

Figure 8:
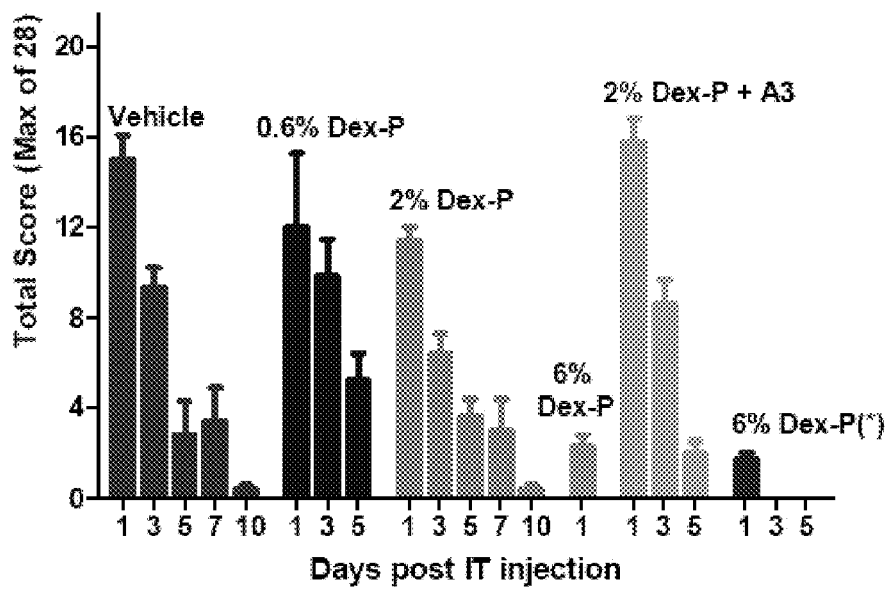
FIG. 8 illustrates the gel elimination time course for formulations described herein
Figure 8:
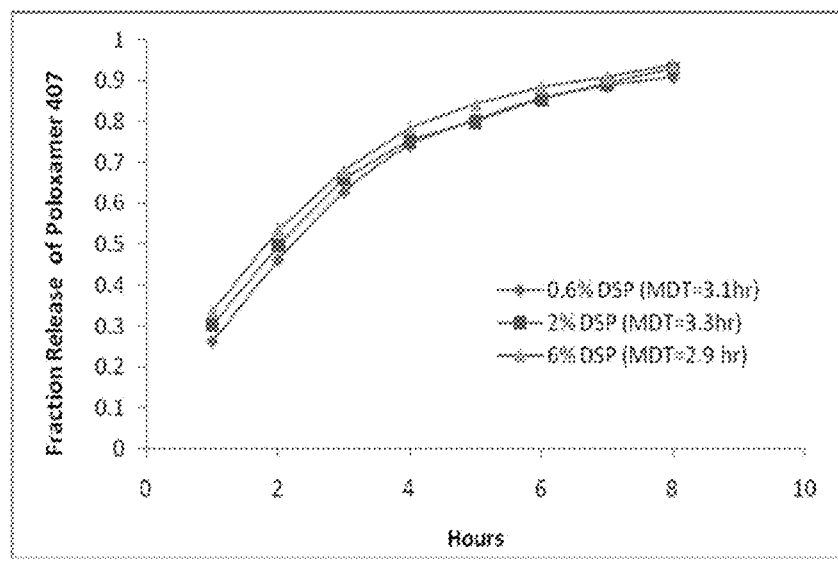

A cohort of 21 guinea pigs (Charles River, females weighing 200-300 g) was intratympanically injected with 50 μL of different P407-DSP formulations described herein, containing 0 to 6% DSP. FIGS. 8A and 8B show the gel elimination time course for each formulation. The gel elimination time course of a 6% DSP formulation was faster (lower mean dissolution time (MDT)) than those of the other formulations containing lower concentrations of DSP (0, 0.6, and 2% respectively). Furthermore, when the P407 concentration was increased from 17% to 19% for the 6% DSP formulation (6% Dex-P(*)), a faster gel elimination was observed, as shown in FIG. 8A. Thus the injection volume and the concentration of a corticosteroid in a formulation described herein are tested to determine optimal parameters for preclinical and clinical studies. It was observed that intratympanic formulations with high concentrations of DSP have a release profile that is different form intratympanic formulations with a lower concentration of DSP.

Example 23

In Vivo Extended Release Kinetics

Figure 9:
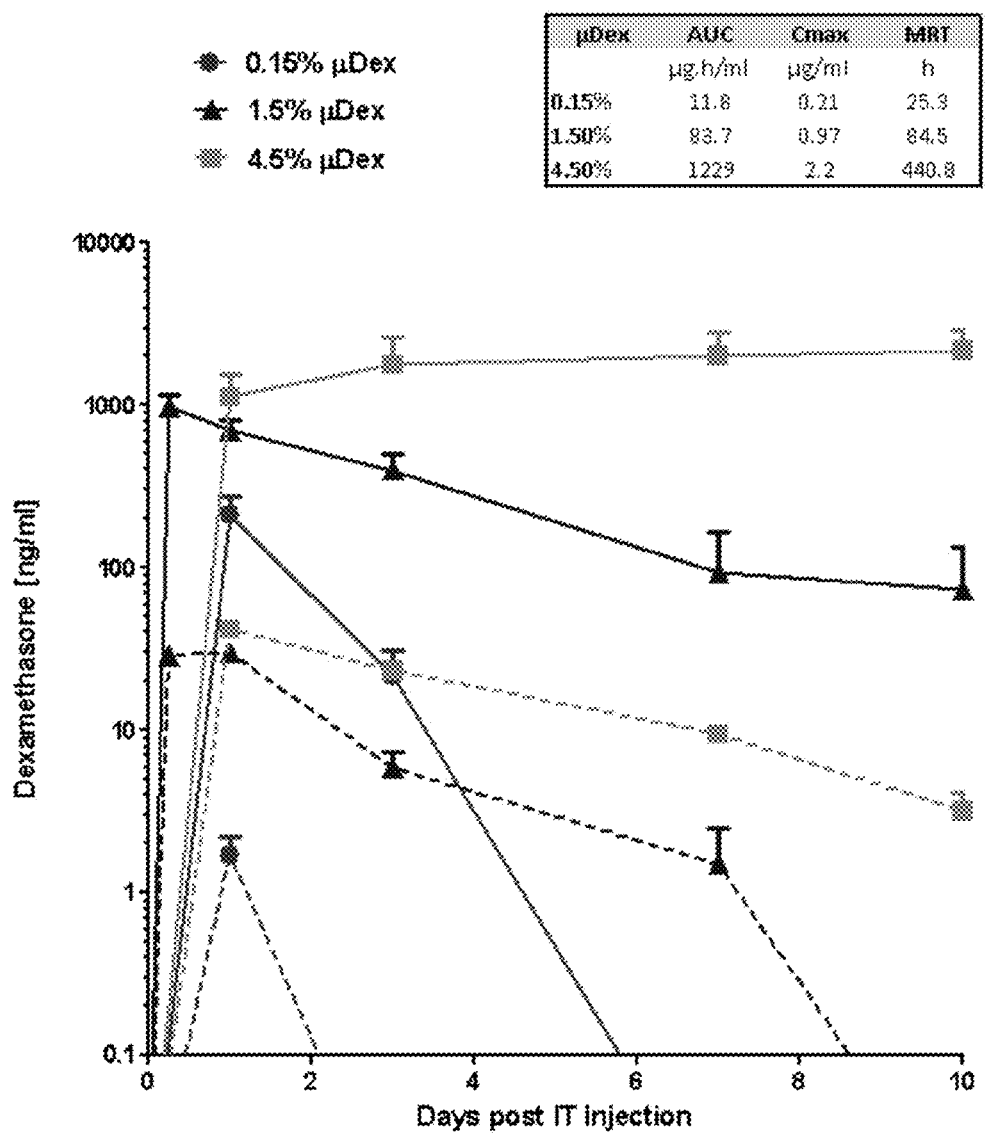
FIG. 9 illustrates the release profile for formulations described herein
Figure 10:
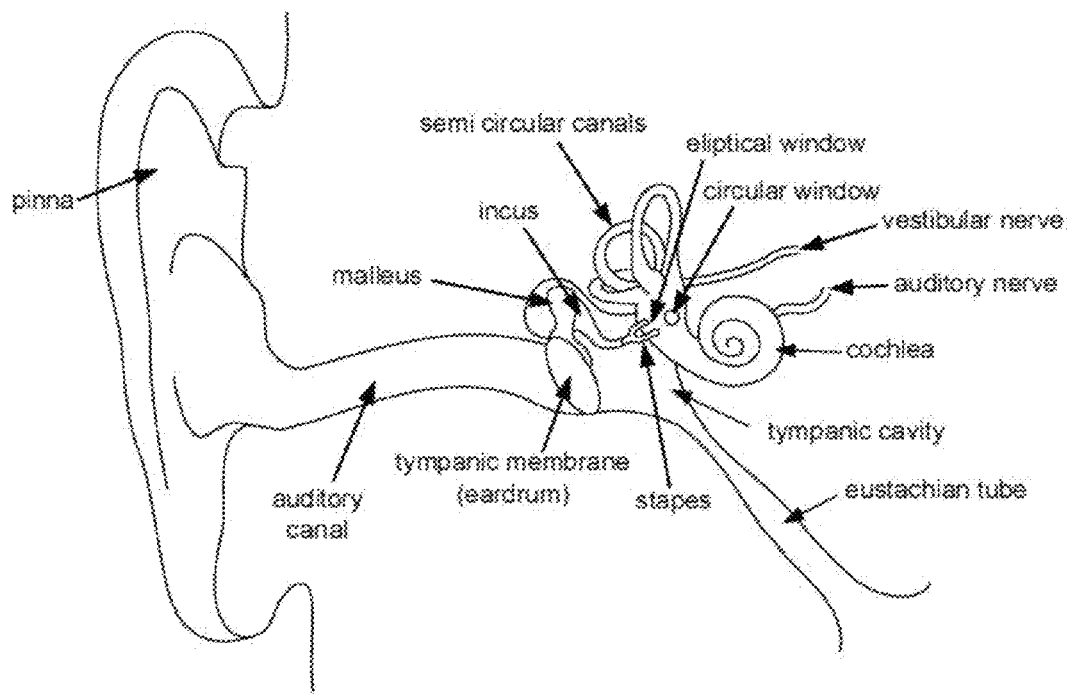
FIG. 10 illustrates the anatomy of the ear

A cohort of 21 guinea pigs (Charles River, females weighing 200-300 g) was intratympanically injected with 50 μL 17% Pluronic F-127 formulation buffered at 280 mOsm/kg and containing 1.5% to 4.5% dexamethasone by weight of the formulation. Animals were dosed on day 1. FIG. 9 shows the release profile for the formulations that were tested base on analysis of the perilymph. In the 1.5% Dexamethasone regimen, the exposure levels at day 7-10 are about 10% of the Cmax with a mean residence time of about 3.5 days. In the 4.5% Dexamethasone regimen, the exposure levels were maintained for at least 10 days at levels similar to or higher than the levels seen at day 1 with a projected mean residence time of over 18 days.

Example 24

Evaluation of Corticosteroid Formulations in an AIED Animal Model

Methods and Materials
Induction of Immune Response
Female albino National Institutes of Health-Swiss mice (Harlan Sprague-Dawley, Inc., Indianapolis, Inc.) weighing 20 to 24 g are used. Keyhole limpet hemocyanin (KLH; Pacific Biomarine Supply Co., Venice, Calif.) is suspended in phosphate-buffered saline (PBS) (pH 6.4), dialyzed aseptically against PBS and centrifuged twice. The precipitate (associated KLH) is dissolved in PBS and injected subcutaneously in the back of the animal (0.2 mg emulsified in Freund's complete adjuvant). The animals are given a booster (0.2 mg KLH in Freund's incomplete adjuvant, and then injected ten weeks later with 0.1 mg KLH in 5 μl PBS (pH 6.4) through a microhole drilled through the cochlear capsule. The cochlea is approached using an operating microscope and sterile technique. A postauricular incision is made, and a hole is drilled into the bullae to allow good visualization of the promontory of the cochlear basal turn, stapedial artery, and round window niche. The stapedial artery is cauterized and removed, and a 25 μm hole is drilled through the cochlear capsule into the scala tympani of the lateral basal turn. KLH or PBS control is slowly injected using a Hamilton syringe coupled with a plastic tube to a glass micropipette filled with the antigen or control. The hole is sealed with bone wax after injection, and excess fluid is removed. Only one cochlea per animal is treated with KLH.

Treatment
KLH and control mice are sorted into two groups (n=10 in each group). Corticosteroid formulation of Example 1 containing dexamethasone is applied to the round window membrane of one group of animals. Control formulation containing no dexamethasone is applied to the second group. The dexamethasone and control formulations are reapplied three days after the initial application. The animals are sacrificed after the seventh day of treatment.

Analysis of Results
Electrophysiologic Testing
The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, NY, USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Histochemical Analysis
Animals are anesthetized and sacrificed via intracardiac perfusion of heparinized warm saline followed by approximately 40 ml periodate-lysine-paraformaldehyde (4% paraformaldehyde final concentration) fixative. Right-side temporal bones are immediately removed and decalcified with buffered 5% ethylenediamine tetra-acetate (pH 7.2) for 14 days (4° C.). After decalcification, temporal bones are immersed sequentially in increasing concentrations (50%, 75%, 100%) of optimal cutting temperature (OCT) compound (Tissue-Tek, Miles Inc., Elkhart, Ind.), snap-frozen (−70° C.), and cryostat-sectioned (4 μm) parallel to the modiolus. Sections are collected for hematoxylin and eosin (H&E) staining and immunohistochemical analysis.

The severity of inflammation is assessed according to the amount of cellular infiltration of the scala tympani, and an unbiased score is given to each cochlea. A score of 0 indicates no inflammation, and a score of 5 indicates that all cochlear turns had severe infiltration of inflammatory cells.

Example 25

Evaluation of Corticosteroid Formulations in an Otitis Media Animal Model

Induction of Otitis Media
Healthy adult chinchillas weight 400 to 600 g with normal middle ears, ascertained by otoscopy and tympanometry are used for these studies. Eustachian tube obstruction is performed 24 hours before inoculation to prevent the inoculum from flowing out of the eustachian tube. One milliliter of type 3 S. pneumoniae strain at 4-h-log phase (containing approximately 40 colony forming units (CFU)) is placed directly into both middle ear hypotympanic bullae of the chinchillas. Control mice are inoculated with one milliliter sterile PBS.

Treatment

S. pneumoniae inoculated and control mice are sorted into two groups (n=10 in each group). The prednisolone formulation of Example 2 is applied to the walls of the tympanic cavity of one group of animals. Control formulation containing no prednisolone is applied to the second group. The prednisolone and control formulations are reapplied three days after the initial application. The animals are sacrificed after the seventh day of treatment.

Analysis of Results

Auris media ear fluid (MEF) is sampled at 1, 2, 6, 12, 24, 48 and 72 hours after pneumoccal inoculation. Quantitative MEF cultures are performed on sheep blood agar, with the quantitation threshold set at 50 CFU/ml. Inflammatory cells are quantitated with a hemocytometer, and differential cell enumeration performed with Wright's staining.

Example 26

AIED Clinical Trials using a Dexamethasone Formulation

Ten adult patients who have previously responded to systemic dexamethasone therapy, but currently have discontinued therapy due to adverse events are selected. The dexamethasone thermoreversible gel formulation of Example 1 is administered to each patient's round window membrane through piercing of the tympanic membrane. Reapplication of the dexamethasone gel formulation is performed 7 days after the initial application, and again at 2 and 3 weeks of treatment.

Hearing evaluations consisting of pure tone audiometry (250-8000 Hz) and speech testing using disyllabic word lists in French are administered to each patient. Testing is carried out both before the application of the dexamethasone formulation and at 1, 2, 3 and 4 weeks post-initial treatment.

Example 27

Evaluation of Prednisolone in an Acoustic Trauma Mouse Model

Methods and Materials

Induction of Ototoxicity

Twelve Harlan Sprague-Dawley mice weighing 20 to 24 g are used. Baseline auditory brainstem response (ABR) at 4-20 mHz is measured. The mice are anesthetized and exposed for 30 minutes to a continuous pure tone of 6 kHz at a loudness of 120 dB.

Treatment

The control group (n=10) are administered saline following acoustic trauma. The experimental group (n=10) are administered prednisolone as formulated in Example 2 (2.0 mg/kg of body weight) following acoustic trauma.

Electrophysiologic Testing

The hearing threshold for the auditory brainstem response threshold (ABR) to click stimuli for each ear of each animal is initially measured and 1 week after the experimental procedure. The animals are placed in a single-walled acoustic booth (Industrial Acoustics Co, Bronx, NY, USA) on a heating pad. Subdermal electrodes (Astro-Med, Inc. Grass Instrument Division, West Warwick, R.I., USA) were inserted at the vertex (active electrode), the mastoid (reference), and the hind leg (ground). Click stimuli (0.1 millisecond) are computer generated and delivered to a Beyer DT 48, 200 Ohm speaker fitted with an ear speculum for placement in the external auditory meatus. The recorded ABR is amplified and digitized by a battery-operated preamplifier and input to a Tucker-Davis Technologies ABR recording system that provides computer control of the stimulus, recording, and averaging functions (Tucker Davis Technology, Gainesville, Fla., USA). Successively decreasing amplitude stimuli are presented in 5-dB steps to the animal, and the recorded stimulus-locked activity is averaged (n=512) and displayed. Threshold is defined as the stimulus level between the record with no visibly detectable response and a clearly identifiable response.

Example 28

Clinical Trials of Dexamethasone in Meniere's Disease Patients

Study Objective

The primary objective of this study will be to assess the safety and efficacy of dexamethasone compared with that of placebo in ameliorating tinnitus symptoms in Meniere's Disease afflicted patients.

Study Design

This will be a phase 3, multicentre, double-blind, randomised, placebo-controlled, three-arm study comparing JB004/A to placebo in the treatment of tinnitus. Approximately 250 subjects will be enrolled in this study, and randomised (1:1) to 1 of 3 treatment groups based on a randomization sequence prepared by sponsor. Each group will receive 300 mg dexamethasone delivered in a thermoreversible gel, or controlled release placebo formulation. Release of dexamethasone is controlled release and occurs over 30 days. Route of Administration will be intratympanic injection.

Primary Outcome Measure

Visual Analog Scales (VAS) to measure the change in tinnitus loudness as perceived at the moment of the measurement at 2 hrs after dosing (or at any other time point vs. pre-dose baseline). Alternatively, audiometry is used in the healthy ear to match the tone of the tinnitus in the affected ear.

Secondary Outcome Measures

VAS to measure tinnitus pitch, distress and anxiety. Pure Tone Audiometry & Psychoacoustic assessment. Sleep & Tinnitus questionnaires. Safety, tolerability and pharmacokinetics of drug. [Time Frame: perceived at the moment of the measurement at 2 hrs after dosing (or at any other time point vs. pre-dose baseline).

Inclusion Criteria

Patients may be included if they meet any of the following criteria:

Male or female subjects diagnosed with a tinnitus.

Subjects willing to restrict alcohol intake.

Women of childbearing potential who abstain from intercourse OR agree to birth control.

Women of non-childbearing potential.

Exclusion Criteria

Patients may be excluded if they meet any of the following criteria:

Intermittent or pulsatile tinnitus

Subject with pathologic level of anxiety or depression.

Subject with no audiogram deficit and with normal hearing.

Subjects that do not respond to the lidocaine infusion test or show a large variability in pre-infusion values.

Existence of any surgical or medical condition which might interfere with the PK of the drug.
Subjects with hepatic impairment or a history of liver dysfunction.
Subjects with renal impairment.
Subjects positive for HIV, hepatitis C or hepatitis B.
Subjects with abnormal laboratory, ECG or physical examination findings.
Subjects who are not euthyroid.
Subjects with a history of hepatic, cardiac, renal, neurologic, cerebrovascular, metabolic or pulmonary disease.
Subjects who have had a myocardial infarction.
Subjects with a history of seizure disorders.
Subjects with history of cancer.
Subjects with a history of drug or other allergy.
Subjects positive for drug use and/or a history of substance abuse or dependence.
Subjects who have taken psychotropic drugs or antidepressants within specified time frames.
Medication or foodstuff (e.g. grapefruit or grapefruit juice) which is known to interfere with liver enzymes.
Subjects who have recently used an investigational drug or recently participated in a trial.
Women who have a positive pregnancy test.
Female subjects who intend to get pregnant or male subjects who intend to father a child within the next 4 weeks following the last study drug administration in the study.
Subjects, who have donated a unit of blood or more within the previous month or who intend to donate blood within one month of completing the study.

Example 29

Evaluation of a Dexamethasone Formation in an Endolymphatic Hydrops Animal Model The procedure is used to determine the efficacy of the dexamethasone formulation prepared in Example 1.
Materials and Methods
Thirty-five Hartley guinea pigs with a positive Preyer's reflex and weighing about 300 g are used. Five animals, which serve as controls (normal ear group), are fed for 5 weeks with neither operation nor treatment, and the remaining 30 serve as experimental animals. All experimental animals received electro-cauterization of the endolymphatic sac (Lee et al., Acta Otolaryngol. (1992) 112:658-666; Takeda et al., Equilib. Res. (1993) 9:139-143). Four weeks after surgery, these animals are divided into three groups of non-infusion hydropic ears, vehicle-treated hydropic ears and dexamethasone-treated hydropic ears, consisting of 10 animals each. The group of non-infusion hydropic ears receive no treatment except for electro-cauterization of the endolymphatic sac. In the groups of vehicle-treated hydropic ears and dexamethasone-treated hydropic ears, the liposomal formulation is applied to the round window membrane. One week after administration of the composition, all animals are sacrificed for assessment of the changes of the endolymphatic space. All animals are left undisturbed and freely moving in individual cages in a quiet room throughout the period, except during experimental procedures.
To assess the changes to the endolymphatic space, all animals are transcardially perfused with physiological saline solution under deep anesthesia by a peritoneal-injection of pentobarbital, and fixation is performed with 10% formalin. The left temporal bones are removed and postfixed in 10% formalin solution for 10 days or more. Thereafter, they are decalcified with 5% trichloroacetic acid for 12 days and dehydrated in a graded ethanol series. They are embedded in paraffin and celloidin. The prepared blocks are cut horizontally into 6 μm sections. The sections are stained with hematoxylin and eosin and observed under a light microscope. Quantitative assessment of changes of the endolymphatic space is performed according to the method of Takeda (Takeda et al., Hearing Res. (2003) 182:9-18).

Example 30

Evaluation of Intratympanic Dexamethasone on Idiopathic Sudden Sensorineural Hearing Loss (ISSHL)

Study Objective
The primary objective of this study will be to assess the safety and efficacy of oral steroid treatment, or intratympanic (IT) steroid treatment.
Primary Outcome Measurements
Pure Tone Average (PTA) and Word Recognition as equally weighted endpoints; For Speech Discrimination Scoring, a 50-word monosyllable system will be employed; Greater than 20 dB improvement in PTA or over ALL or SOME of the frequencies where the deficiencies are greater than 30 dB, and/or a 20% or greater improvement in the WDS; In addition to absolute changes, recovery with respect to the contralateral ear will also be determined.
Complete Recovery—recovery to within 5% points of the contralateral speech discrimination score, or within 5 dB of the contralateral PTA.
Study Design
This will be a multicentre, double-blind, randomized, placebo-controlled, parallel group study comparing intratympanic Dexamethasone to placebo in the treatment of ISSHL. Approximately 140 subjects will be enrolled in this study, and randomized (1:1) to 1 of 3 treatment groups based on a randomization sequence.
  a. Subjects in Group I will receive oral prednisone (1 mg/kg/day prednisone for 14 days followed by a daily 10 mg diminution in dose until no further steroid is given)
  b. Subjects in Group II will receive IT dexamethasone sodium phosphate (1 injection of 0.3-0.5 mL of dexamethasone/mL of vehicle administered monthly up to a maximum of 3 injections) and oral prednisone (1 mg/kg/day prednisone for 14 days followed by a daily 10 mg diminution in dose until no further steroid is given)
  c. Subjects in Group III will receive a placebo IT injections (1 injection of 0.3-0.5 mL of vehicle administered monthly up to a maximum of 3 injections) and oral prednisone
Hearing Assessments
  Hearing assessments comprise:
  a. Pure Tone Average (500 Hz, 1 & 2 kHz; 4, 6 & 8 kHz).
    i. Two PTA values would then be determined: a low frequency value (500 Hz-2 kHz) and a high frequency value (4-8 kHz).
  b. Stapedial Reflex
  c. Tympanometry & tone decay
  d. Speech Recognition Threshold
Before treatment begins hearing loss for each subject will be measured (twice prior to allocation to the study, and once prior to randomization). Hearing assessment at 1, 2, 4 & 8 weeks, 4& 6 months post start of treatment
Main Criteria for Inclusion
  Male or female patients aged between 18 and 75 years
  Unilateral SHL (sensorineural hearing loss) developing within 72 hours Subjects will have a hearing loss that at any one frequency, does not exceed 70 dB.
Exclusion Criteria
 Greater than 10 days of prior oral steroid treatment for any reason within the preceding 30 days
 5 or more days of prior oral steroid treatment for ISSHL within the preceding 14 days
 History of fluctuating hearing in either ear Example 31

Evaluation of Intratympanic Dexamethasone on Meniere's Disease

Study Objective
 The primary objective of this study will be to assess the safety and efficacy of intratympanic (IT) dexamethasone treatment.
Primary Outcome Measurements
 Vertigo
  a. Self-Reporting System with the following regimen—
   i. Vertigo-free days—0 score;
   ii. Days with a mild attack—1;
   iii. Moderately severe attacks lasting more than 20 minutes—2;
   iv. Severe attacks lasting an hour or more or accompanied by nausea or vomiting—3;
   v. Worst attack to date—4;
   vi. Treatment failure to be defined as a monthly vertigo score of 50 or greater for 2 consecutive months
Inclusion Criteria
 Clinical diagnosis of MD according to the 1995 AAO-HNS Criteria:
  a. At least two definitive attacks of vertigo.
  b. A definitive spell is spontaneous (rotational) vertigo lasting at least 20 minutes.
Exclusion Criteria
 Treatment with aminoglycoside or macrolide antibiotics;
 Treatment with antineoplastic drugs
  a. Platinum compounds,
  b. Difluoromethylornithine
Study Design
 This will be a multicentre, double-blind, randomized, placebo-controlled, parallel group study comparing intratympanic dexamethasone to placebo in the treatment of ISSHL. Approximately 140 subjects will be enrolled in this study, and randomized (1:1) to 1 of 3 treatment groups based on a randomization sequence.
  a. Subjects in Group I will receive standard of care (sodium diet of nmt 1500 mg/day, abstinence from xanthine intake, and/or diuretics)
  b. Subjects in Group II will receive IT dexamethasone sodium phosphate (1 injection of 0.3-0.5 mL of dexamethasone/mL of vehicle administered monthly up to a maximum of 3 injections) and standard of care
  c. Subjects in Group IV will receive a placebo IT injections (1 injection of 0.3-0.5 mL of vehicle administered monthly up to a maximum of 3 injections) and standard of care Assessments
 Before treatment begins severity of Meniere's for each subject will be measured (twice prior to allocation to the study, and once prior to randomization)
 Meniere's assessment at 1, 2, 4 & 8 weeks, 4 & 6 months post start of treatment
  Assessments
   a. Date of onset, frequency, duration and severity of attacks of vertigo and tinnitus;
   b. Reduced aural pressure sensation, measured using standard VAS questionnaires, and validated rating protocols
   c. Measurement of serum vasopressin While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:

1. A method of alleviating or ameliorating the symptoms of otic disorders selected from Meniere's disease, Autoimmune ear disease (AIED), otitis media, acoustic trauma induced sensorineural hearing loss, drug induced sensorineural hearing loss, sensorineural hearing loss due to infection, idiopathic sensorineural hearing loss, vertigo, and tinnitus, in an individual in need thereof comprising intratympanic administration of a pharmaceutical composition on or near the round window membrane of the ear of the individual in need thereof, the composition comprising an auris acceptable thermoreversible aqueous gel comprising a polymer of polyoxypropylene and polyoxyethylene; and between about 1-70 mg/mL of a multiparticulate anti-inflammatory corticosteroid; such that sustained release of the anti-inflammatory corticosteroid across the round window membrane into the cochlea occurs for a period of at least 5 days after a single administration.

2. A method according to claim 1, wherein the anti-inflammatory corticosteroid is dexamethasone, dexamethasone ester, or pharmaceutically acceptable salt thereof.

3. A method according to claim 1, wherein the anti-inflammatory corticosteroid is methylprednisolone, or pharmaceutically acceptable salt thereof.

4. A method according to claim 1, wherein the anti-inflammatory corticosteroid is prednisolone, or pharmaceutically acceptable salt thereof.

5. A method according to claim 1, wherein the composition has a pH between about 6.6 and about 8.0.

6. A method according to claim 1, further comprising a delivery system for the delivery of the composition to or near to the round window.

7. A method according to claim 6, wherein the delivery system comprises a needle for delivery of the composition.

8. A method according to claim 7, wherein the needle is part of a syringe and needle apparatus, a hypodermic needle, a micro-otoscope.

9. A method according to claim 1, wherein the polymer of polyoxypropylene and polyoxyethylene is present in an amount sufficient to allow injection of the formulation through the tympanic membrane by a 18-31 gauge needle.

* * * * *

UNITED STATES PATENT AND TRADEMARK OFFICE
CERTIFICATE OF CORRECTION

PATENT NO.       : 8,680,082 B2                                       Page 1 of 1
APPLICATION NO.  : 13/190323
DATED            : March 25, 2014
INVENTOR(S)      : Jay Lichter et al.

It is certified that error appears in the above-identified patent and that said Letters Patent is hereby corrected as shown below:

In the Specification

On the first page of the specification, insert new heading and paragraph under Cross-References, in column 1, line 23:

-- JOINT RESEARCH AGREEMENT

The claimed invention was made as a result of activities undertaken within the scope of a joint research agreement between Jay Benjamin Lichter, Benedikt K. Vollrath, Otonomy Inc., and Avalon Ventures VIII GP, LLC that was in effect on or before the date the invention was made. --

Signed and Sealed this
Twenty-fourth Day of June, 2014

Michelle K. Lee
*Deputy Director of the United States Patent and Trademark Office*